(12) United States Patent
Poetsch et al.

(10) Patent No.: US 7,314,943 B2
(45) Date of Patent: *Jan. 1, 2008

(54) PYRAN DERIVATIVES CONTAINING AN EXOCYCLIC DOUBLE BOND

(75) Inventors: Eike Poetsch, Muehltal (DE); Volker Meyer, Gross-Zimmern (DE); Werner Binder, Dieburg (DE); Michael Heckmeier, Hemsbach (DE); Georg Luessem, Petershausen (DE); Stephan Guertler, Griesheim (DE)

(73) Assignee: Merck Patent GmbH, Darmstadt (DE)

( * ) Notice: Subject to any disclaimer, the term of this patent is extended or adjusted under 35 U.S.C. 154(b) by 221 days.

This patent is subject to a terminal disclaimer.

(21) Appl. No.: 10/852,731

(22) Filed: May 25, 2004

(65) Prior Publication Data

US 2005/0038267 A1 Feb. 17, 2005

(30) Foreign Application Priority Data

May 27, 2003 (DE) ................................ 103 24 348

(51) Int. Cl.
*C07D 315/00* (2006.01)
(52) U.S. Cl. ...................... 549/428; 549/426; 549/427; 549/294; 252/299.61
(58) Field of Classification Search ................ 514/337; 549/356, 426, 427, 428; 252/299.61
See application file for complete search history.

(56) References Cited

U.S. PATENT DOCUMENTS 4,818,431 A 4/1989 Eidenschink et al.
5,480,580 A 1/1996 Sakashita et al.
6,902,777 B2 * 6/2005 Hirschmann et al. ........ 428/1.1

FOREIGN PATENT DOCUMENTS

DE 3306960 A 8/1984
DE 19640618 A 4/1998
EP 0409066 A 1/1991

OTHER PUBLICATIONS

Mori et al CA129:513025, RN213331-33-OP (1998).*
Ando et al., 1992, CAS Accession No. 1992: 407915.*
Ando et al., 1991, CAS Accession No. 1991: 143401.*
Reissenweber et al., 1985, CAS Accession No. 1985: 78433.*
Marschall et al., 1982, CAS Accession No. 1982: 455610.*
Mori et al., J. Org. Chem., 1998, 63, 6082-6083.*
Mori et al., 1998, CAS Accession 1998: 513025.*

* cited by examiner

*Primary Examiner*—Amelia A. Owens
(74) *Attorney, Agent, or Firm*—Millen, White, Zelano & Branigan, P.C.

(57) ABSTRACT

The invention relates to pyran derivatives of formula I $$R^{11}-\!\!\left[A^{11}\right]_{a}\!-\!\left[Z^{11}-A^{12}\right]_{b}\!-\!Z^{12}-CH\!=\!CH\!-\!\!\!\underset{W-O}{\overbrace{\phantom{XXXXX}}}$$
$$-Z^{13}-\!\!\left[A^{13}-Z^{14}\right]_{c}\!-\!A^{14}-Z^{15}\!\left[\right]_{d}\!\left[A^{15}\right]_{e}\!R^{12},\quad I$$

and processes and intermediates for their preparation and derivatisation, and the use thereof in liquid-crystalline media.

33 Claims, No Drawings

PYRAN DERIVATIVES CONTAINING AN EXOCYCLIC DOUBLE BOND

The invention relates to pyran derivatives containing an exocyclic double bond, to processes and intermediates for their preparation and derivatisation, and to the use thereof in liquid-crystalline mixtures.

Pyran derivatives play an important role in chemistry and pharmacy, inter alia as ingredients of natural and synthetic aroma substances, in medicaments and in liquid-crystalline materials. However, preparative access to many pyrans, in particular those with a 2,5-disubstitution, is currently limited and is often restricted to derivatisation of carbohydrates containing pyranose ring units. Many theoretically conceivable pyran derivatives are hitherto not accessible synthetically.

It is therefore an object of the present invention to provide novel pyran derivatives which have industrially useful properties or can serve as starting compounds for the efficient synthesis of further pyran derivatives.

This object is achieved by compounds of the general formula I

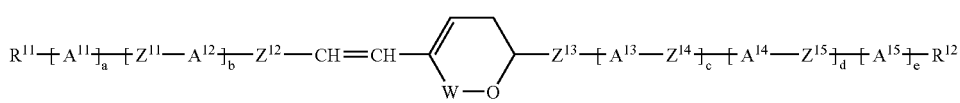

I where a, b, c, d and e are each, independently of one another, 0 or 1;

W is —CH$_2$— or —C(=O)—;

R$^{11}$ is H, an alkyl radical having from 1 to 15 carbon atoms which is unsubstituted or mono- or polysubstituted, identically or differently, by halogen or —CN, where, in addition, one or more CH$_2$ groups in this radical may be replaced by —C≡C—, —CH=CH—, —O—, —S—, —C(O)—O— and/or —O—C(O)— in such a way that hetero atoms (O and S) are not linked directly to one another;

R$^{12}$ is H, halogen, —CN, —NCS, aralkyl, —O-aralkyl or an alkyl radical having from 1 to 15 carbon atoms which is unsubstituted or mono- or polysubstituted, identically or differently, by halogen or —CN, where, in addition, one or more CH$_2$ groups in this radical may be replaced by —C≡C—, —CH=CH—, —O—, —S—, —C(O)—O— and/or —O—C(O)— in such a way that hetero atoms (O and S) are not linked directly to one another;

Z$^{11}$ is a single bond, —CH$_2$—, —CH$_2$CH$_2$—, —CF$_2$CH$_2$—, —CH$_2$CF$_2$—, —CF$_2$CF$_2$—, —CH=CH— or —C≡C—;

Z$^{12}$ is a single bond, —CH$_2$—, —CH$_2$CH$_2$—, —CF$_2$CH$_2$—, —CH$_2$CF$_2$— or —CF$_2$CF$_2$—;

Z$^{13}$, Z$^{14}$ and Z$^{15}$ are each, independently of one another, a single bond, —CH$_2$CH$_2$—, —CF$_2$CH$_2$—, —CH$_2$CF$_2$—, —CF$_2$CF$_2$—, —CH=CH—, —C≡C—, —CH$_2$O—, —CF$_2$O—, —C(O)— or —C(O)—O—;

A$^{11}$ and A$^{12}$, independently of one another, are

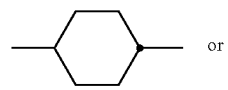

A$^{13}$ and A$^{14}$, independently of one another, are

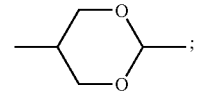

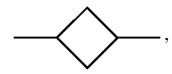

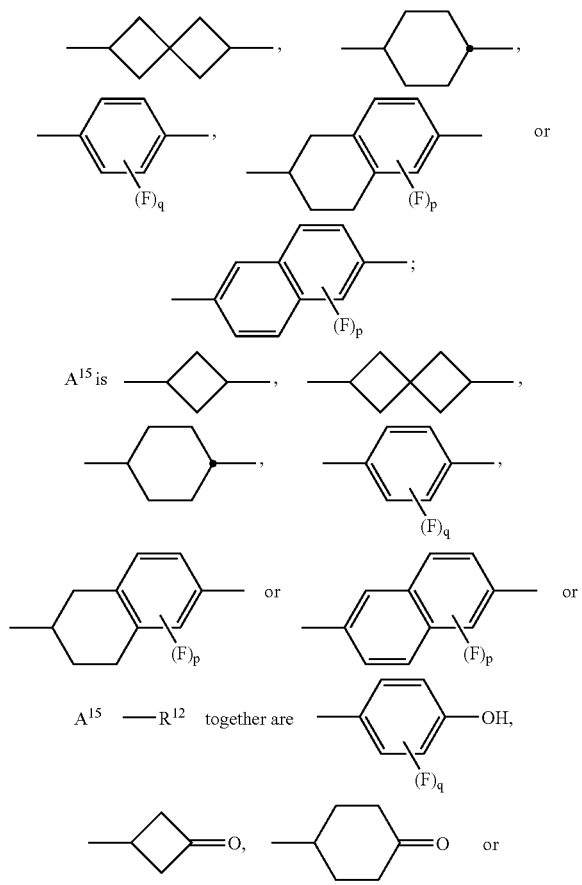

-continued

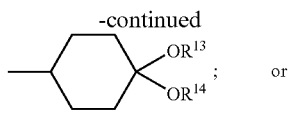

or $Z^{13}$-[-$A^{13}$-$Z^{14}$-]$_c$-[-$A^{14}$-$Z^{15}$-]$_d$-[-$A^{15}$-]$_e$-$R^{12}$ is

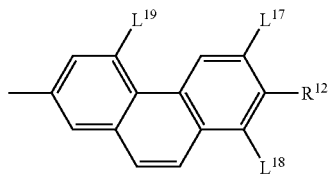

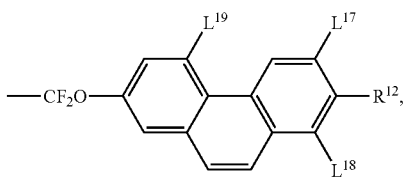

where $R^{12}$ is as defined above, and $L^{17}$, $L^{18}$ and $L^{19}$, independently of one another, are H or F;
q is 0, 1, 2, 3 or 4;
p is 0, 1, 2 or 3;
$R^{13}$ and $R^{14}$, independently of one another, are an alkanyl radical having from 1 to 7 carbon atoms or together are an alkylene bridge having from 2 to 7 carbon atoms;
with the proviso that, in the case of direct linking of $Z^{13}$ and $R^{12}$ to give -$Z^{13}$-$R^{12}$, $R^{12}$ is H, aralkyl, alkanyl or alkenyl if $Z^{13}$ is —C(=O)—O— or —C(=O)—, and $Z^{13}$ is not —CH$_2$O— or —CF$_2$O—;

that, in the case of direct linking of $Z^{14}$ and $R^{12}$ to give -$Z^{14}$-$R^{12}$, $R^{12}$ is H, aralkyl, alkanyl or alkenyl if $Z^{14}$ is —C(=O)—O— or —C(=O)—, and $Z^{14}$ is not —CH$_2$O— or —CF$_2$O—;

that, in the case of direct linking of $Z^{15}$ and $R^{12}$ to give -$Z^{15}$-$R^{12}$, $R^{12}$ is H, aralkyl, alkanyl or alkenyl if $Z^{15}$ is —C(=O)—O— or —C(=O)—, and $Z^{15}$ is not —CH$_2$O— or —CF$_2$O—.

On the basis of their properties, the compounds of the formula I according to the invention are used in liquid-crystalline media or serve as starting compounds for the efficient synthesis of further pyran compounds, in particular those having mesogenic properties. They are preferably mesogenic and in particular liquid-crystalline.

In connection with the present invention, the term "alkyl"—unless defined otherwise elsewhere in this description or in the claims—denotes a straight-chain or branched aliphatic hydrocarbon radical having from 1 to 15 (i.e. 1, 2, 3, 4, 5, 6, 7, 8, 9, 10, 11, 12, 13, 14 or 15) carbon atoms; this radical is unsubstituted or mono- or polysubstituted by identical or different fluorine, chlorine, bromine, iodine and/or cyano radicals.

If this alkyl radical is a saturated radical, it is also referred to as "alkanyl" ($C_aH_{2a+1}$—, where a is an integer from 1 to 15 and one or more hydrogen atoms may be replaced by halogen, in particular fluorine, and/or cyano). Furthermore, the term "alkyl" also covers hydrocarbon radicals which are unsubstituted or correspondingly mono- or polysubstituted by identical or different F, Cl, Br, I and/or —CN radicals and in which one or more CH$_2$ groups may be replaced by —O— ("alkoxy", "oxaalkyl"), —S— ("thioalkyl"), —CH=CH— ("alkenyl"), —C≡C— ("alkynyl"), —CO—O— or —O—CO— in such a way that hetero atoms (O and S) are not linked directly to one another. Alkyl is preferably a straight-chain or branched, unsubstituted or substituted alkanyl, alkenyl or alkoxy radical having 1, 2, 3, 4, 5, 6, 7 or 8 carbon atoms. If alkyl is an alkanyl radical, this is preferably methyl, ethyl, n-propyl, i-propyl, n-butyl, i-butyl, t-butyl, n-pentyl, neopentyl, n-hexyl, n-heptyl, n-octyl; CF$_3$, CHF$_2$, CH$_2$F; CF$_2$CF$_3$. The alkanyl radical is particularly preferably straight-chain and unsubstituted or substituted by F.

Since, in accordance with the invention, one or more CH$_2$ groups in an alkyl radical may be replaced by —O—, the term "alkyl" also covers "alkoxy" or "oxaalkyl" radicals. Alkoxy is taken to mean an O-alkyl radical in which the oxygen atom is bonded directly to the group substituted by the alkoxy radical or to the substituted ring, and alkyl is as defined above; alkyl is preferably then alkanyl or alkenyl. Preferred alkoxy radicals are methoxy, ethoxy, propoxy, butoxy, pentoxy, hexoxy, heptoxy and octoxy, where each of these radicals may also be substituted, preferably by one or more fluorine atoms. Alkoxy is particularly preferably —OCH$_3$, —OC$_2$H$_5$, —O-n-C$_3$H$_7$, —O-n-C$_4$H$_9$, —O-t-C$_4$H$_9$, —OCF$_3$, —OCHF$_2$, —OCH$_2$F or —OCHFCHF$_2$. In connection with the present invention, the term "oxaalkyl" denotes alkyl radicals in which at least one non-terminal CH$_2$ group has been replaced by —O— in such a way that no adjacent hetero atoms (O and S) are present. Oxaalkyl preferably covers straight-chain radicals of the formula —C$_a$H$_{2a+1}$—O—(CH$_2$)$_b$—, where a and b are each, independently of one another, 1, 2, 3, 4, 5, 6, 7, 8, 9 or 10; a is particularly preferably an integer from 1 to 6, and b is 1 or 2.

If one or more CH$_2$ groups in an alkyl radical as defined above have been replaced by sulfur, a "thioalkyl" radical is present. "Thioalkyl" preferably covers a straight-chain radical of the formula —C$_a$H$_{2a+1}$—S—(CH$_2$)$_b$—, where a is 1, 2, 3, 4, 5, 6, 7, 8, 9 or 10, and b is 0, 1, 2, 3, 4, 5, 6, 7, 8, 9 or 10; a is particularly preferably an integer from 1 to 6, and b is 0, 1 or 2. The thio-alkyl radical may likewise be substituted by F, Cl, Br, I and/or —CN and is preferably unsubstituted.

In connection with the present invention, the term "alkenyl" denotes an alkyl radical as defined above in which one or more —CH=CH— groups are present. If two —CH=CH— groups are present in the radical, this may also be referred to as "alkadienyl". An alkenyl radical may contain from 2 to 15 (i.e. 2, 3, 4, 5, 6, 7, 8, 9, 10, 11, 12, 13, 14 or 15) carbon atoms and is branched or preferably straight-chain. The radical is unsubstituted or mono- or polysubstituted by identical or different F, Cl, Br, I and/or CN radicals. Furthermore, one or more CH$_2$ groups may each, independently of one another, be replaced by —O—, —S—, —C≡C—, —CO—O— or —OC—O— in such a way that hetero atoms (O and S) are not bonded directly to one another. If the CH=CH group carries a radical other than hydrogen on the two carbon atoms, for example if it is a non-terminal group, the CH=CH group can exist in two configurations, namely as the E isomer and the Z isomer. In general, the E isomer (trans) is preferred. The alkenyl radical preferably contains 2, 3, 4, 5, 6 or 7 carbon atoms and is vinyl, 1 E-propenyl, 1 E-butenyl, 1 E-pentenyl, 1 E-hexenyl, 1 E-heptenyl, 2-propenyl, 2E-butenyl, 2E-pentenyl, 2E-hexenyl, 2E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl or 6-heptenyl. Particularly preferred alkenyl radicals are vinyl, 1 E-propenyl and 3E-butenyl.

If one or more $CH_2$ groups in an alkyl radical have been replaced by —C C—, an alkynyl radical is present. Replacement of one or more $CH_2$ groups by —CO—O— or —O—CO— is also possible. The following radicals are preferred here: acetoxy, propionyloxy, butyryloxy, pentanoyloxy, hexanoyloxy, acetoxymethyl, propionyloxymethyl, butyryloxymethyl, pentanoyloxymethyl, 2-acetoxyethyl, 2-propionyloxyethyl, 2-butyryloxyethyl, 2-acetoxypropyl, 3-propionyloxypropyl, 4-acetoxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl and 4-(methoxycarbonyl) butyl.

In connection with the present invention, the term "aralkyl" represents an arylalkyl radical, i.e. a radical in which an aryl substituent is linked to an atom, a chain, another radical or a functional group via an alkyl bridge; The term "O-aralkyl" represents an arylalkoxy radical, i.e. a radical in which an arylalkyl substituent is linked to an atom, a chain, another radical or a functional group via an oxygen atom. The term aryl substituent here is taken to mean an aromatic hydrocarbon having from 6 to 18 carbon atoms which is optionally substituted by halogen, $NO_2$, alkanyl and/or alkoxy radicals, in particular a phenyl or naphthyl radical. The alkyl bridge is preferably a saturated hydrocarbon radical, in particular methylene (—$CH_2$—) or ethylene (—$CH_2CH_2$—). Preferred examples of an aralkyl radical are benzyl and phenethyl. Preferred examples of an O-aralkyl radical are O-benzyl (—O—$CH_2$-phenyl), O-phenethyl (—O—$CH_2CH_2$-phenyl) and O-(p-nitrobenzyl).

In accordance with the invention, "alkylene bridge" means an aliphatic hydrocarbon chain which is unbranched or branched and has the formula —$C_nH_{2n}$—, for example —$CH_2CH_2$—, —$CH_2CH_2CH_2$— or —$CH_2C(CH_3)_2CH_2$—.

The term "halogen" represents fluorine, chlorine, bromine or iodine, while a "halogenated" radical or a "halogenated" compound is taken to mean a radical or compound which is mono- or polysubstituted by F, Cl, Br and/or I.

If radicals or substituents of the pyran derivatives according to the invention or the pyran derivatives according to the invention themselves can be in the form of optically active or stereoisomeric radicals, substituents or compounds since they have, for example, a centre of asymmetry, these are also covered by the present invention. It goes without saying here that the pyran derivatives of the general formulae I and IV according to the invention can be in isomerically pure form, for example as pure enantiomers, diastereomers, E or Z isomers, trans or cis isomers, or in the form of a mixture of a plurality of isomers in any desired ratio, for example in the form of a racemate, E/Z isomer mixture or cis/trans isomer mixture.

A preferred class of compounds of the formula I according to the invention is formed by pyran derivatives in which W in the formula I is a carbonyl group, i.e.—C(=O)—. The compounds are then lactones of the general formula I-A:

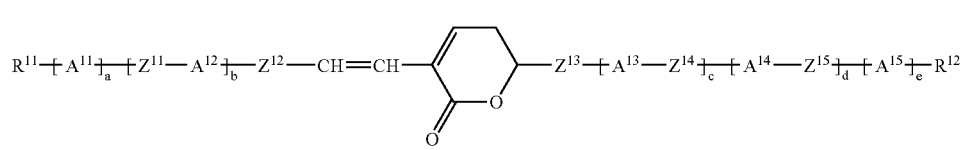

I-A where a, b, c, d, e, $R^{11}$, $R^{12}$, $Z^{11}$, $Z^{12}$, $Z^{13}$, $Z^{14}$, $Z^{15}$, $A^{11}$, $A^{12}$, $A^{13}$, $A^{14}$ and $A^{15}$ are as defined for the formula I above.

Another preferred class of compounds of the formula I according to the invention is formed by pyran derivatives in which W in the formula I is a methylene group, i.e.—$CH_2$—. The compounds are then dihydropyrans of the general formula I-B:

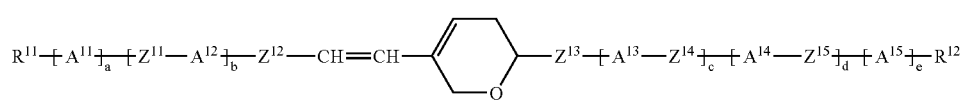

I-B where a, b, c, d, e, $R^{11}$, $R^{12}$, $Z^{11}$, $Z^{12}$, $Z^{13}$, $Z^{14}$, $Z^{15}$, $A^{11}$, $A^{12}$, $A^{13}$, $A^{14}$ and $A^{15}$ are as defined for the formula I above.

In connection with the present invention, the compounds of the formula I according to the invention are also referred to as "pyran derivatives"; the term "pyran derivatives" covers both pyrans of the formula I-B and lactones of the formula I-A.

Preference is furthermore given to compounds of the formula I in which $Z^{12}$ is a single bond. It is furthermore preferred for a+b+c+d+e to be ≦3, i.e. for the compounds of the formula I according to the invention to contain not more than a total of four ring systems. $R^{11}$ is preferably H, a straight-chain alkenyl or in particular alkanyl radical having from 1 to 7 carbon atoms, and $R^{12}$ is preferably halogen, in particular fluorine, or an unbranched alkanyl or alkoxy radical having from 1 to 5 carbon atoms which is optionally mono- or polysubstituted by halogen, in particular fluorine. It is additionally preferred, if $Z^{13}$ is $CF_2O$, for the difluorooxymethylene bridge to be bonded to an aromatic ring $A^{13}$ (c=1), $A^{14}$ (c=0, d=1) or $A^{15}$ (c=d=0, e=1), i.e. a 1,4-phenylene, 2,6-naphthylene or phenanthrenyl radical, respectively.

A further preferred group of compounds according to the invention includes compounds in which a and b in the formula I are simultaneously zero, $R^{11}$ is H and $Z^{12}$ is a single bond, i.e. pyrans of the formula I-C

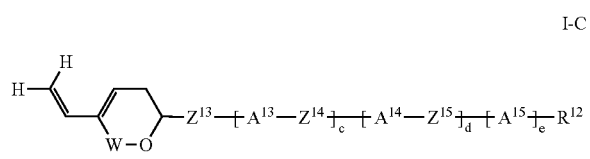

I-C where c, d, e, W, $R^{12}$, $Z^{13}$, $Z^{14}$, $Z^{15}$, $A^{13}$, $A^{14}$ and $A^{15}$ are as defined for the formula I. These compounds are particularly suitable as starting compounds for the preparation of further substances which contain a 2,5-disubstituted pyran ring as a constituent of the molecule; examples which may be mentioned are compounds which can be obtained by reaction of the exocyclic C=C double bond in the 5-position of the pyran ring of a compound of the formula I-C with suitable reactants (see below).

Given a suitable choice of the respective meanings of c, d, e, W, $R^{12}$, $Z^{13}$, $Z^{14}$, $Z^{15}$, $A^{13}$, $A^{14}$ and $A^{15}$, compounds of the formula I-C also have mesogenic properties, and they are consequently used, for example, in liquid-crystalline media for use in, for example, electro-optical display devices.

Preferred sub-groups of compounds of the formula I-C are compounds of the formula I-CA and in particular of the formula I-CB:

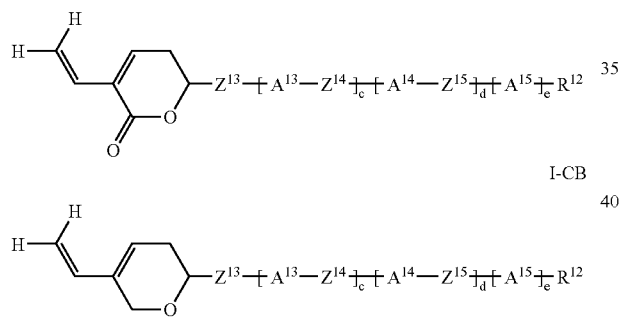

I-CA

I-CB where c, d, e, $R^{12}$, $Z^{13}$, $Z^{14}$, $Z^{15}$, $A^{13}$, $A^{14}$ and $A^{15}$ are as defined for the formula I.

Of the compounds of the formula I-CB, particularly preferred compounds are those of the formulae I-CBI ($Z^{13}$=single bond), I-CBII, I-CBIII, I-CBIV and I-CBV:

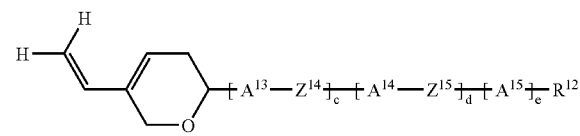

I-CBI

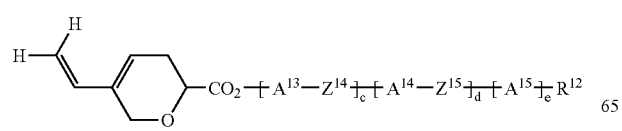

I-CBII

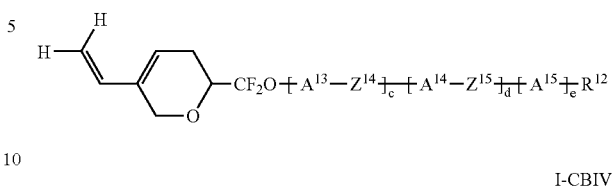

I-CBIII

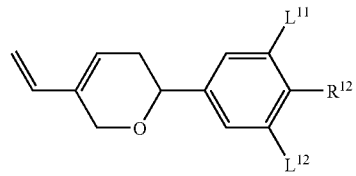

I-CBIV

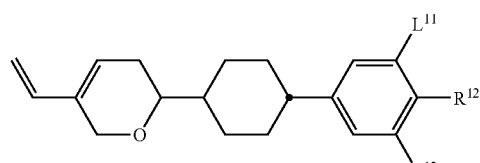

I-CBV in which c, d, e, $R^{12}$, $Z^{14}$, $Z^{15}$, $A^{13}$, $A^{14}$ and $A^{15}$ are as defined for the formula I.

Very particularly preferred compounds of the general formula I-CBI are those of the formulae I-CBIa, I-CBIb, I-CBIc, I-CBId, I-CBIe, I-CBIf, I-CBIg, I-CBIh, I-CBIi, I-CBIj, I-CBIk, I-CBIm and I-CBIn:

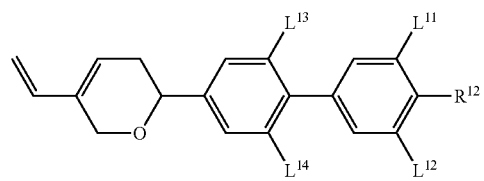

I-CBIa

I-CBIb

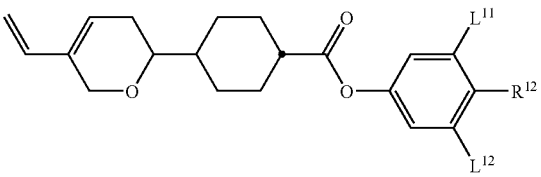

I-CBIc

I-CBId

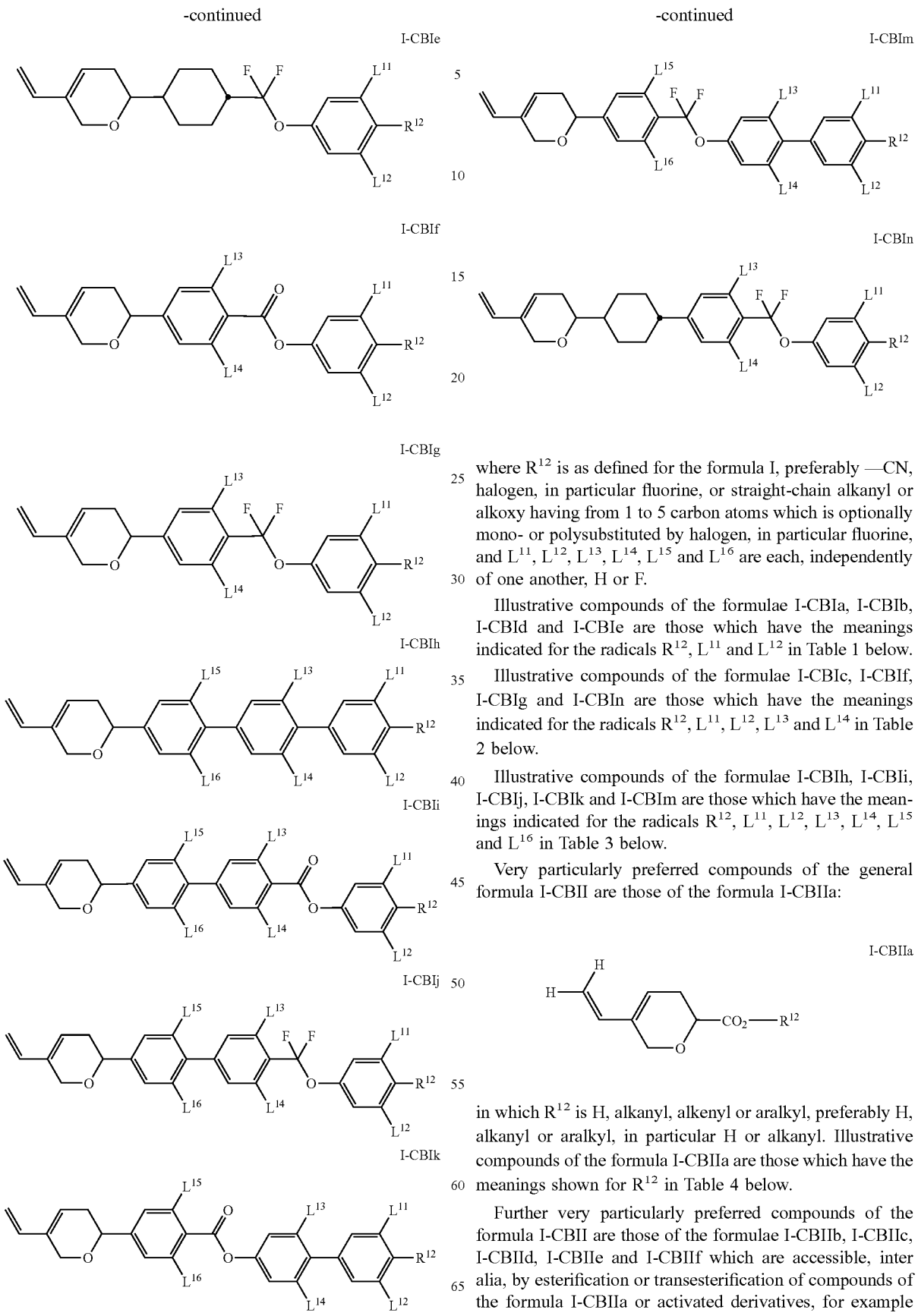

where $R^{12}$ is as defined for the formula I, preferably —CN, halogen, in particular fluorine, or straight-chain alkanyl or alkoxy having from 1 to 5 carbon atoms which is optionally mono- or polysubstituted by halogen, in particular fluorine, and $L^{11}$, $L^{12}$, $L^{13}$, $L^{14}$, $L^{15}$ and $L^{16}$ are each, independently of one another, H or F.

Illustrative compounds of the formulae I-CBIa, I-CBIb, I-CBId and I-CBIe are those which have the meanings indicated for the radicals $R^{12}$, $L^{11}$ and $L^{12}$ in Table 1 below.

Illustrative compounds of the formulae I-CBIc, I-CBIf, I-CBIg and I-CBIn are those which have the meanings indicated for the radicals $R^{12}$, $L^{11}$, $L^{12}$, $L^{13}$ and $L^{14}$ in Table 2 below.

Illustrative compounds of the formulae I-CBIh, I-CBIi, I-CBIj, I-CBIk and I-CBIm are those which have the meanings indicated for the radicals $R^{12}$, $L^{11}$, $L^{12}$, $L^{13}$, $L^{14}$, $L^{15}$ and $L^{16}$ in Table 3 below.

Very particularly preferred compounds of the general formula I-CBII are those of the formula I-CBIIa:

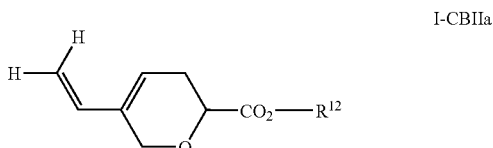

I-CBIIa in which $R^{12}$ is H, alkanyl, alkenyl or aralkyl, preferably H, alkanyl or aralkyl, in particular H or alkanyl. Illustrative compounds of the formula I-CBIIa are those which have the meanings shown for $R^{12}$ in Table 4 below.

Further very particularly preferred compounds of the formula I-CBII are those of the formulae I-CBIIb, I-CBIIc, I-CBIId, I-CBIIe and I-CBIIf which are accessible, inter alia, by esterification or transesterification of compounds of the formula I-CBIIa or activated derivatives, for example carbonyl halides, using the corresponding alcohols:

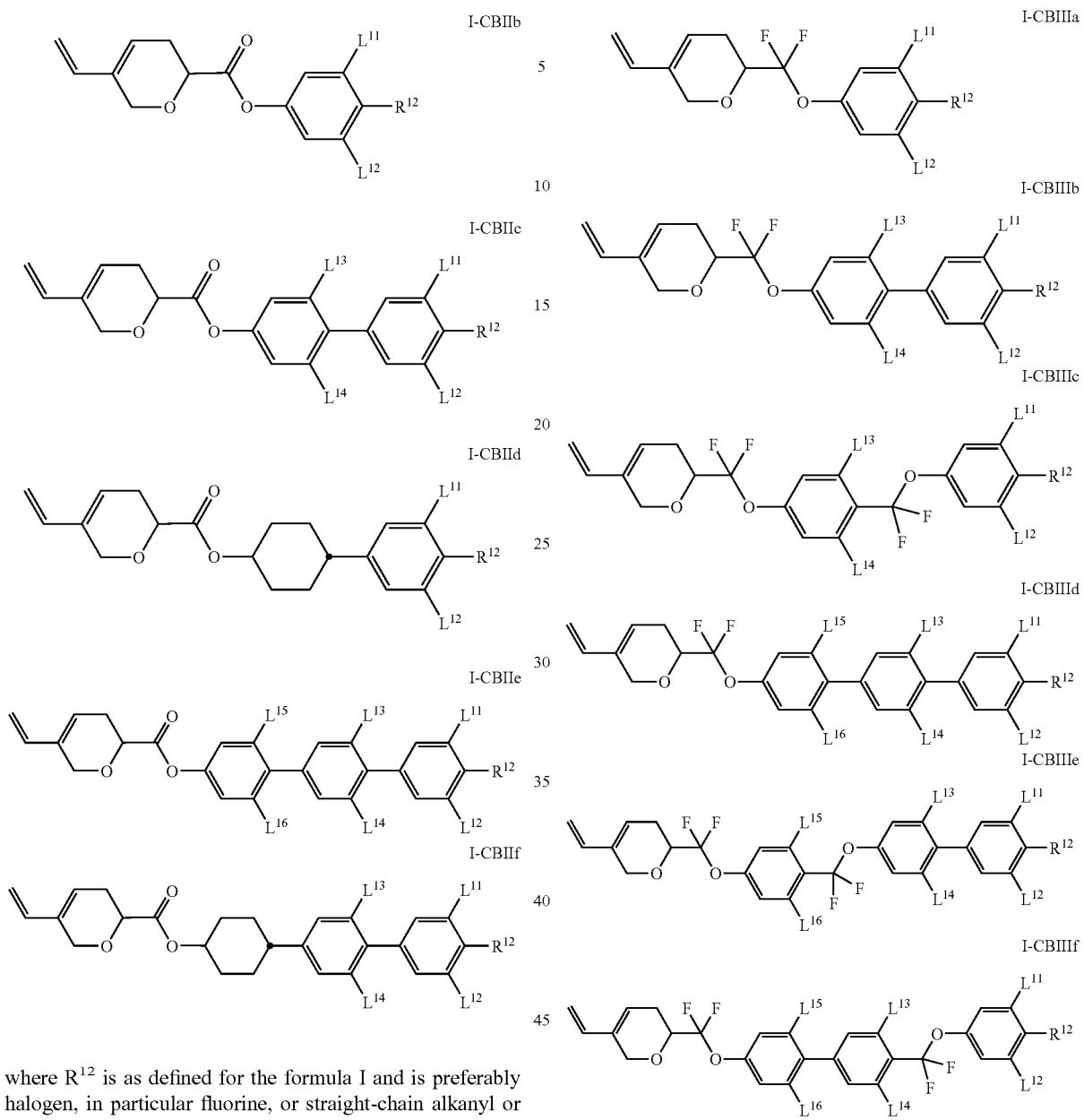

where $R^{12}$ is as defined for the formula I and is preferably halogen, in particular fluorine, or straight-chain alkanyl or alkoxy having from 1 to 5 carbon atoms which is optionally mono- or polysubstituted by halogen, in particular fluorine, while $L^{11}$, $L^{12}$, $L^{13}$, $L^{14}$, $L^{15}$ and $L^{16}$ are each, independently of one another, H or F.

Illustrative compounds of the formulae I-CBIIb and I-CBIId are those which have the meanings indicated for the radicals $R^{12}$, $L^{11}$ and $L^{12}$ in Table 1 below.

Illustrative compounds of the formulae I-CBIIc and I-CBIIf are those which have the meanings indicated for the radicals $R^{12}$, $L^{11}$, $L^{12}$, $L^{13}$ and $L^{14}$ in Table 2 below.

Illustrative compounds of the formula I-CBIIe are those which have the meanings indicated for the radicals $R^{12}$, $L^{11}$, $L^{12}$, $L^{13}$, $L^{14}$, $L^{15}$ and $L^{16}$ in Table 3 below.

Very particularly preferred compounds of the formula I-CBIII are those of the formulae I-CBIIIa, I-CBIIIb, I-CBIIIc, I-CBIIId, I-CBIIIe and I-CBIIIf:

where $R^{12}$ is as defined for the formula I and is preferably halogen, in particular fluorine, or straight-chain alkanyl or alkoxy having from 1 to 5 carbon atoms which is optionally mono- or polysubstituted by halogen, in particular fluorine, while $L^{11}$, $L^{12}$, $L^{13}$, $L^{14}$, $L^{15}$ and $L^{16}$ are each, independently of one another, H or F.

Illustrative compounds of the formula I-CBIIa are those which have the meanings indicated for the radicals $R^{12}$, $L^{11}$ and $L^{12}$ in Table 1 below.

TABLE 1

| I-CBIa/I-CBIb/I-CBId/I-CBIe/<br>I-CBIIb/I-CBIId/I-CBIIIa No. | $L^{11}$ | $L^{12}$ | $R^{12}$ |
| --- | --- | --- | --- |
| 1 | H | H | F |
| 2 | H | H | $CF_3$ |

TABLE 1-continued

| I-CBIa/I-CBIb/I-CBId/I-CBIe/<br>I-CBIIb/I-CBIId/I-CBIIIa No. | $L^{11}$ | $L^{12}$ | $R^{12}$ |
|---|---|---|---|
| 3 | H | H | $OCF_3$ |
| 4 | H | H | $OCHF_2$ |
| 5 | H | H | CN |
| 6 | F | H | F |
| 7 | F | H | $CF_3$ |
| 8 | F | H | $OCF_3$ |
| 9 | F | H | $OCHF_2$ |
| 10 | F | H | CN |
| 11 | F | F | F |
| 12 | F | F | $CF_3$ |
| 13 | F | F | $OCF_3$ |
| 14 | F | F | $OCHF_2$ |
| 15 | F | F | CN |

Illustrative compounds of the formulae I-CBIIIb and I-CBIIIc are those which have the meanings indicated for the radicals $R^{12}$, $L^{11}$, $L^{12}$, $L^{13}$ and $L^{14}$ in Table 2 below.

TABLE 2

| I-CBIc/I-CBIf/I-CBIg/I-CBIn/I-CBIIc/<br>I-CBIIf/I-CBIIIb/I-CBIIIc No. | $L^{13}$ | $L^{14}$ | $L^{11}$ | $L^{12}$ | $R^{12}$ |
|---|---|---|---|---|---|
| 1 | H | H | H | H | F |
| 2 | H | H | H | H | $CF_3$ |
| 3 | H | H | H | H | $OCF_3$ |
| 4 | H | H | H | H | $OCHF_2$ |
| 5 | H | H | H | H | CN |
| 6 | H | H | H | F | F |
| 7 | H | H | H | F | $CF_3$ |
| 8 | H | H | H | F | $OCF_3$ |
| 9 | H | H | H | F | $OCHF_2$ |
| 10 | H | H | H | F | CN |
| 11 | H | H | F | F | F |
| 12 | H | H | F | F | $CF_3$ |
| 13 | H | H | F | F | $OCF_3$ |
| 14 | H | H | F | F | $OCHF_2$ |
| 15 | H | H | F | F | CN |
| 16 | H | F | F | F | F |
| 17 | H | F | F | F | $CF_3$ |
| 18 | H | F | F | F | $OCF_3$ |
| 19 | H | F | F | F | $OCHF_2$ |
| 20 | H | F | F | F | CN |
| 21 | F | F | F | F | F |
| 22 | F | F | F | F | $CF_3$ |
| 23 | F | F | F | F | $OCF_3$ |
| 24 | F | F | F | F | $OCHF_2$ |
| 25 | F | F | F | F | CN |
| 26 | F | H | F | H | F |
| 27 | F | H | F | H | $CF_3$ |
| 28 | F | H | F | H | $OCF_3$ |
| 29 | F | H | F | H | $OCHF_2$ |
| 30 | F | H | F | H | CN |

Illustrative compounds of the formulae I-CBIIId, I-CBIIIe and I-CBIIIf are those which have the meanings indicated for the radicals $R^{12}$, $L^{11}$, $L^{12}$, $L^{13}$, $L^{14}$, $L^{15}$ and $L^{16}$ in Table 3 below.

TABLE 3

| I-CBIh/I-CBIi/I-CBIj/I-CBIk/<br>I-CBIm/I-CBIIe/<br>I-CBIIId/I-CBIIIe/ICBIIIf No. | $L^{15}$ | $L^{16}$ | $L^{13}$ | $L^{14}$ | $L^{11}$ | $L^{12}$ | $R^{12}$ |
|---|---|---|---|---|---|---|---|
| 1 | H | H | H | H | H | H | F |
| 2 | H | H | H | H | H | H | $CF_3$ |
| 3 | H | H | H | H | H | H | $OCF_3$ |
| 4 | H | H | H | H | H | H | $OCHF_2$ |
| 5 | H | H | H | H | H | H | CN |
| 6 | H | H | H | H | F | H | F |
| 7 | H | H | H | H | F | H | $CF_3$ |
| 8 | H | H | H | H | F | H | $OCF_3$ |
| 9 | H | H | H | H | F | H | $OCHF_2$ |
| 10 | H | H | H | H | F | H | CN |
| 11 | H | H | H | H | F | F | F |
| 12 | H | H | H | H | F | F | $CF_3$ |
| 13 | H | H | H | H | F | F | $OCF_3$ |
| 14 | H | H | H | H | F | F | $OCHF_2$ |
| 15 | H | H | H | H | F | F | CN |
| 16 | H | H | F | H | F | F | F |
| 17 | H | H | F | H | F | F | $CF_3$ |
| 18 | H | H | F | H | F | F | $OCF_3$ |
| 19 | H | H | F | H | F | F | $OCHF_2$ |
| 20 | H | H | F | H | F | F | CN |
| 21 | H | H | F | F | F | F | F |
| 22 | H | H | F | F | F | F | $CF_3$ |
| 23 | H | H | F | F | F | F | $OCF_3$ |
| 24 | H | H | F | F | F | F | $OCHF_2$ |
| 25 | H | H | F | F | F | F | CN |
| 26 | F | H | F | F | F | F | F |
| 27 | F | H | F | F | F | F | $CF_3$ |
| 28 | F | H | F | F | F | F | $OCF_3$ |
| 29 | F | H | F | F | F | F | $OCHF_2$ |
| 30 | F | H | F | F | F | F | CN |
| 31 | H | H | F | H | F | H | F |
| 32 | H | H | F | H | F | H | $CF_3$ |
| 33 | H | H | F | H | F | H | $OCF_3$ |
| 34 | H | H | F | H | F | H | $OCHF_2$ |
| 35 | H | H | F | H | F | H | CN |

TABLE 4

| I-CBIIa No. | $R^{12}$ |
|---|---|
| 1 | H |
| 2 | $CH_3$ |
| 3 | $C_2H_5$ |
| 4 | $n-C_3H_7$ |
| 5 | $i-C_3H_7$ |
| 6 | $n-C_4H_9$ |
| 7 | $t-C_4H_9$ |
| 8 | $CH_2$-phenyl |
| 9 | $CH_2CH_2$-phenyl |
| 10 | $CH_2$—CH=$CH_2$ |

Very particularly preferred compounds of the formula I-CBIV are those of the formula I-CBIVa:

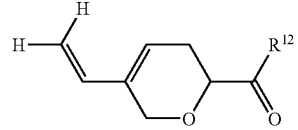

I-CBIVa in which $R^{12}$ is H, alkanyl, alkenyl or aralkyl. Particular preference is given here to the compound I-CBIVa-1 in which $R^{12}$ is H.

A further group of preferred compounds of the present invention are those of the formula I in which $Z^{12}$ is a single bond and—in contrast to the compounds of the formula I-C—the exocyclic C=C double bond in the 5-position of the central pyran ring is bonded via the single bond $Z^{12}$ to a radical which is different from H (formula I-D). This means that the exocyclic CH=CH group linked directly to the central pyran ring is bonded directly either to the cyclohexyl or dioxane ring of group $-Z^{11}-A^{12}$-(if b=1) (formula I-DA) or is bonded directly to the cyclohexyl or dioxane ring $A^{11}$ (if b=0 and a=1) (formula I-DB) or is bonded directly to the radical $R^{11}$ which is not H (if a=b=0) (formula I-DC):

Very particularly preferred compounds of the general formulae I-DABI, I-DABII and I-DABIII are those of the formulae I-DABIa, I-DABIIa and I-DABIIIa:

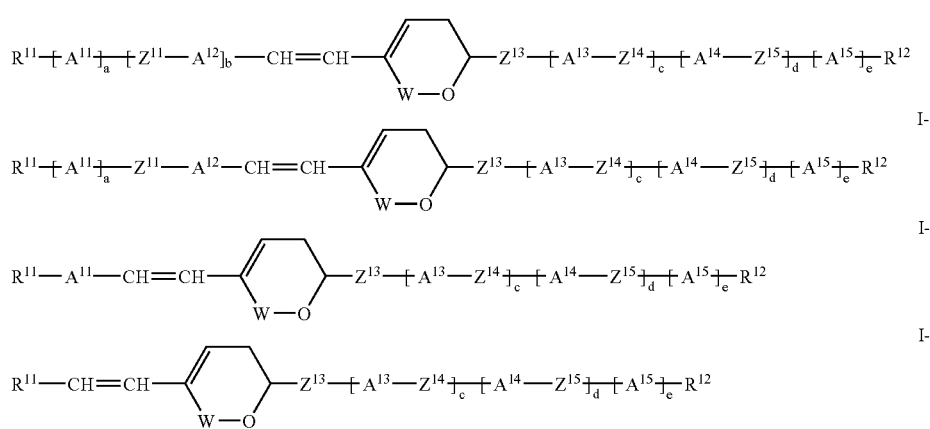

where a, b, c, d, e, W, $R^{11}$, $R^{12}$, $Z^{11}$, $Z^{13}$, $Z^{14}$, $Z^{15}$, $A^{11}$, $A^{12}$, $A^{13}$, $A^{14}$ and $A^{15}$ are otherwise as defined for the formula I above.

Preferred sub-groups of the formula I-DA here are formed by compounds of the formula I-DAA where W=—C(=O)— and in particular by compounds of the formula I-DAB where W=—CH$_2$—:

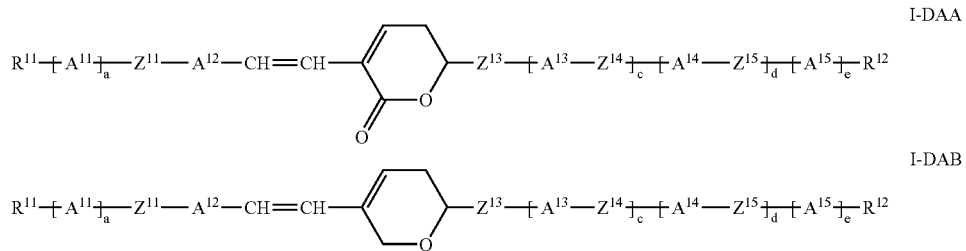

where a, c, d, e, $R^{11}$, $R^{12}$, $Z^{11}$, $Z^{13}$, $Z^{14}$, $Z^{15}$, $A^{11}$, $A^{12}$, $A^{13}$, $A^{14}$ and $A^{15}$ are as defined for the formula I-D above.

Of the compounds of the formula I-DAB, particular preference is given to compounds of the formulae I-DABI, I-DABII and I-DABIII:

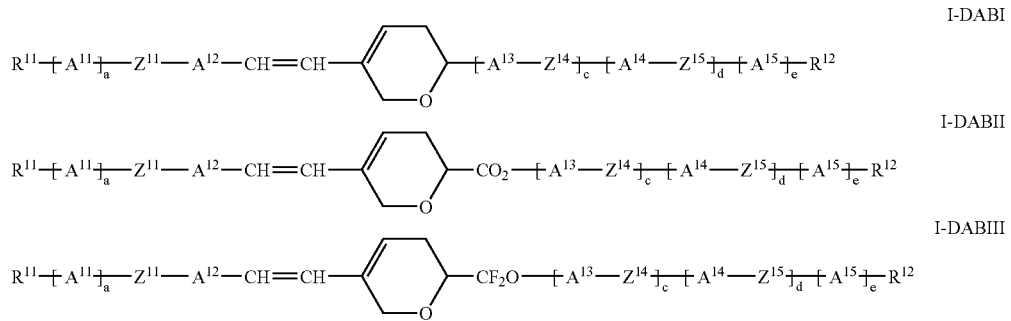

in which a, c, d, e, $R^{11}$, $R^{12}$, $Z^{11}$, $Z^{14}$, $Z^{15}$, $A^{11}$, $A^{12}$, $A^{13}$, $A^{14}$ and $A^{15}$ are as defined for the formula I-D.

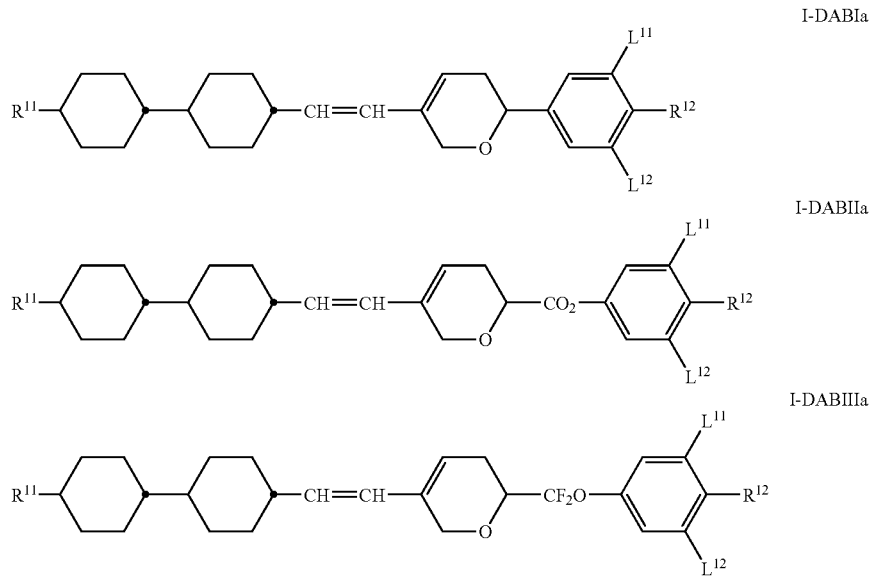

where $R^{11}$ and $R^{12}$ are as defined for the formula I-D, and $L^{11}$ and $L^{12}$ are each, independently of one another, H or F.

Illustrative compounds of the formulae I-DABIa, I-DABIIa and I-DABIIIa are those which have the meanings indicated for the radicals $R^{11}$, $R^{12}$, $L^{11}$ and $L^{12}$ in Table 5 below.

Preferred sub-groups of the formula I-DB are formed by compounds of the formula I-DBA where W=—C(=O)— and in particular by compounds of the formula I-DBB where W=—CH$_2$—:

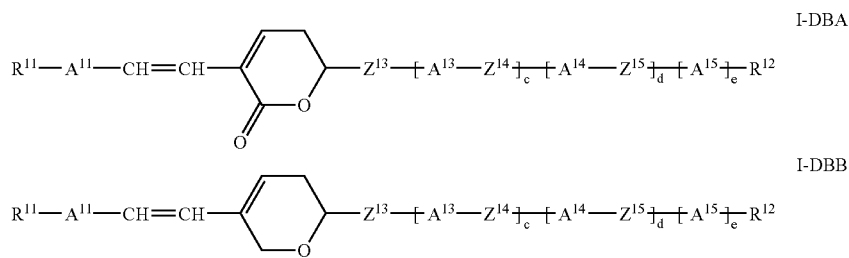

where c, d, e, $R^{11}$, $R^{12}$, $Z^{13}$, $Z^{14}$, $Z^{15}$, $A^{11}$, $A^{13}$, $A^{14}$ and $A^{15}$ are as defined for the formula I-D above.

Of the compounds of the formula I-DBB, particular preference is given to compounds of the formulae I-DBBI, I-DBBII and I-DBBIII:

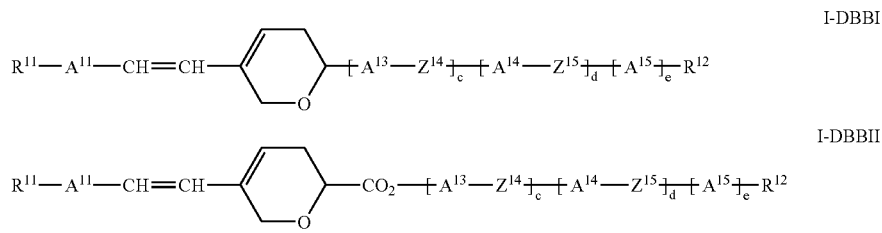

-continued

I-DBBIII

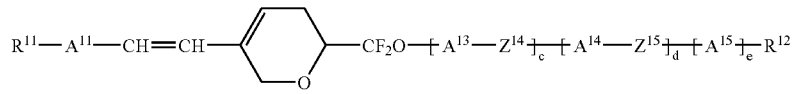

in which c, d, e, $R^{11}$, $R^{12}$, $Z^{14}$, $Z^{15}$, $A^{11}$, $A^{13}$, $A^{14}$ and $A^{15}$ are as defined for the formula I-D. $R^{11}$ is preferably a straight-chain alkenyl or in particular alkanyl radical having from 1 to 7 carbon atoms.

Very particularly preferred compounds of the general formulae I-DBBI, I-DBBII and I-DBBIII are those of the formulae I-DBBIa, I-DBBIb, I-DBBIc, I-DBBId, I-DBBIe, I-DBBIf, I-DBBIg, I-DBBIIa, I-DBBIIb, I-DBBIIIa and I-DBBIIIb:

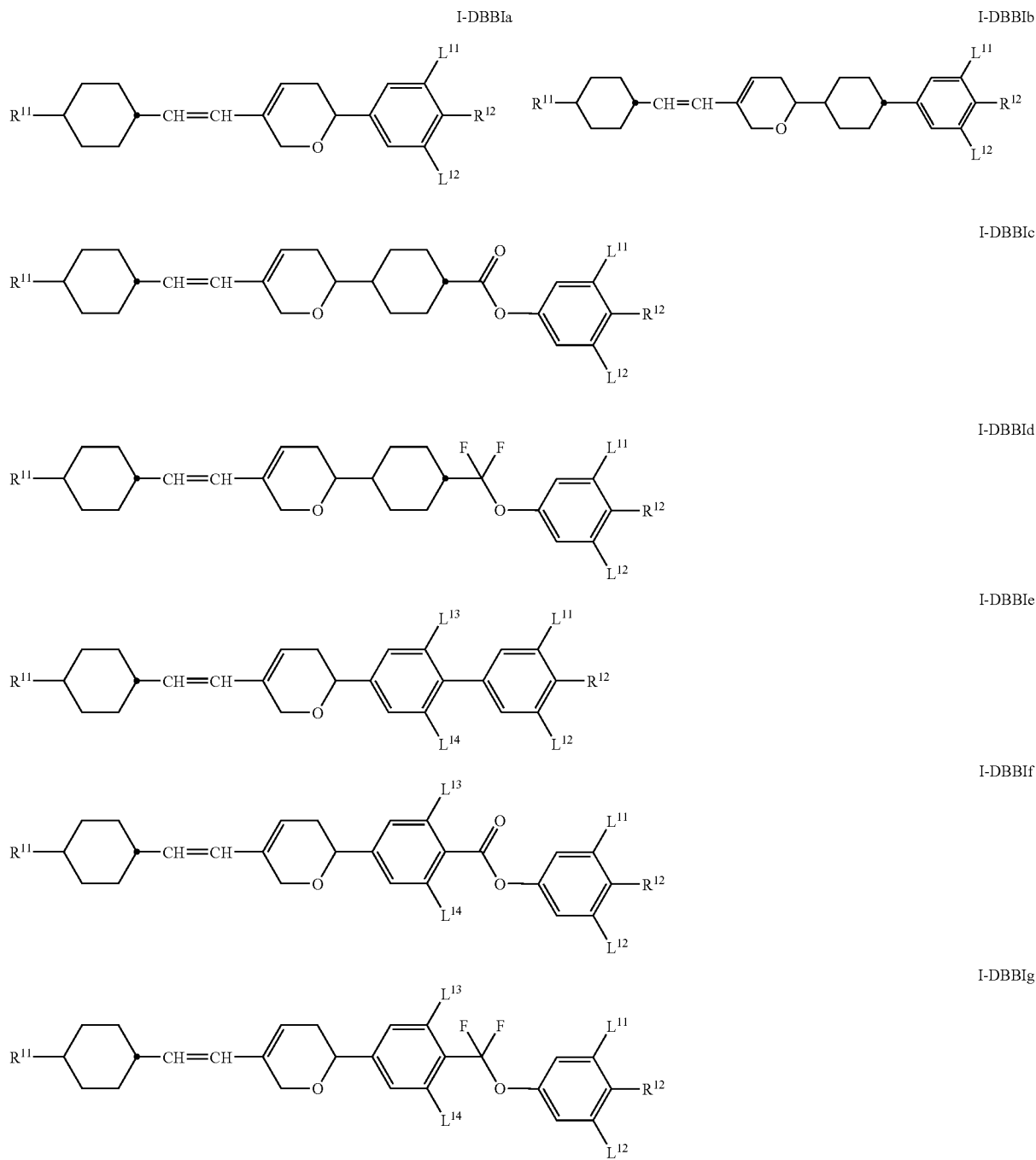

-continued

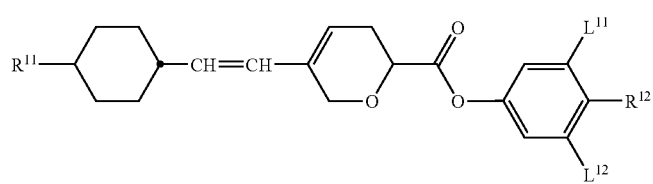
I-DBBIIa

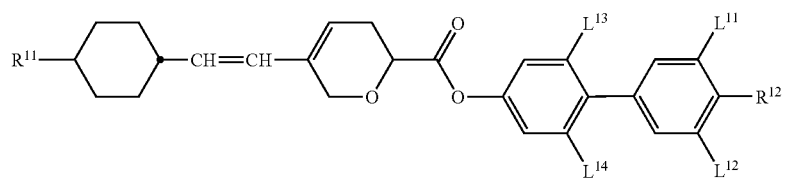
I-DBBIIb

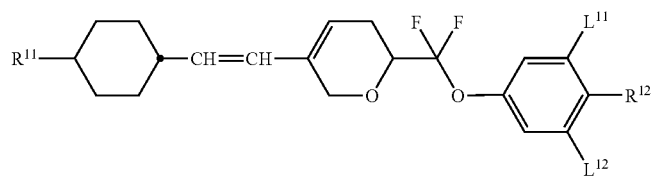
I-DBBIIIa

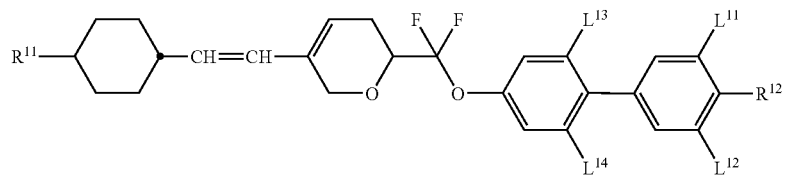
I-DBBIIIb where $R^1$ and $R^{12}$ are as defined for the formula I-D, and $L^{11}$, $L^{12}$, $L^{13}$ and $L^{14}$ are each, independently of one another, H or F. $R^{11}$ is preferably a straight-chain alkenyl or in particular alkanyl radical having from 1 to 7 carbon atoms, and $R^{12}$ is preferably halogen, in particular fluorine, or an unbranched alkanyl or alkoxy radical having from 1 to 5 carbon atoms which is optionally mono- or polysubstituted by halogen, in particular fluorine.

Illustrative compounds of the formulae I-DBBIa, I-DBBIb, I-DBBIc, I-DBBId, I-DBBIIa and I-DBBIIIa are those which have the meanings indicated for the radicals $R^{11}$, $R^{12}$, $L^{11}$ and $L^{12}$ in Table 5 below.

Illustrative compounds of the formulae I-DBBIe, I-DBBIf, I-DBBIg, I-DBBIIb and I-DBBIIIb are those which have the meanings indicated for the radicals $R^{11}$, $R^{12}$, $L^{11}$, $L^{12}$, $L^{13}$ and $L^{14}$ in Table 6 below.

Preferred sub-groups of the formula I-DC are formed by compounds of the formula I-DCA where W=—C(=O)— and in particular by compounds of the formula I-DCB where W=—CH$_2$—:

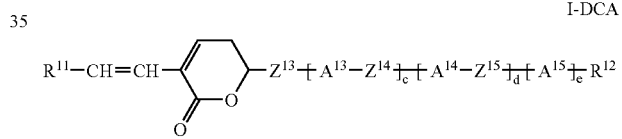
I-DCA

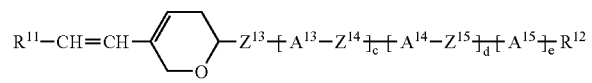
I-DCB where c, d, e, $R^{11}$, $R^{12}$, $Z^{13}$, $Z^{14}$, $Z^{15}$, $A^{13}$, $A^{14}$ and $A^{15}$ are as defined for the formula I-D above.

Of the compounds of the formula I-DCB, particular preference is given to compounds of the formulae I-DCBI, I-DCBII and I-DCBIII:

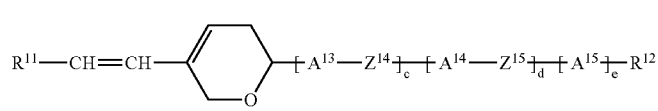
I-DCBI

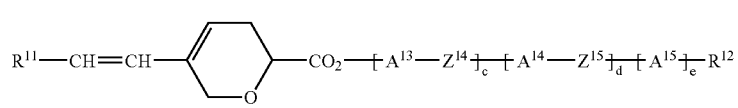
I-DCBII

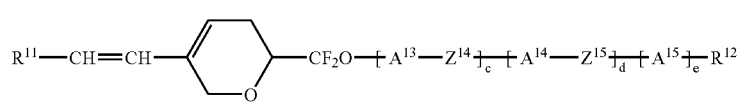
I-DCBIII in which c, d, e, $R^{11}$, $R^{12}$, $Z^{14}$, $Z^{15}$, $A^{13}$, $A^{14}$ and $A^{15}$ are as defined for the formula I-D.

Very particularly preferred compounds of the general formulae I-DCBI, I-DCBII and I-DCBIII are those of the formulae I-DCBIa, I-DCBIb, I-DCBIc, I-DCBId, I-DCBIe, I-DCBIf, I-DCBIg, I-DCBIIa, I-DCBIIb, I-DCBIIc, I-DCBIIIa and I-DCBIIIb:

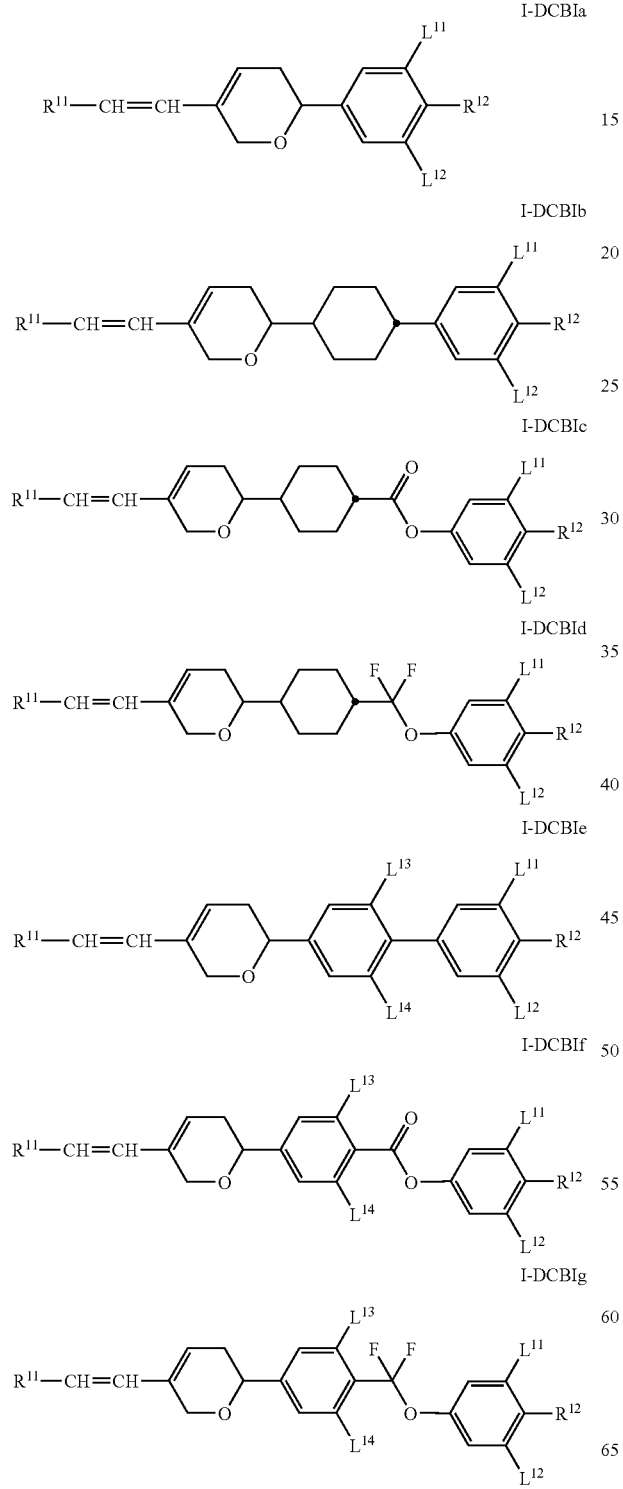

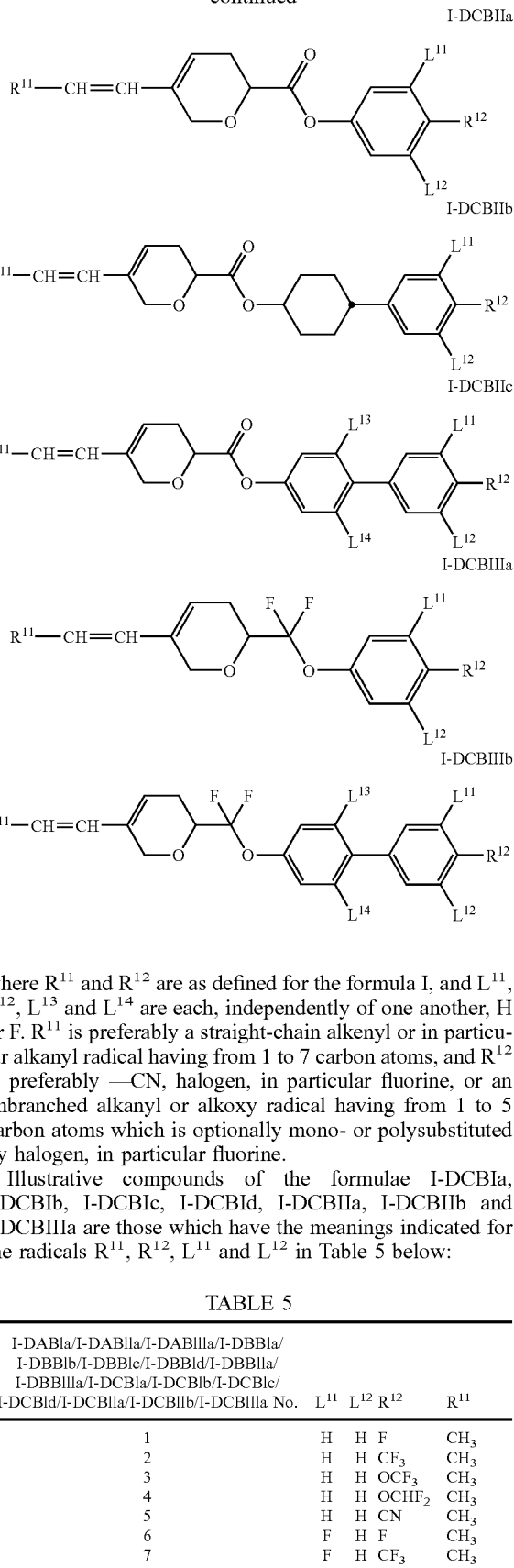

where $R^{11}$ and $R^{12}$ are as defined for the formula I, and $L^{11}$, $L^{12}$, $L^{13}$ and $L^{14}$ are each, independently of one another, H or F. $R^{11}$ is preferably a straight-chain alkenyl or in particular alkanyl radical having from 1 to 7 carbon atoms, and $R^{12}$ is preferably —CN, halogen, in particular fluorine, or an unbranched alkanyl or alkoxy radical having from 1 to 5 carbon atoms which is optionally mono- or polysubstituted by halogen, in particular fluorine.

Illustrative compounds of the formulae I-DCBIa, I-DCBIb, I-DCBIc, I-DCBId, I-DCBIIa, I-DCBIIb and I-DCBIIIa are those which have the meanings indicated for the radicals $R^{11}$, $R^{12}$, $L^{11}$ and $L^{12}$ in Table 5 below:

TABLE 5

| I-DABIa/I-DABIIa/I-DABIIIa/I-DBBIa/ I-DBBIb/I-DBBIc/I-DBBId/I-DBBIIa/ I-DBBIIIa/I-DCBIa/I-DCBIb/I-DCBIc/ I-DCBId/I-DCBIIa/I-DCBIIb/I-DCBIIIa No. | $L^{11}$ | $L^{12}$ | $R^{12}$ | $R^{11}$ |
|---|---|---|---|---|
| 1 | H | H | F | $CH_3$ |
| 2 | H | H | $CF_3$ | $CH_3$ |
| 3 | H | H | $OCF_3$ | $CH_3$ |
| 4 | H | H | $OCHF_2$ | $CH_3$ |
| 5 | H | H | CN | $CH_3$ |
| 6 | F | H | F | $CH_3$ |
| 7 | F | H | $CF_3$ | $CH_3$ |

TABLE 5-continued

I-DABIa/I-DABIIa/I-DABIIIa/I-DBBIa/
I-DBBIb/I-DBBIc/I-DBBId/I-DBBIIa/
I-DBBIIIa/I-DCBIa/I-DCBIb/I-DCBIc/
I-DCBId/I-DCBIIa/I-DCBIIb/I-DCBIIIa No.

| No. | $L^{11}$ | $L^{12}$ | $R^{12}$ | $R^{11}$ |
|---|---|---|---|---|
| 8 | F | H | $OCF_3$ | $CH_3$ |
| 9 | F | H | CN | $CH_3$ |
| 10 | F | H | $OCHF_2$ | $CH_3$ |
| 11 | F | F | F | $CH_3$ |
| 12 | F | F | $CF_3$ | $CH_3$ |
| 13 | F | F | $OCF_3$ | $CH_3$ |
| 14 | F | F | $OCHF_2$ | $CH_3$ |
| 15 | F | F | CN | $CH_3$ |
| 16 | H | H | F | $C_2H_5$ |
| 17 | H | H | $CF_3$ | $C_2H_5$ |
| 18 | H | H | $OCF_3$ | $C_2H_5$ |
| 19 | H | H | $OCHF_2$ | $C_2H_5$ |
| 20 | H | H | CN | $C_2H_5$ |
| 21 | F | H | F | $C_2H_5$ |
| 22 | F | H | $CF_3$ | $C_2H_5$ |
| 23 | F | H | $OCF_3$ | $C_2H_5$ |
| 24 | F | H | $OCHF_2$ | $C_2H_5$ |
| 25 | F | H | CN | $C_2H_5$ |
| 26 | F | F | F | $C_2H_5$ |
| 27 | F | F | $CF_3$ | $C_2H_5$ |
| 28 | F | F | $OCF_3$ | $C_2H_5$ |
| 29 | F | F | $OCHF_2$ | $C_2H_5$ |
| 30 | F | F | CN | $C_2H_5$ |
| 31 | H | H | F | $n\text{-}C_3H_7$ |
| 32 | H | H | $CF_3$ | $n\text{-}C_3H_7$ |
| 33 | H | H | $OCF_3$ | $n\text{-}C_3H_7$ |
| 34 | H | H | $OCHF_2$ | $n\text{-}C_3H_7$ |
| 35 | H | H | CN | $n\text{-}C_3H_7$ |
| 36 | F | H | F | $n\text{-}C_3H_7$ |
| 37 | F | H | $CF_3$ | $n\text{-}C_3H_7$ |
| 38 | F | H | $OCF_3$ | $n\text{-}C_3H_7$ |
| 39 | F | H | $OCHF_2$ | $n\text{-}C_3H_7$ |
| 40 | F | H | CN | $n\text{-}C_3H_7$ |
| 41 | F | F | F | $n\text{-}C_3H_7$ |
| 42 | F | F | $CF_3$ | $n\text{-}C_3H_7$ |
| 43 | F | F | $OCF_3$ | $n\text{-}C_3H_7$ |
| 44 | F | F | $OCHF_2$ | $n\text{-}C_3H_7$ |
| 45 | F | F | CN | $n\text{-}C_3H_7$ |
| 46 | H | H | F | $n\text{-}C_4H_9$ |
| 47 | H | H | $CF_3$ | $n\text{-}C_4H_9$ |
| 48 | H | H | $OCF_3$ | $n\text{-}C_4H_9$ |
| 49 | H | H | $OCHF_2$ | $n\text{-}C_4H_9$ |
| 50 | H | H | CN | $n\text{-}C_4H_9$ |
| 51 | F | H | F | $n\text{-}C_4H_9$ |
| 52 | F | H | $CF_3$ | $n\text{-}C_4H_9$ |
| 53 | F | H | $OCF_3$ | $n\text{-}C_4H_9$ |
| 54 | F | H | $OCHF_2$ | $n\text{-}C_4H_9$ |
| 55 | F | H | CN | $n\text{-}C_4H_9$ |
| 56 | F | F | F | $n\text{-}C_4H_9$ |
| 57 | F | F | $CF_3$ | $n\text{-}C_4H_9$ |
| 58 | F | F | $OCF_3$ | $n\text{-}C_4H_9$ |
| 59 | F | F | $OCHF_2$ | $n\text{-}C_4H_9$ |
| 60 | F | F | CN | $n\text{-}C_4H_9$ |
| 61 | H | H | F | $n\text{-}C_5H_{11}$ |
| 62 | H | H | $CF_3$ | $n\text{-}C_5H_{11}$ |
| 63 | H | H | $OCF_3$ | $n\text{-}C_5H_{11}$ |
| 64 | H | H | $OCHF_2$ | $n\text{-}C_5H_{11}$ |
| 65 | H | H | CN | $n\text{-}C_5H_{11}$ |
| 66 | F | H | F | $n\text{-}C_5H_{11}$ |
| 67 | F | H | $CF_3$ | $n\text{-}C_5H_{11}$ |
| 68 | F | H | $OCF_3$ | $n\text{-}C_5H_{11}$ |
| 69 | F | H | $OCHF_2$ | $n\text{-}C_5H_{11}$ |
| 70 | F | H | CN | $n\text{-}C_5H_{11}$ |
| 71 | F | F | F | $n\text{-}C_5H_{11}$ |
| 72 | F | F | $CF_3$ | $n\text{-}C_5H_{11}$ |
| 73 | F | F | $OCF_3$ | $n\text{-}C_5H_{11}$ |
| 74 | F | F | $OCHF_2$ | $n\text{-}C_5H_{11}$ |
| 75 | F | F | CN | $n\text{-}C_5H_{11}$ |

Illustrative compounds of the formulae I-DCBIe, I-DCBIf, I-DCBIg, I-DCBIIc and I-DCBIIIb are those which have the meanings indicated for the radicals $R^{11}$, $R^{12}$, $L^{11}$, $L^{12}$, $L^{13}$ and $L^{14}$ in Table 6 below:

TABLE 6

I-DBBIe/I-DBBIf/I-DBBIg/I-DBBIIb/I-DBBIIIb/I-DCBIe/
I-DCBIf/I-DCBIg/I-DCBIIc/I-DCBIIIb

| No. | $L^{11}$ | $L^{12}$ | $L^{13}$ | $L^{14}$ | $R^{12}$ | $R^{11}$ |
|---|---|---|---|---|---|---|
| 1 | H | H | H | H | F | $CH_3$ |
| 2 | H | H | H | H | $CF_3$ | $CH_3$ |
| 3 | H | H | H | H | $OCF_3$ | $CH_3$ |
| 4 | H | H | H | H | $OCHF_2$ | $CH_3$ |
| 5 | H | H | H | H | CN | $CH_3$ |
| 6 | F | H | H | H | F | $CH_3$ |
| 7 | F | H | H | H | $CF_3$ | $CH_3$ |
| 8 | F | H | H | H | $OCF_3$ | $CH_3$ |
| 9 | F | H | H | H | $OCHF_2$ | $CH_3$ |
| 10 | F | H | H | H | CN | $CH_3$ |
| 11 | F | F | H | H | F | $CH_3$ |
| 12 | F | F | H | H | $CF_3$ | $CH_3$ |
| 13 | F | F | H | H | $OCF_3$ | $CH_3$ |
| 14 | F | F | H | H | $OCHF_2$ | $CH_3$ |
| 15 | F | F | H | H | CN | $CH_3$ |
| 16 | H | H | H | H | F | $C_2H_5$ |
| 17 | H | H | H | H | $CF_3$ | $C_2H_5$ |
| 18 | H | H | H | H | $OCF_3$ | $C_2H_5$ |
| 19 | H | H | H | H | $OCHF_2$ | $C_2H_5$ |
| 20 | H | H | H | H | CN | $C_2H_5$ |
| 21 | F | H | H | H | F | $C_2H_5$ |
| 22 | F | H | H | H | $CF_3$ | $C_2H_5$ |
| 23 | F | H | H | H | $OCF_3$ | $C_2H_5$ |
| 24 | F | H | H | H | $OCHF_2$ | $C_2H_5$ |
| 25 | F | H | H | H | CN | $C_2H_5$ |
| 26 | F | F | H | H | F | $C_2H_5$ |
| 27 | F | F | H | H | $CF_3$ | $C_2H_5$ |
| 28 | F | F | H | H | $OCF_3$ | $C_2H_5$ |
| 29 | F | F | H | H | $OCHF_2$ | $C_2H_5$ |
| 30 | F | F | H | H | CN | $C_2H_5$ |
| 31 | H | H | H | H | F | $n\text{-}C_3H_7$ |
| 32 | H | H | H | H | $CF_3$ | $n\text{-}C_3H_7$ |
| 33 | H | H | H | H | $OCF_3$ | $n\text{-}C_3H_7$ |
| 34 | H | H | H | H | $OCHF_2$ | $n\text{-}C_3H_7$ |
| 35 | H | H | H | H | CN | $n\text{-}C_3H_7$ |
| 36 | F | H | H | H | F | $n\text{-}C_3H_7$ |
| 37 | F | H | H | H | $CF_3$ | $n\text{-}C_3H_7$ |
| 38 | F | H | H | H | $OCF_3$ | $n\text{-}C_3H_7$ |
| 39 | F | H | H | H | $OCHF_2$ | $n\text{-}C_3H_7$ |
| 40 | F | H | H | H | CN | $n\text{-}C_3H_7$ |
| 41 | F | F | H | H | F | $n\text{-}C_3H_7$ |
| 42 | F | F | H | H | $CF_3$ | $n\text{-}C_3H_7$ |
| 43 | F | F | H | H | $OCF_3$ | $n\text{-}C_3H_7$ |
| 44 | F | F | H | H | $OCHF_2$ | $n\text{-}C_3H_7$ |
| 45 | F | F | H | H | CN | $n\text{-}C_3H_7$ |
| 46 | H | H | H | H | F | $n\text{-}C_4H_9$ |
| 47 | H | H | H | H | $CF_3$ | $n\text{-}C_4H_9$ |
| 48 | H | H | H | H | $OCF_3$ | $n\text{-}C_4H_9$ |
| 49 | H | H | H | H | $OCHF_2$ | $n\text{-}C_4H_9$ |
| 50 | H | H | H | H | CN | $n\text{-}C_4H_9$ |
| 51 | F | H | H | H | F | $n\text{-}C_4H_9$ |
| 52 | F | H | H | H | $CF_3$ | $n\text{-}C_4H_9$ |
| 53 | F | H | H | H | $OCF_3$ | $n\text{-}C_4H_9$ |
| 54 | F | H | H | H | $OCHF_2$ | $n\text{-}C_4H_9$ |
| 55 | F | H | H | H | CN | $n\text{-}C_4H_9$ |
| 56 | F | F | H | H | F | $n\text{-}C_4H_9$ |
| 57 | F | F | H | H | $CF_3$ | $n\text{-}C_4H_9$ |
| 58 | F | F | H | H | $OCF_3$ | $n\text{-}C_4H_9$ |
| 59 | F | F | H | H | $OCHF_2$ | $n\text{-}C_4H_9$ |
| 60 | F | F | H | H | CN | $n\text{-}C_4H_9$ |
| 61 | H | H | H | H | F | $n\text{-}C_5H_{11}$ |
| 62 | H | H | H | H | $CF_3$ | $n\text{-}C_5H_{11}$ |
| 63 | H | H | H | H | $OCF_3$ | $n\text{-}C_5H_{11}$ |
| 64 | H | H | H | H | $OCHF_2$ | $n\text{-}C_5H_{11}$ |
| 65 | H | H | H | H | CN | $n\text{-}C_5H_{11}$ |
| 66 | F | H | H | H | F | $n\text{-}C_5H_{11}$ |
| 67 | F | H | H | H | $CF_3$ | $n\text{-}C_5H_{11}$ |
| 68 | F | H | H | H | $OCF_3$ | $n\text{-}C_5H_{11}$ |
| 69 | F | H | H | H | $OCHF_2$ | $n\text{-}C_5H_{11}$ |
| 70 | F | H | H | H | CN | $n\text{-}C_5H_{11}$ |
| 71 | F | F | H | H | F | $n\text{-}C_5H_{11}$ |
| 72 | F | F | H | H | $CF_3$ | $n\text{-}C_5H_{11}$ |
| 73 | F | F | H | H | $OCF_3$ | $n\text{-}C_5H_{11}$ |
| 74 | F | F | H | H | $OCHF_2$ | $n\text{-}C_5H_{11}$ |

TABLE 6-continued

| I-DBBIe/I-DBBIf/I-DBBIg/I-DBBIIb/I-DBBIIIb/I-DCBIe/I-DCBIf/I-DCBIg/I-DCBIIc/I-DCBIIIb No. | $L^{11}$ | $L^{12}$ | $L^{13}$ | $L^{14}$ | $R^{12}$ | $R^{11}$ |
|---|---|---|---|---|---|---|
| 75 | F | F | H | H | CN | n-$C_5H_{11}$ |
| 76 | F | F | F | H | F | $CH_3$ |
| 77 | F | F | F | H | $CF_3$ | $CH_3$ |
| 78 | F | F | F | H | $OCF_3$ | $CH_3$ |
| 79 | F | F | F | H | $OCHF_2$ | $CH_3$ |
| 80 | F | F | F | H | CN | $CH_3$ |
| 81 | F | F | F | H | F | n-$C_3H_7$ |
| 82 | F | F | F | H | $CF_3$ | n-$C_3H_7$ |
| 83 | F | F | F | H | $OCF_3$ | n-$C_3H_7$ |
| 84 | F | F | F | H | $OCHF_2$ | n-$C_3H_7$ |
| 85 | F | F | F | H | CN | n-$C_3H_7$ |
| 86 | F | F | F | H | F | n-$C_5H_{11}$ |
| 87 | F | F | F | H | $CF_3$ | n-$C_5H_{11}$ |
| 88 | F | F | F | H | $OCF_3$ | n-$C_5H_{11}$ |
| 89 | F | F | F | H | $OCHF_2$ | n-$C_5H_{11}$ |
| 90 | F | F | F | H | CN | n-$C_5H_{11}$ |

A further preferred embodiment of the invention covers compounds of the formula I which do not contain an $A^{11}$ ring (a=0) and in which $A^{12}$ is a 1,4-cyclohexylene ring, and $Z^{11}$ is a single bond (b=1) (formula I-E):

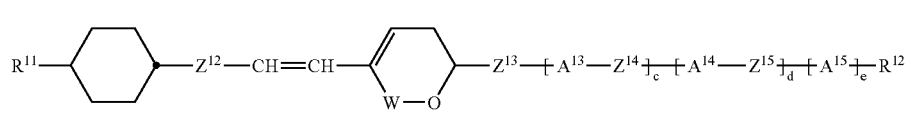

I-E where c, d, e, W, $R^{11}$, $R^{12}$, $Z^{12}$, $Z^{13}$, $Z^{14}$, $Z^{15}$, $A^{13}$, $A^{14}$ and $A^{15}$ are as defined for the formula I above.

Preferred sub-groups of compounds of the formula I-E are compounds of the formula I-EA and in particular of the formula I-EB:

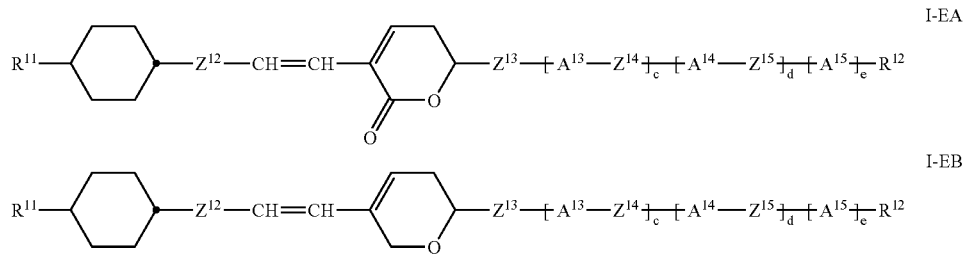

I-EA

I-EB where c, d, e, $R^{11}$, $R^{12}$, $Z^{12}$, $Z^{13}$, $Z^{14}$, $Z^{15}$, $A^{13}$, $A^{14}$ and $A^{15}$ are as defined for the formula I. $R^{11}$ is preferably a straight-chain alkenyl or in particular alkanyl radical having from 1 to 7 carbon atoms, and $R^{12}$ is preferably halogen, in particular fluorine, or an unbranched alkanyl or alkoxy radical having from 1 to 5 carbon atoms which is optionally mono- or polysubstituted by halogen, in particular fluorine.

Particularly preferred compounds of the formula I-EB are those in which $Z^{12}$ is a single bond (formula I-EBI) or a $CH_2CH_2$ group (formula I-EBII):

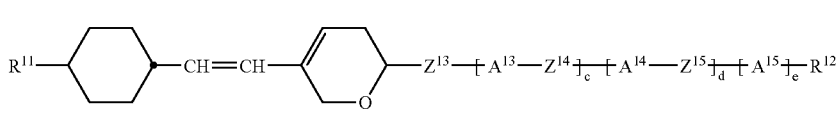

I-EBI

-continued

I-EBII

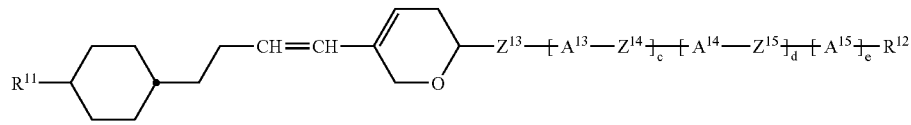

where c, d, e, $R^{11}$, $R^{12}$, $Z^{13}$, $Z^{14}$, $Z^{15}$, $A^{13}$, $A^{14}$ and $A^{15}$ are as defined for the formula I. Illustrative compounds of the formula I-EBI are, inter alia, those of the above-mentioned compounds of the formulae I-DBBIa, I-DBBIb, I-DBBIc, I-DBBId, I-DBBIe, I-DBBIf, I-DBBIg, I-DBBIIa, I-DBBIIb, I-DBBIIIa and I-DBBIIIb.

It is furthermore preferred for $Z^{13}$ in the compounds of the formula I according to the invention to be a single bond (formula I-F), a carboxyl group —C(O)—O— (formula I-G) or a difluorooxymethylene group —CF$_2$O— (formula I-H):

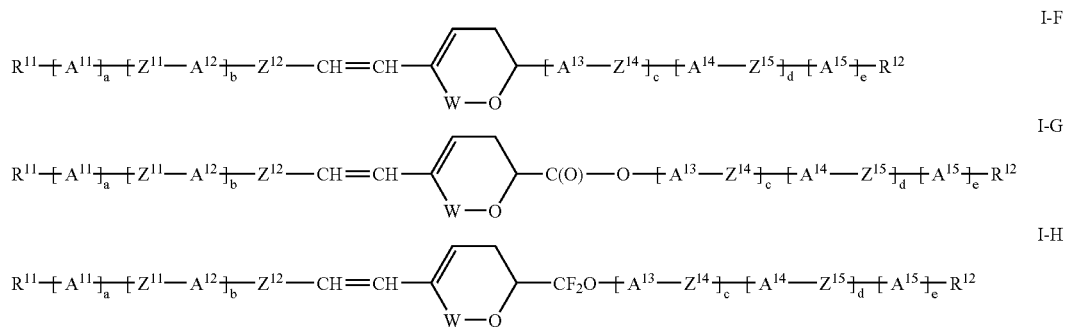

where a, b, c, d, e, W, $R^{11}$, $R^{12}$, $Z^{11}$, $Z^{12}$, $Z^{14}$, $Z^{15}$, $A^{11}$, $A^{12}$, $A^{13}$, $A^{14}$ and $A^{15}$ are as defined for the formula I above.

Preferred sub-groups are formed by compounds of the formulae I-FA, I-FB, I-GA, I-GB, I-HA and I-HB:

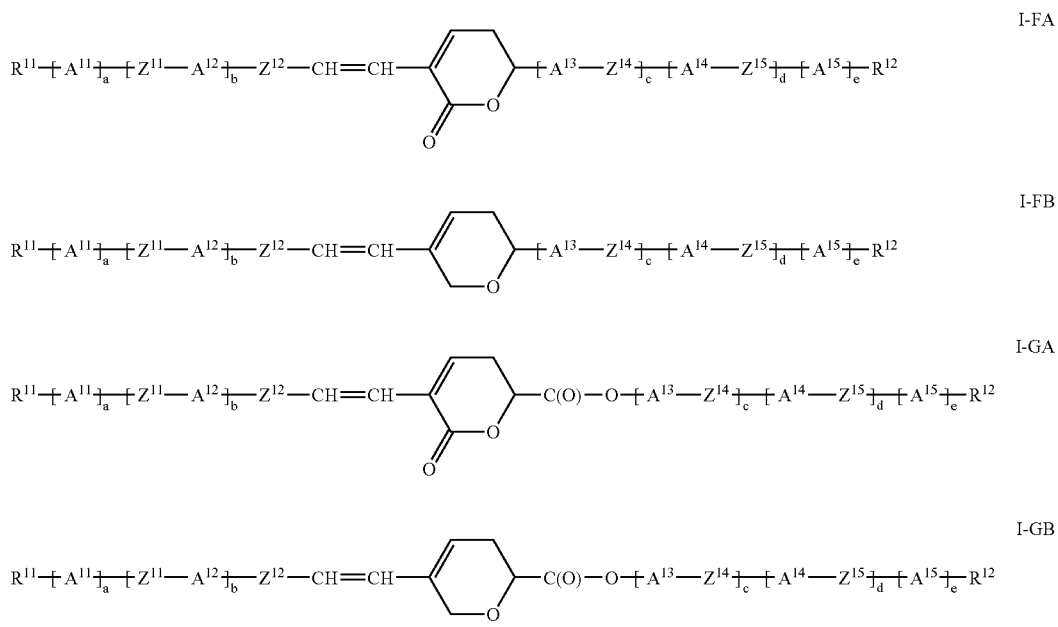

-continued

I-HA

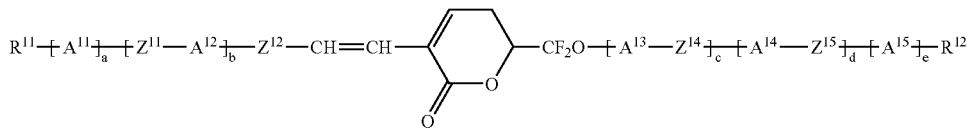

I-HB

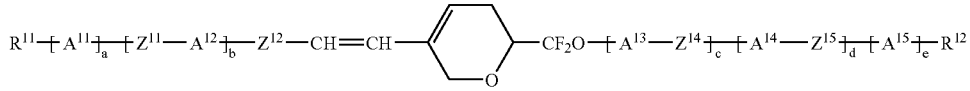

where a, b, c, d, e, $R^{11}$, $R^{12}$, $Z^{11}$, $Z^{12}$, $Z^{14}$, $Z^{15}$, $A^{11}$, $A^{12}$, $A^{13}$, $A^{14}$ and $A^{15}$ as defined for the formula I above. Given a corresponding choice of the meanings of a, b, c, d, e, $R^{11}$, $R^{12}$, $Z^{11}$, $Z^{12}$, $Z^{14}$, $Z^{15}$, $A^{11}$, $A^{12}$, $A^{13}$, $A^{14}$ and $A^{15}$, the compounds of the formulae I-CBI, I-DABI, I-DBBI, I-DCBI and compounds of the formula I-EB where $Z^{13}$=single bond represent some of the preferred compounds of the formula I-FB;

the compounds of the formulae I-CBII, I-DABII, I-DBBII, I-DCBII and compounds of the formula I-EB where $Z^{13}$=—CO—O— represent some of the preferred compounds of the formula I-GB;

the compounds of the formulae I-CBIII, I-DABIII, I-DBBIII, I-DCBIII and compounds of the formula I-EB where $Z^{13}$=$CF_2O$ represent some of the preferred compounds of the formula I-HB.

The preferred compounds of the invention furthermore include pyran derivatives of the formula I which contain no groups $A^{13}$-$Z^{14}$, $A^{14}$-$Z^{15}$ and $A^{15}$ (i.e. c, d and e are simultaneously zero), $Z^{13}$ is a carboxyl radical (C(O)—O) and $R^{12}$ is either H or aralkyl or alkanyl or alkenyl. These carboxylic acids or carboxylic acid esters are illustrated by the formula I-J and at the same time form a preferred group of compounds of the formula I-G:

I-J

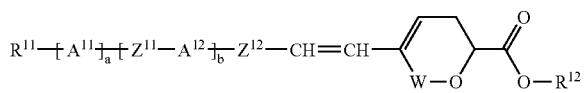

where a, b, W, $R^{11}$, $Z^{11}$, $Z^{12}$, $A^{11}$ and $A^{12}$ are as defined for the formula I above. Preferred sub-groups are formed by compounds of the formulae I-JA and I-JB:

I-JA

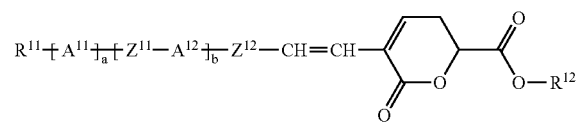

I-JB

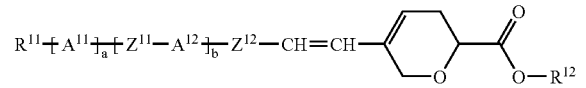

where a, b, $R^{11}$, $R^{12}$, $Z^{11}$, $Z^{12}$, $A^{11}$ and $A^{12}$ are as defined for the formula I above.

Particularly preferred compounds of the formula I-JB are those in which a and b are both simultaneously zero, $Z^{12}$ is a single bond and $R^{11}$ is H, i.e. compounds of the above formula I-CBIIa and compounds of the formulae I-JBI, I-JBII and I-JBIII:

I-JBI

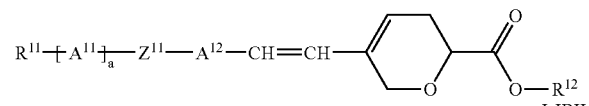

I-JBII

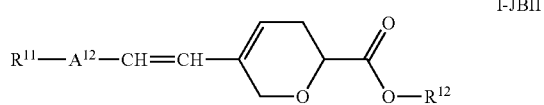

I-JBIII

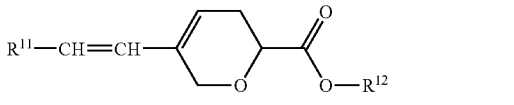

where a, $R^{11}$, $R^{12}$, $Z^{11}$, $Z^{12}$, $A^{11}$ and $A^{12}$ are as defined for the formula I above, but $R^{11}$ in the formula I-JBIII is not H. Besides the compounds of the formulae I-CBIIa and I-JBIII, very particular preference is given to those of the formulae I-JBIa and I-JBIIa:

I-JBIa

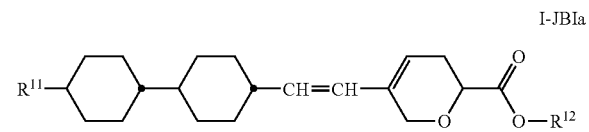

I-JBIIa

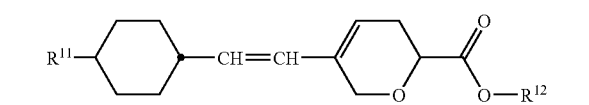

where $R^{11}$ and $R^{12}$ are as defined for the formula I above. Illustrative compounds of the formulae I-JBIa, I-JBIIa and I-JBIII are those which have the meanings indicated for the radicals $R^{11}$ and $R^{12}$ in Table 7 below.

TABLE 7

| I-JBIa/I-JBIIa/I-JBIII No. | $R^{12}$ | $R^{11}$ |
|---|---|---|
| 1 | H | $CH_3$ |
| 2 | H | $C_2H_5$ |
| 3 | H | n-$C_3H_7$ |

TABLE 7-continued

| I-JBIa/I-JBIIa/I-JBIII No. | $R^{12}$ | $R^{11}$ |
|---|---|---|
| 4 | CH$_3$ | CH$_3$ |
| 5 | CH$_3$ | C$_2$H$_5$ |
| 6 | CH$_3$ | n-C$_3$H$_7$ |
| 7 | C$_2$H$_5$ | CH$_3$ |
| 8 | C$_2$H$_5$ | C$_2$H$_5$ |
| 9 | C$_2$H$_5$ | n-C$_3$H$_7$ |
| 10 | n-C$_3$H$_7$ | CH$_3$ |
| 11 | n-C$_3$H$_7$ | C$_2$H$_5$ |
| 12 | n-C$_3$H$_7$ | n-C$_3$H$_7$ |
| 13 | i-C$_3$H$_7$ | CH$_3$ |
| 14 | i-C$_3$H$_7$ | C$_2$H$_5$ |
| 15 | i-C$_3$H$_7$ | n-C$_3$H$_7$ |
| 16 | n-C$_4$H$_9$ | CH$_3$ |
| 17 | n-C$_4$H$_9$ | C$_2$H$_5$ |
| 18 | n-C$_4$H$_9$ | n-C$_3$H$_7$ |
| 19 | t-C$_4$H$_9$ | CH$_3$ |
| 20 | t-C$_4$H$_9$ | C$_2$H$_5$ |
| 21 | t-C$_4$H$_9$ | n-C$_3$H$_7$ |

TABLE 7-continued

| I-JBIa/I-JBIIa/I-JBIII No. | $R^{12}$ | $R^{11}$ |
|---|---|---|
| 22 | CH$_2$-phenyl | CH$_3$ |
| 23 | CH$_2$-phenyl | C$_2$H$_5$ |
| 24 | CH$_2$-phenyl | n-C$_3$H$_7$ |
| 25 | CH$_2$CH$_2$-phenyl | CH$_3$ |
| 26 | CH$_2$CH$_2$-phenyl | C$_2$H$_5$ |
| 27 | CH$_2$CH$_2$-phenyl | n-C$_3$H$_7$ |
| 28 | CH$_2$—CH=CH$_2$ | CH$_3$ |
| 29 | CH$_2$—CH=CH$_2$ | C$_2$H$_5$ |
| 30 | CH$_2$—CH=CH$_2$ | n-C$_3$H$_7$ |

A further preferred embodiment of the invention relates to compounds of the formula I which contain a group $A^{15}$ (e=1) which is a 1,4-phenylene ring which is optionally substituted by fluorine in the 3- and/or 5-position (formula I-K):

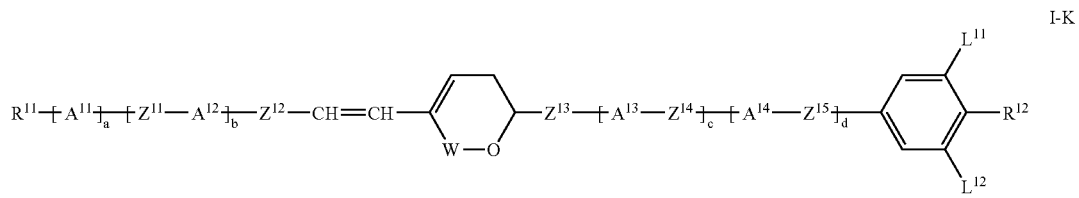

I-K where a, b, c, d, W, $R^{11}$, $R^{12}$, $Z^{11}$, $Z^{12}$, $Z^{13}$, $Z^{14}$, $Z^{15}$, $A^{11}$, $A^{12}$, $A^{13}$, and $A^{14}$ are as defined for the formula I above, and $L^{11}$ and $L^{12}$ are each, independently of one another, H or F.

Preferred sub-groups of compounds of the formula I-K are formed by compounds of the formula I-KA and in particular of the formula I-KB:

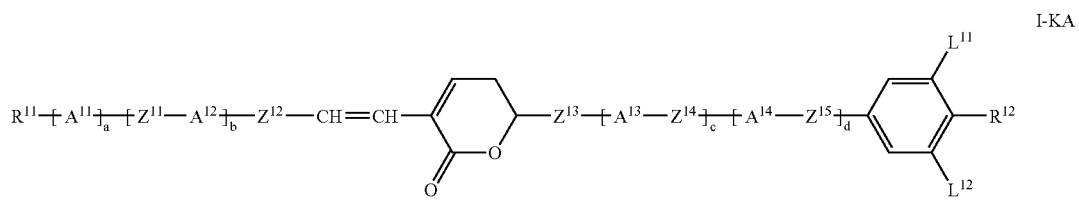

I-KA

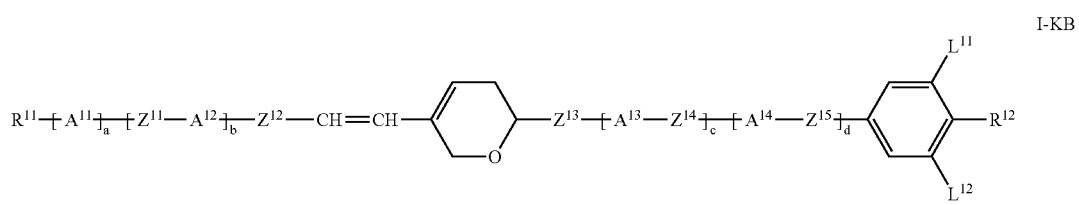

I-KB where a, b, c, d, $R^{11}$, $R^{12}$, $Z^{11}$, $Z^{12}$, $Z^{13}$, $Z^{14}$, $Z^{15}$, $A^{11}$, $A^{12}$, $A^{13}$, and $A^{14}$ are as defined for the formula I, and $L^{11}$ and $L^{12}$ are each, independently of one another, H or F.

Particularly preferred compounds of the formula I-KB are those in which c and d are both simultaneously zero, and $Z^{13}$ is a single bond, —CO—O— or —CF$_2$O— (formulae I-KBA, I-KBB or I-KBC respectively):

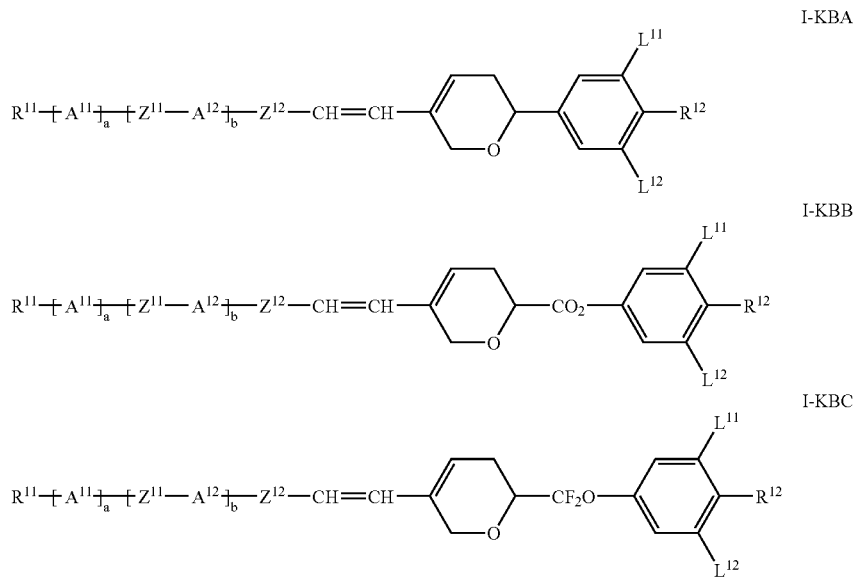

I-KBA

I-KBB

I-KBC where a, b, $R^{11}$, $R^{12}$, $Z^{11}$, $Z^{12}$, $A^{11}$, and $A^{12}$ are as defined for the formula I, and $L^{11}$ and $L^{12}$ are each, independently of one another, H or F. $R^{11}$ is preferably H, a straight-chain alkenyl or in particular alkanyl radical having from 1 to 7 carbon atoms, and $R^{12}$ is preferably halogen, in particular fluorine, or an unbranched alkanyl or alkoxy radical having from 1 to 5 carbon atoms which is optionally mono- or polysubstituted by halogen, in particular fluorine.

Of the compounds of the formula I-KBA, very particular preference is given to those of the formulae I-KBAI, I-KBAII and I-KBAIII:

I-KBAI

I-KBAII

I-KBAIII where a, $R^{11}$, $R^{12}$, $Z^{11}$, $A^{11}$, and $A^{12}$ are as defined for the formula I, and $L^{11}$ and $L^{12}$ are each, independently of one another, H or F. Illustrative compounds of the formulae I-KBAI, I-KBAII and I-KBAIII are, inter alia, the above-mentioned compounds of the formulae I-DABIa, I-DBBIa and I-DCBIa respectively.

Of the compounds of the formula I-KBB, very particular preference is given to those of the formulae I-KBBI, I-KBBII and I-KBBIII:

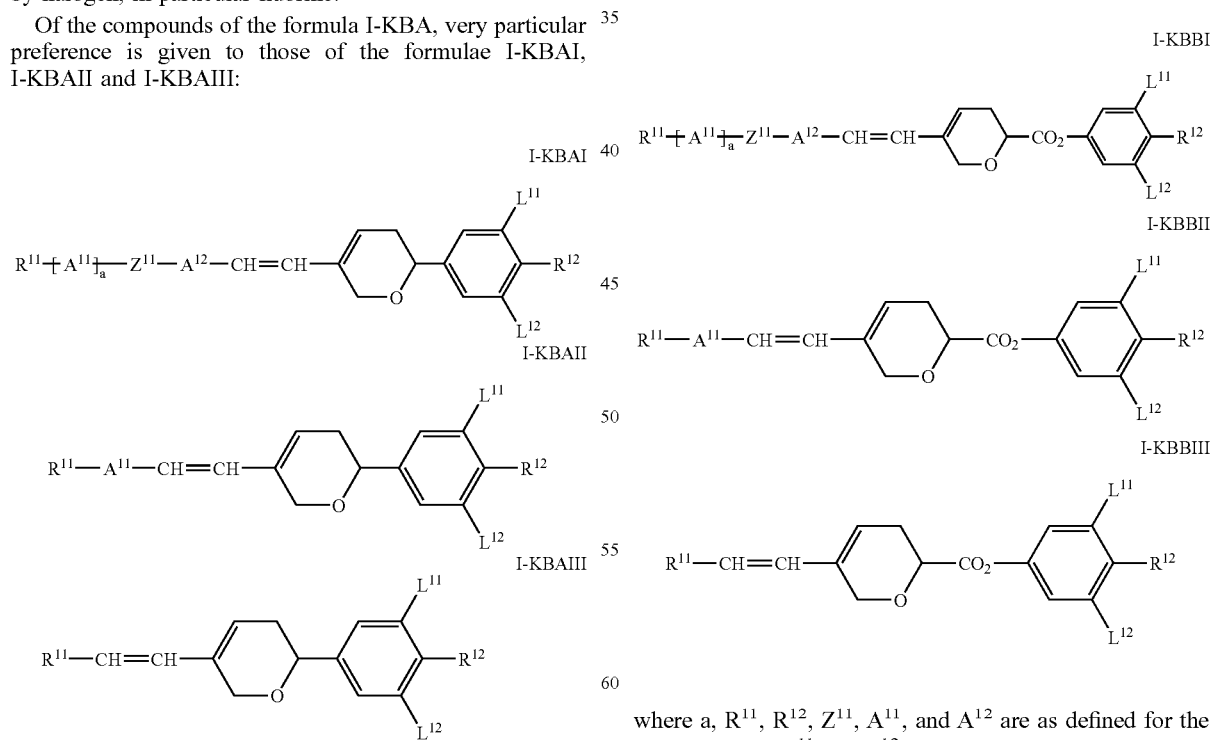

I-KBBI

I-KBBII

I-KBBIII where a, $R^{11}$, $R^{12}$, $Z^{11}$, $A^{11}$, and $A^{12}$ are as defined for the formula I, and $L^{11}$ and $L^{12}$ are each, independently of one another, H or F. Illustrative compounds of the formulae I-KBBI, I-KBBII and I-KBBIII are, inter alia, the above-mentioned compounds of the formulae I-DABIIa, I-DBBIIa and I-DCBIIa respectively.

Of the compounds of the formula I-KBC, very particular preference is given to those of the formulae I-KBCI, I-KBCII and I-KBCIII:

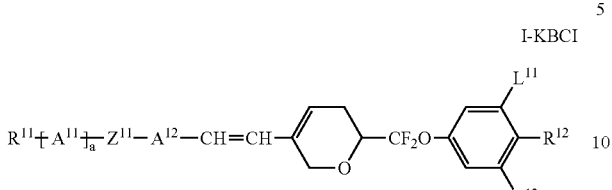
I-KBCI

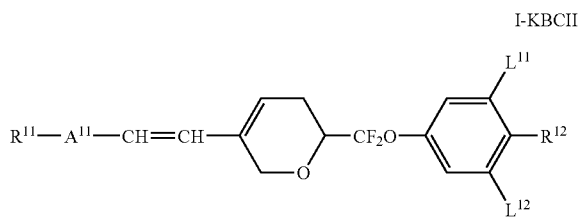
I-KBCII

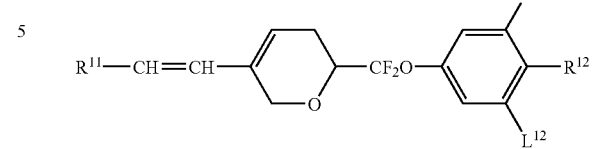
I-KBCIII where a, $R^{11}$, $R^{12}$, $Z^{11}$, $A^{11}$, and $A^{12}$ are as defined for the formula I, and $L^{11}$ and $L^{12}$ are each, independently of one another, H or F. Illustrative compounds of the formulae I-KBCI, I-KBCII and I-KBCIII are, inter alia, the above-mentioned compounds of the formulae I-DABIIIa, I-DB-BIIIa and I-DCBIIIa respectively.

Preference is furthermore given to compounds of the formula I which, besides a ring $A^{15}$, contain a group $A^{13}$-$Z^{14}$ and/or $A^{14}$-$Z^{15}$ (i.e. for which e=1 and c and/or d=1), where $Z^{14}$ and $Z^{15}$, independently of one another, are a single bond or a difluorooxymethylene bridge:

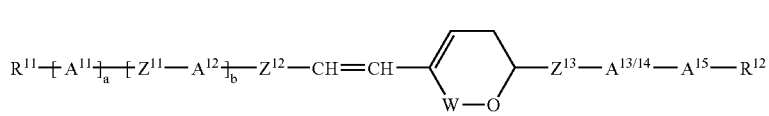
I-L

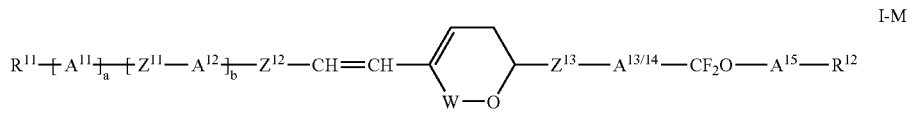
I-M

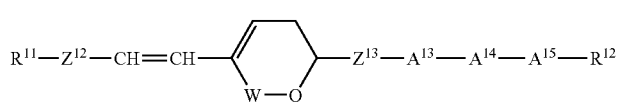
I-N

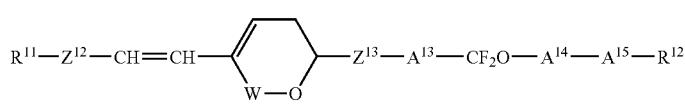
I-O

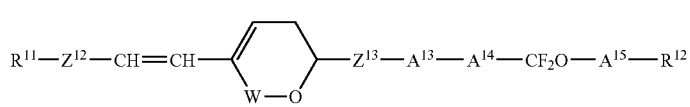
I-P

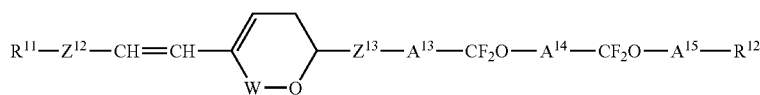
I-Q where a, b, W, $R^{11}$, $R^{12}$, $Z^{11}$, $Z^{12}$, $Z^{13}$, $A^{11}$, $A^{12}$, $A^{13}$, $A^{14}$ and $A^{15}$ are as defined for the formula I above, and $A^{13/14}$ means that either a ring $A^{13}$ or a ring $A^{14}$ is present. It is furthermore preferred for the sum of a, b, c, d and e to be not greater than 3, so that a and b are both zero if—as for the compounds of the formulae I-N, I-O, I-P and I-Q-c=d=e=1.

Preferred sub-groups of the formula I-L are formed by compounds where W=—C(=O)— (formula I-LA) and in particular by compounds where W=—CH$_2$— (formula I-LB).

Particularly preferred compounds of the formula I-LB are compounds of the formulae I-LBA, I-LBB and I-LBC:

I-LBA

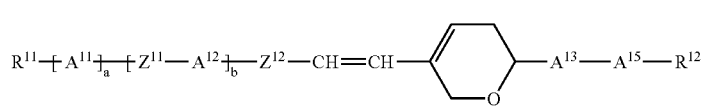

I-LBB

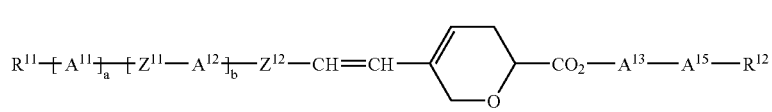

I-LBC

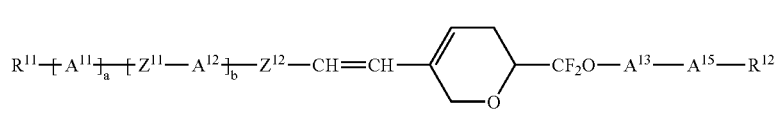

where a, b, $R^{11}$, $R^{12}$, $Z^{11}$, $Z^{12}$, $A^{11}$, $A^{12}$, $A^{13}$ and $A^{15}$ are as defined for the formula I above. $R^{11}$ is preferably H, a straight-chain alkenyl or in particular alkanyl radical having from 1 to 7 carbon atoms, and $R^{12}$ is preferably halogen, in particular fluorine, or an unbranched alkanyl or alkoxy radical having from 1 to 5 carbon atoms which is optionally mono- or polysubstituted by halogen, in particular fluorine. Of these compounds, those of the formulae I-LBAI, I-LBAII, I-LBBI, I-LBBII, I-LBCI and I-LBCII are very particularly preferred:

I-LBAI

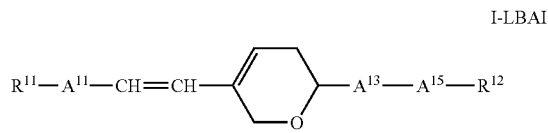

I-LBAII

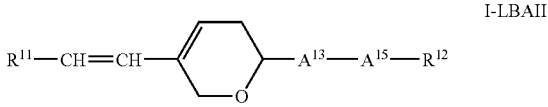

I-LBBI

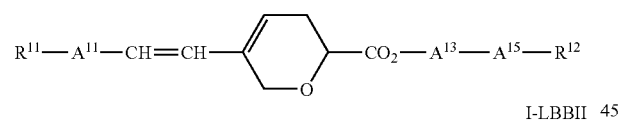

I-LBBII

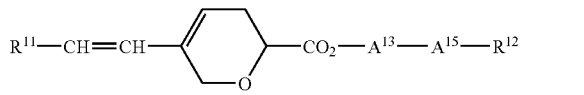

I-LBCI

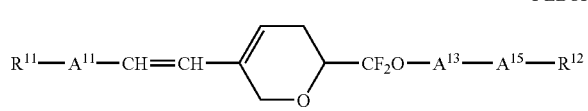

-continued

I-LBCII

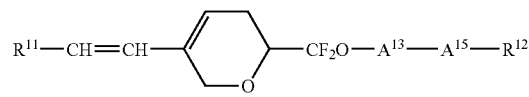

where $R^{11}$, $R^{12}$, $A^{11}$, $A^{13}$ and $A^{15}$ are as defined for the formula I above.

Illustrative compounds of the formula I-LBAI are, inter alia, the above-mentioned compounds of the formulae I-DBBIb and I-DBBIe;

of the formula I-LBAII are, inter alia, the above-mentioned compounds of the formulae I-CBIb, I-CBIc, I-DCBIb, I-DCBIe;

of the formula I-LBBI are, inter alia, the above-mentioned compounds of the formula I-DBBIIb;

of the formula I-LBBII are, inter alia, the above-mentioned compounds of the formulae I-CBIIc, I-CBIId, I-DCBIIb, I-DCBIIc;

of the formula I-LBCI are, inter alia, the above-mentioned compounds of the formula I-DBBIIIb;

of the formula I-LBCII are, inter alia, the above-mentioned compounds of the formulae I-CBIIIb, I-DCBIIIb.

Preferred sub-groups of compounds of the formula I-M are formed by compounds where W=—C(=O)— (formula I-MA) and in particular by compounds where W=—CH$_2$— (formula I-MB).

Particularly preferred compounds of the formula I-MB are compounds of the formulae I-MBA and I-MBB:

I-MBA

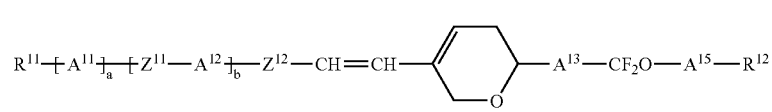

I-MBB

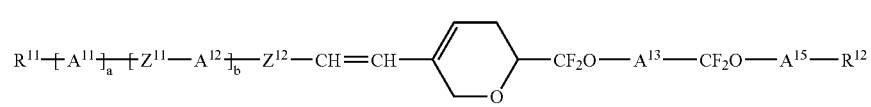

where a, b, $R^{11}$, $R^{12}$, $Z^{11}$, $Z^{12}$, $A^{11}$, $A^{12}$, $A^{13}$ and $A^{15}$ are as defined for the formula I above. $R^{11}$ is preferably hydrogen, a straight-chain alkenyl or in particular alkanyl radical having from 1 to 7 carbon atoms, and $R^{12}$ is preferably halogen, in particular fluorine, an unbranched alkanyl or alkoxy radical having from 1 to 5 carbon atoms which is optionally mono- or polysubstituted by halogen, in particular fluorine. $A^{15}$ in I-MBA and $A^{13}$ and $A^{15}$ in I-MBB are preferably aromatic rings (phenylene and naphthylene respectively). Of these compounds, very particular preference is given to those of the formulae I-MBAI, I-MBAII, I-MBBI and I-MBBII:

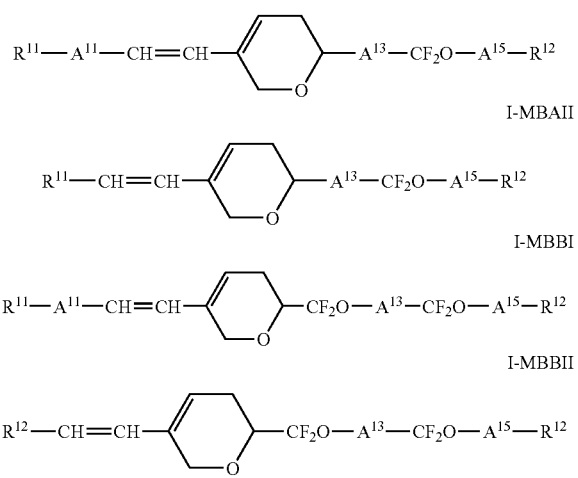

where $R^{11}$, $R^{12}$, $A^{11}$, $A^{13}$ and $A^{15}$ are as defined for the formula I above. Illustrative compounds of the formula I-MBAI are, inter alia, the above-mentioned compounds of the formulae I-DBBId and I-DBBIg, and illustrative compounds of the formula I-MBAII are, inter alia, the above-mentioned compounds of the formulae I-CBIe, I-CBIg, I-DCBId and I-DCBIg. Illustrative compounds of the formula I-MBBI are, inter alia, compounds of the formula I-MBBIa, and illustrative compounds of the formula I-MBBIIa are, inter alia, the above-mentioned compounds of the formula I-CBIIIc and compounds of the formula I-MBBIIa; the radicals $R^{11}$, $R^{12}$, $L^{11}$, $L^{12}$, $L^{13}$ and $L^{14}$ are as defined in Table 8 below.

Preferred sub-groups of compounds of the formula I-N are formed by compounds where W=—C(=O)— (formula I-NA) and in particular by compounds where W=—CH$_2$— (formula I-NB).

Particularly preferred compounds of the formula I-NB are compounds of the formulae I-NBA, I-NBB and I-NBC:

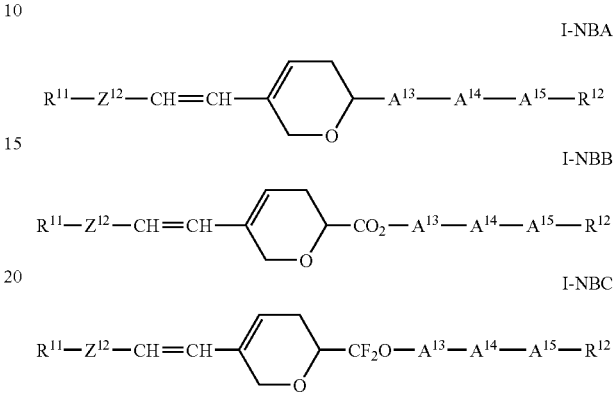

where $R^{11}$, $R^{12}$, $Z^{12}$, $A^{13}$, $A^{14}$ and $A^{15}$ are as defined for the formula I above. $R^{11}$ is preferably H, a straight-chain alkenyl or in particular alkanyl radical having from 1 to 7 carbon atoms, and $R^{12}$ is preferably halogen, in particular fluorine, or an unbranched alkanyl or alkoxy radical having from 1 to 5 carbon atoms which is optionally mono- or polysubstituted by halogen, in particular fluorine. Of these compounds, very particular preference is given to those of the formulae I-NBAI, I-NBBI and I-NBCI:

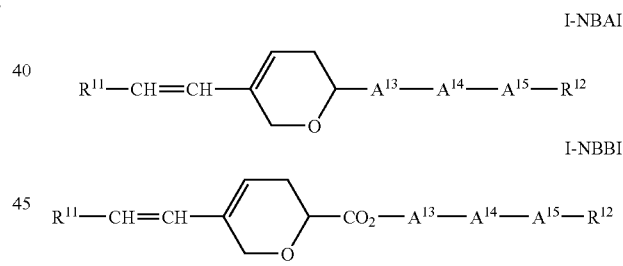

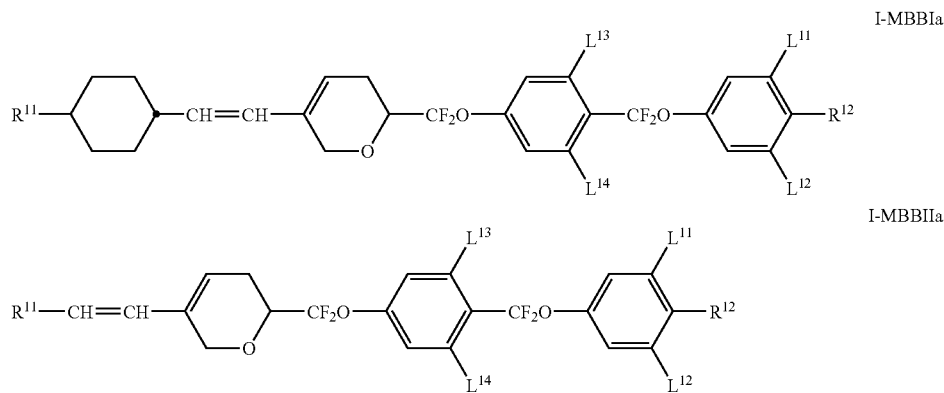

-continued

I-NBCI

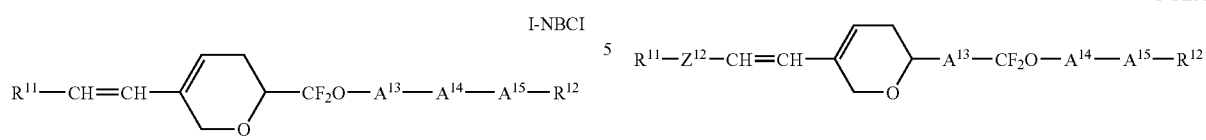

where $R^{11}$, $R^{12}$, $A^{13}$, $A^{14}$ and $A^{15}$ are as defined for the formula I above. Illustrative compounds of the formula I-NBAI are, inter alia, the above-mentioned compounds of the formula I-CBIh and compounds of the formula I-NBAIa; the radicals $R^{11}$, $R^{12}$, $L^{11}$, $L^{12}$, $L^{13}$, $L^{14}$, $L^{15}$ and $L^{16}$ are as defined in Table 9 below. Illustrative compounds of the formula I-NBBI are, inter alia, the above-mentioned compounds of the formulae I-CBIIe and I-CBIIf and compounds of the formulae I-NBBIa and I-NBBIb; the radicals $R^{11}$, $R^{12}$, $L^{11}$, $L^{12}$, $L^{13}$, $L^{14}$, $L^{15}$ and $L^{16}$ are as defined in Table 8 or 9 below. Illustrative compounds of the formula I-NBCI are, inter alia, the above-mentioned compounds of the formula I-CBIIId and compounds of the formula I-NBCIa; the radicals $R^{11}$, $R^{12}$, $L^{11}$, $L^{12}$, $L^{13}$, $L^{14}$, $L^{15}$ and $L^{16}$ are as defined in Table 9 below.

I-OBA

I-OBB

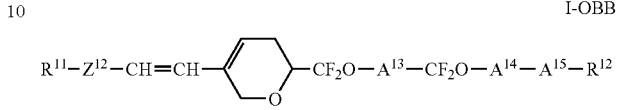

where $R^{11}$, $R^{12}$, $Z^{12}$, $A^{13}$, $A^{14}$ and $A^{15}$ are as defined for the formula I above. $R^{11}$ is preferably H, a straight-chain alkenyl or in particular alkanyl radical having from 1 to 7 carbon atoms, and $R^{12}$ is preferably halogen, in particular fluorine, or an unbranched alkanyl or alkoxy radical having from 1 to 5 carbon atoms which is optionally mono- or polysubstituted by halogen, in particular fluorine. Of these compounds, those of the formulae I-OBAI and I-OBBI are very particularly preferred:

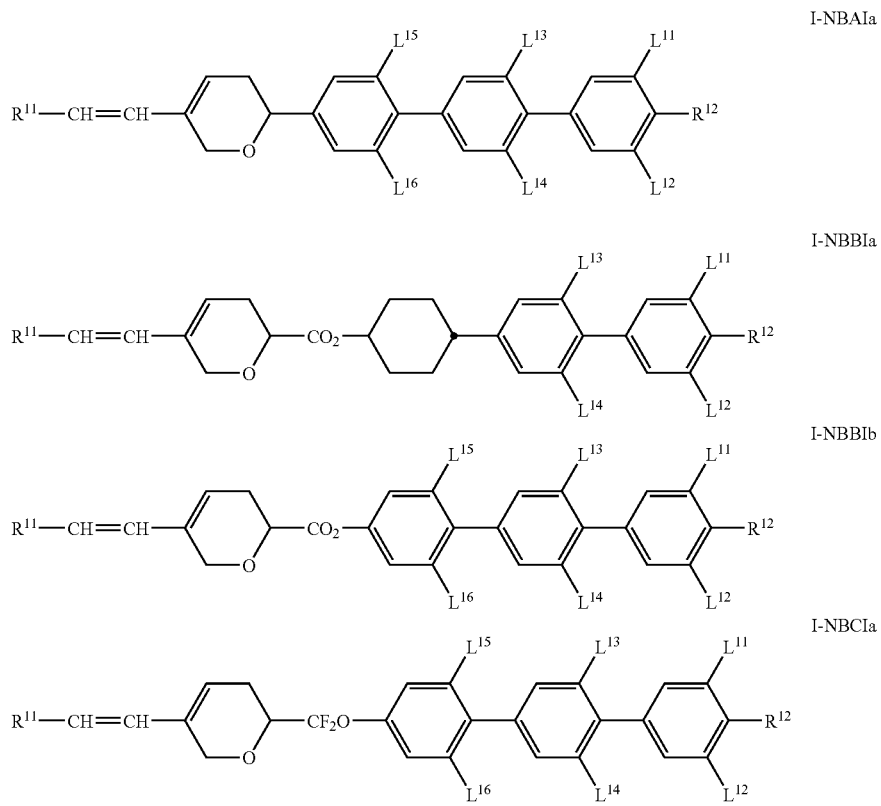

Preferred sub-groups of the formula I-O are formed by compounds where
W=—C(=O)— (formula I-OA) and in particular by compounds where
W=—CH$_2$— (formula I-OB).
Particularly preferred compounds of the formula I-OB are compounds of the formulae I-OBA and I-OBB:

I-OBAI

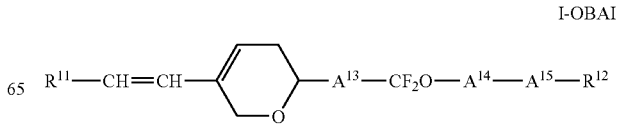

I-OBBI

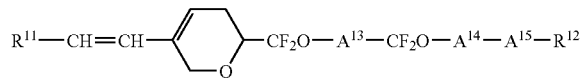

where $R^{11}$, $R^{12}$, $A^{13}$, $A^{14}$ and $A^{15}$ are as defined for the formula I above.

Illustrative compounds of the formula I-OBAI are, inter alia, the above-mentioned compounds of the formula I-CBIm and compounds of the formula I-OBAIa; the radicals $R^{11}$, $R^{12}$, $L^{11}$, $L^{12}$, $L^{13}$, $L^{14}$, $L^{15}$ and $L^{16}$ are as defined in Table 9 below. Illustrative compounds of the formula I-OBBI are, inter alia, the above-mentioned compounds of the formula I-CBIIIe and compounds of the formula I-OBBIa; the radicals $R^{11}$, $R^{12}$, $L^{11}$, $L^{12}$, $L^{13}$, $L^{14}$, $L^{15}$ and $L^{16}$ are as defined in Table 9 below.

where $R^{11}$, $R^{12}$, $Z^2$, $A^3$, $A^{14}$ and $A^{15}$ are as defined for the formula I above. $R^{11}$ is preferably H, a straight-chain alkenyl or in particular alkanyl radical having from 1 to 7 carbon atoms, and $R^{12}$ is preferably halogen, in particular fluorine, or an unbranched alkanyl or alkoxy radical having from 1 to 5 carbon atoms which is optionally mono- or polysubstituted by halogen, in particular fluorine. Of these compounds, those of the formulae I-PBAI and I-PBBI are very particularly preferred:

I-PBAI

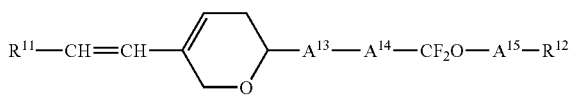

I-OBAIa

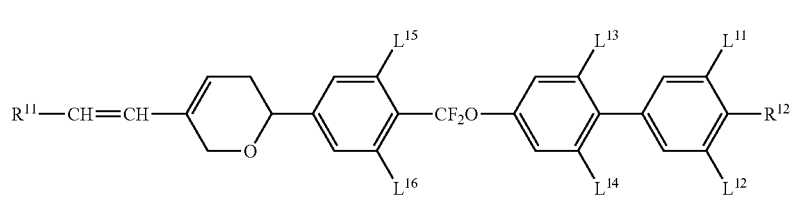

I-OBBIa

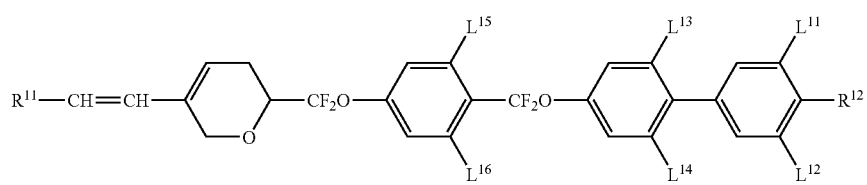

Preferred sub-groups of the formula I-P are formed by compounds where

W=—C(=O)— (formula I-PA) and in particular by compounds where

W=—CH$_2$— (formula I-PB).

Particularly preferred compounds of the formula I-PB are compounds of the formulae I-PBA and I-PBB:

I-PBA

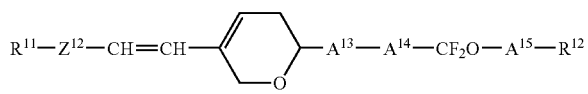

I-PBB

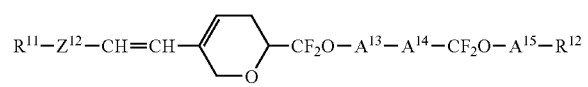

I-PBBI

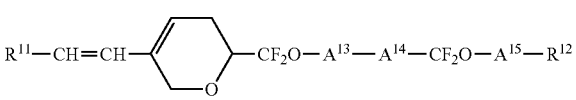

where $R^{11}$, $R^{12}$, $A^{13}$, $A^{14}$ and $A^{15}$ are as defined for the formula I above. Illustrative compounds of the formula I-PBAI are, inter alia, the above-mentioned compounds of the formulae I-CBIj and I-CBIn and compounds of the formula I-PBAIa; the radicals $R^{11}$, $R^{12}$, $L^{11}$, $L^{12}$, $L^{13}$, $L^{14}$, $L^{15}$ and $L^{16}$ are as defined in Table 9 below. Illustrative compounds of the formula I-PBBI are, inter alia, the above-mentioned compounds of the formula I-CBIIIf and compounds of the formula I-PBBIa; the radicals $R^{11}$, $R^{12}$, $L^{11}$, $L^{12}$, $L^{13}$, $L^{14}$, $L^{15}$ and $L^{16}$ are as defined in Table 9 below.

I-PBAIa

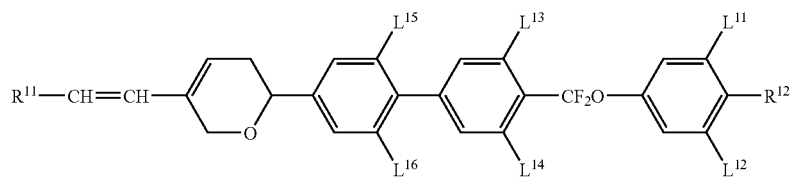

I-PBBIa

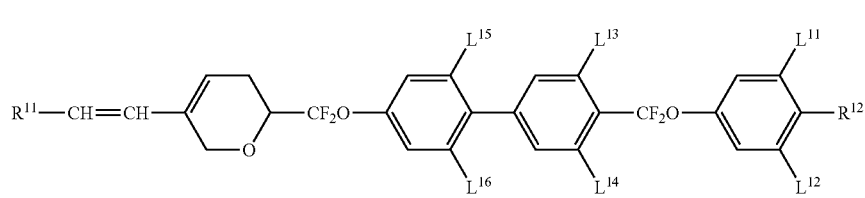

Preferred sub-groups of the formula I-Q are formed by compounds of the formula I-QA (where W=—C(=O)—) and in particular by compounds of the formula I-QB (where W=—CH$_2$—):

I-QA

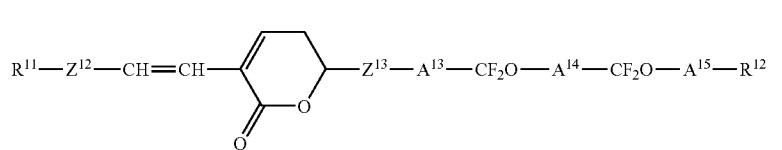

I-QB

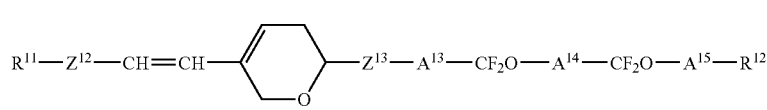

where R$^{11}$, R$^{12}$, Z$^{12}$, Z$^{13}$, A$^{13}$, A$^{14}$ and A$^{15}$ are as defined for the formula I above.

Particularly preferred compounds of the formula I-QB are compounds of the formula I-QBA:

I-QBA

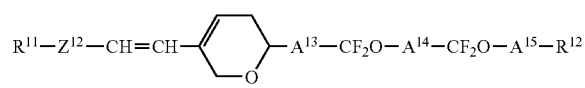

where R$^{11}$, R$^{12}$, Z$^2$, A$^3$, A$^{14}$ and A$^{15}$ are as defined for the formula I above.

Of these compounds, those of the formula I-QBAI are very particularly preferred:

I-QBAI

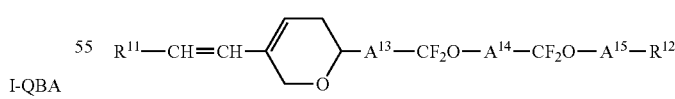

where R$^{11}$, R$^{12}$, A$^{13}$, A$^{14}$ and A$^{15}$ are as defined for the formula I above. Illustrative compounds of the formula I-QBAI are, inter alia, compounds of the formulae I-QBAIa and I-QBAIb; the radicals R$^{11}$, R$^{12}$, L$^{11}$, L$^{12}$, L$^{13}$, L$^{14}$, L$^{15}$ and L$^{16}$ are as defined in Table 8 and 9 respectively below.

TABLE 8

I-QBAIa structure: R^{11}—CH=CH—[dihydropyran]—[cyclohexyl]—CF$_2$O—[phenyl with L$^{13}$, L$^{14}$]—CF$_2$O—[phenyl with L$^{11}$, L$^{12}$, L$^{12}$]

I-QBAIb structure: R^{11}—CH=CH—[dihydropyran]—[phenyl with L$^{15}$, L$^{16}$]—CF$_2$O—[phenyl with L$^{13}$, L$^{14}$]—CF$_2$O—[phenyl with L$^{11}$, L$^{12}$, L$^{12}$]

| I-MBBIa/I-MBBIIa/I-NBBIa/IQBAIa No. | L$^{11}$ | L$^{12}$ | L$^{13}$ | L$^{14}$ | R$^{12}$ | R$^{11}$ |
|---|---|---|---|---|---|---|
| 1 | H | H | H | H | F | CH$_3$ |
| 2 | H | H | H | H | CF$_3$ | CH$_3$ |
| 3 | H | H | H | H | OCF$_3$ | CH$_3$ |
| 4 | H | H | H | H | OCHF$_2$ | CH$_3$ |
| 5 | F | H | H | H | F | CH$_3$ |
| 6 | F | H | H | H | CF$_3$ | CH$_3$ |
| 7 | F | H | H | H | OCF$_3$ | CH$_3$ |
| 8 | F | H | H | H | OCHF$_2$ | CH$_3$ |
| 9 | F | F | H | H | F | CH$_3$ |
| 10 | F | F | H | H | CF$_3$ | CH$_3$ |
| 11 | F | F | H | H | OCF$_3$ | CH$_3$ |
| 12 | F | F | H | H | OCHF$_2$ | CH$_3$ |
| 13 | H | H | H | H | F | C$_2$H$_5$ |
| 14 | H | H | H | H | CF$_3$ | C$_2$H$_5$ |
| 15 | H | H | H | H | OCF$_3$ | C$_2$H$_5$ |
| 16 | H | H | H | H | OCHF$_2$ | C$_2$H$_5$ |
| 17 | F | H | H | H | F | C$_2$H$_5$ |
| 18 | F | H | H | H | CF$_3$ | C$_2$H$_5$ |
| 19 | F | H | H | H | OCF$_3$ | C$_2$H$_5$ |
| 20 | F | H | H | H | OCHF$_2$ | C$_2$H$_5$ |
| 21 | F | F | H | H | F | C$_2$H$_5$ |
| 22 | F | F | H | H | CF$_3$ | C$_2$H$_5$ |
| 23 | F | F | H | H | OCF$_3$ | C$_2$H$_5$ |
| 24 | F | F | H | H | OCHF$_2$ | C$_2$H$_5$ |
| 25 | H | H | H | H | F | n-C$_3$H$_7$ |
| 26 | H | H | H | H | CF$_3$ | n-C$_3$H$_7$ |
| 27 | H | H | H | H | OCF$_3$ | n-C$_3$H$_7$ |
| 28 | H | H | H | H | OCHF$_2$ | n-C$_3$H$_7$ |
| 29 | F | H | H | H | F | n-C$_3$H$_7$ |
| 30 | F | H | H | H | CF$_3$ | n-C$_3$H$_7$ |
| 31 | F | H | H | H | OCF$_3$ | n-C$_3$H$_7$ |
| 32 | F | H | H | H | OCHF$_2$ | n-C$_3$H$_7$ |
| 33 | F | F | H | H | F | n-C$_3$H$_7$ |
| 34 | F | F | H | H | CF$_3$ | n-C$_3$H$_7$ |
| 35 | F | F | H | H | OCF$_3$ | n-C$_3$H$_7$ |
| 36 | F | F | H | H | OCHF$_2$ | n-C$_3$H$_7$ |
| 37 | H | H | H | H | F | n-C$_4$H$_9$ |
| 38 | H | H | H | H | CF$_3$ | n-C$_4$H$_9$ |
| 39 | H | H | H | H | OCF$_3$ | n-C$_4$H$_9$ |
| 40 | H | H | H | H | OCHF$_2$ | n-C$_4$H$_9$ |
| 41 | F | H | H | H | F | n-C$_4$H$_9$ |
| 42 | F | H | H | H | CF$_3$ | n-C$_4$H$_9$ |
| 43 | F | H | H | H | OCF$_3$ | n-C$_4$H$_9$ |
| 44 | F | H | H | H | OCHF$_2$ | n-C$_4$H$_9$ |
| 45 | F | F | H | H | F | n-C$_4$H$_9$ |
| 46 | F | F | H | H | CF$_3$ | n-C$_4$H$_9$ |
| 47 | F | F | H | H | OCF$_3$ | n-C$_4$H$_9$ |
| 48 | F | F | H | H | OCHF$_2$ | n-C$_4$H$_9$ |
| 49 | H | H | H | H | F | n-C$_5$H$_{11}$ |
| 50 | H | H | H | H | CF$_3$ | n-C$_5$H$_{11}$ |
| 51 | H | H | H | H | OCF$_3$ | n-C$_5$H$_{11}$ |
| 52 | H | H | H | H | OCHF$_2$ | n-C$_5$H$_{11}$ |
| 53 | F | H | H | H | F | n-C$_5$H$_{11}$ |
| 54 | F | H | H | H | CF$_3$ | n-C$_5$H$_{11}$ |
| 55 | F | H | H | H | OCF$_3$ | n-C$_5$H$_{11}$ |
| 56 | F | H | H | H | OCHF$_2$ | n-C$_5$H$_{11}$ |

TABLE 8-continued

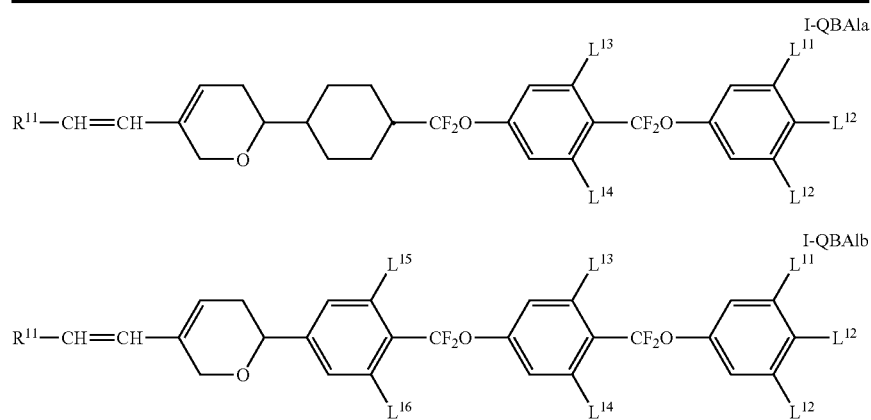

I-QBAIa

I-QBAIb

| I-MBBIa/I-MBBIIa/I-NBBIa/IQBAIa No. | L11 | L12 | L13 | L14 | R12 | R11 |
|---|---|---|---|---|---|---|
| 57 | F | F | H | H | F | n-$C_5H_{11}$ |
| 58 | F | F | H | H | $CF_3$ | n-$C_5H_{11}$ |
| 59 | F | F | H | H | $OCF_3$ | n-$C_5H_{11}$ |
| 60 | F | F | H | H | $OCHF_2$ | n-$C_5H_{11}$ |
| 61 | F | F | F | H | F | $CH_3$ |
| 62 | F | F | F | H | $CF_3$ | $CH_3$ |
| 63 | F | F | F | H | $OCF_3$ | $CH_3$ |
| 64 | F | F | F | H | $OCHF_2$ | $CH_3$ |
| 65 | F | F | F | H | F | $C_2H_5$ |
| 66 | F | F | F | H | $CF_3$ | $C_2H_5$ |
| 67 | F | F | F | H | $OCF_3$ | $C_2H_5$ |
| 68 | F | F | F | H | $OCHF_2$ | $C_2H_5$ |
| 69 | F | F | F | H | F | n-$C_3H_7$ |
| 70 | F | F | F | H | $CF_3$ | n-$C_3H_7$ |
| 71 | F | F | F | H | $OCF_3$ | n-$C_3H_7$ |
| 72 | F | F | F | H | $OCHF_2$ | n-$C_3H_7$ |
| 73 | F | F | F | H | F | n-$C_4H_9$ |
| 74 | F | F | F | H | $CF_3$ | n-$C_4H_9$ |
| 75 | F | F | F | H | $OCF_3$ | n-$C_4H_9$ |
| 76 | F | F | F | H | $OCHF_2$ | n-$C_4H_9$ |
| 77 | F | F | F | H | F | n-$C_5H_{11}$ |
| 78 | F | F | F | H | $CF_3$ | n-$C_5H_{11}$ |
| 79 | F | F | F | H | $OCF_3$ | n-$C_5H_{11}$ |
| 80 | F | F | F | H | $OCHF2$ | n-$C_5H_{11}$ |

TABLE 9

| I-NBAIa/I-NBBIb/ I-NBCIa/I-OBAIa/ I-OBBIa/I-PBAIa/ I-PBBIa/I-QBAIb No. | L15 | L16 | L13 | L14 | L11 | L12 | R11 | R12 |
|---|---|---|---|---|---|---|---|---|
| 1 | H | H | H | H | H | H | $CH_3$ | F |
| 2 | H | H | H | H | H | H | $CH_3$ | $CF_3$ |
| 3 | H | H | H | H | H | H | $CH_3$ | $OCF_3$ |
| 4 | H | H | H | H | H | H | $CH_3$ | $OCHF_2$ |
| 5 | H | H | H | H | F | H | $CH_3$ | F |
| 6 | H | H | H | H | F | H | $CH_3$ | $CF_3$ |
| 7 | H | H | H | H | F | H | $CH_3$ | $OCF_3$ |
| 8 | H | H | H | H | F | H | $CH_3$ | $OCHF_2$ |
| 9 | H | H | H | H | F | F | $CH_3$ | F |
| 10 | H | H | H | H | F | F | $CH_3$ | $CF_3$ |
| 11 | H | H | H | H | F | F | $CH_3$ | $OCF_3$ |
| 12 | H | H | H | H | F | F | $CH_3$ | $OCHF_2$ |
| 13 | H | H | F | H | F | F | $CH_3$ | F |
| 14 | H | H | F | H | F | F | $CH_3$ | $CF_3$ |
| 15 | H | H | F | H | F | F | $CH_3$ | $OCF_3$ |
| 16 | H | H | F | H | F | F | $CH_3$ | $OCHF_2$ |
| 17 | H | H | F | F | F | F | $CH_3$ | F |
| 18 | H | H | F | F | F | F | $CH_3$ | $CF_3$ |
| 19 | H | H | F | F | F | F | $CH_3$ | $OCF_3$ |
| 20 | H | H | F | F | F | F | $CH_3$ | $OCHF_2$ |
| 21 | F | H | F | F | F | F | $CH_3$ | F |
| 22 | F | H | F | F | F | F | $CH_3$ | $CF_3$ |
| 23 | F | H | F | F | F | F | $CH_3$ | $OCF_3$ |
| 24 | F | H | F | F | F | F | $CH_3$ | $OCHF_2$ |
| 25 | H | H | F | H | H | H | $CH_3$ | F |
| 26 | H | H | F | H | H | H | $CH_3$ | $CF_3$ |
| 27 | H | H | F | H | H | H | $CH_3$ | $OCF_3$ |
| 28 | H | H | F | H | H | H | $CH_3$ | $OCHF_2$ |
| 29 | H | H | H | H | H | H | $C_2H_5$ | F |
| 30 | H | H | H | H | H | H | $C_2H_5$ | $CF_3$ |
| 31 | H | H | H | H | H | H | $C_2H_5$ | $OCF_3$ |
| 32 | H | H | H | H | H | H | $C_2H_5$ | $OCHF_2$ |
| 33 | H | H | H | H | F | H | $C_2H_5$ | F |
| 34 | H | H | H | H | F | H | $C_2H_5$ | $CF_3$ |
| 35 | H | H | H | H | F | H | $C_2H_5$ | $OCF_3$ |
| 36 | H | H | H | H | F | H | $C_2H_5$ | $OCHF_2$ |
| 37 | H | H | H | H | F | F | $C_2H_5$ | F |
| 38 | H | H | H | H | F | F | $C_2H_5$ | $CF_3$ |
| 39 | H | H | H | H | F | F | $C_2H_5$ | $OCF_3$ |
| 40 | H | H | H | H | F | F | $C_2H_5$ | $OCHF_2$ |
| 41 | H | H | F | H | F | F | $C_2H_5$ | F |
| 42 | H | H | F | F | F | F | $C_2H_5$ | $CF_3$ |

TABLE 9-continued

| I-NBAIa/I-NBBIb/I-NBCIa/I-OBAIa/I-OBBIa/I-PBAIa/I-PBBIa/I-QBAIb No. | $L^{15}$ | $L^{16}$ | $L^{13}$ | $L^{14}$ | $L^{11}$ | $L^{12}$ | $R^{11}$ | $R^{12}$ |
|---|---|---|---|---|---|---|---|---|
| 43 | H | H | F | H | F | F | $C_2H_5$ | $OCF_3$ |
| 44 | H | H | F | H | F | F | $C_2H_5$ | $OCHF_2$ |
| 45 | H | H | F | F | F | F | $C_2H_5$ | F |
| 46 | H | H | F | F | F | F | $C_2H_5$ | $CF_3$ |
| 47 | H | H | F | F | F | F | $C_2H_5$ | $OCF_3$ |
| 48 | H | H | F | F | F | F | $C_2H_5$ | $OCHF_2$ |
| 49 | F | H | F | F | F | F | $C_2H_5$ | F |
| 50 | F | H | F | F | F | F | $C_2H_5$ | $CF_3$ |
| 51 | F | H | F | F | F | F | $C_2H_5$ | $OCF_3$ |
| 52 | F | H | F | F | F | F | $C_2H_5$ | $OCHF_2$ |
| 53 | H | H | F | H | F | H | $C_2H_5$ | F |
| 54 | H | H | F | H | F | H | $C_2H_5$ | $CF_3$ |
| 55 | H | H | F | H | F | H | $C_2H_5$ | $OCF_3$ |
| 56 | H | H | F | H | F | H | $C_2H_5$ | $OCHF_2$ |
| 57 | H | H | H | H | H | H | $nC_3H_7$ | F |
| 58 | H | H | H | H | H | H | $n-C_3H_7$ | $CF_3$ |
| 59 | H | H | H | H | H | H | $n-C_3H_7$ | $OCF_3$ |
| 60 | H | H | H | H | H | H | $n-C_3H_7$ | $OCHF_2$ |
| 61 | H | H | H | H | F | H | $n-C_3H_7$ | F |
| 62 | H | H | H | H | F | H | $n-C_3H_7$ | $CF_3$ |
| 63 | H | H | H | H | F | H | $n-C_3H_7$ | $OCF_3$ |
| 64 | H | H | H | H | F | H | $n-C_3H_7$ | $OCHF_2$ |
| 65 | H | H | H | H | F | F | $n-C_3H_7$ | F |
| 66 | H | H | H | H | F | F | $n-C_3H_7$ | $CF_3$ |
| 67 | H | H | H | H | F | F | $n-C_3H_7$ | $OCF_3$ |
| 68 | H | H | H | H | F | F | $n-C_3H_7$ | $OCHF_2$ |
| 69 | H | H | F | H | F | F | $n-C_3H_7$ | F |
| 70 | H | H | F | H | F | F | $n-C_3H_7$ | $CF_3$ |
| 71 | H | H | F | H | F | F | $n-C_3H_7$ | $OCF_3$ |
| 72 | H | H | F | H | F | F | $n-C_3H_7$ | $OCHF_2$ |
| 73 | H | H | F | F | F | F | $n-C_3H_7$ | F |
| 74 | H | H | F | F | F | F | $n-C_3H_7$ | $CF_3$ |
| 75 | H | H | F | F | F | F | $n-C_3H_7$ | $OCF_3$ |
| 76 | H | H | F | F | F | F | $n-C_3H_7$ | $OCHF_2$ |
| 77 | F | H | F | F | F | F | $n-C_3H_7$ | F |
| 78 | F | H | F | F | F | F | $n-C_3H_7$ | $CF_3$ |
| 79 | F | H | F | F | F | F | $n-C_3H_7$ | $OCF_3$ |
| 80 | F | H | F | F | F | F | $n-C_3H_7$ | $OCHF_2$ |
| 81 | H | H | F | H | F | H | $n-C_3H_7$ | F |
| 82 | H | H | F | H | F | H | $n-C_3H_7$ | $CF_3$ |
| 83 | H | H | F | H | F | H | $n-C_3H_7$ | $OCF_3$ |
| 84 | H | H | F | H | F | H | $n-C_3H_7$ | $OCHF_2$ |
| 85 | H | H | H | H | H | H | $n-C_4H_9$ | F |
| 86 | H | H | H | H | H | H | $n-C_4H_9$ | $CF_3$ |
| 87 | H | H | H | H | H | H | $n-C_4H_9$ | $OCF_3$ |
| 88 | H | H | H | H | H | H | $n-C_4H_9$ | $OCHF_2$ |
| 89 | H | H | H | H | F | H | $n-C_4H_9$ | F |
| 90 | H | H | H | H | F | H | $n-C_4H_9$ | $CF_3$ |
| 91 | H | H | H | H | F | H | $n-C_4H_9$ | $OCF_3$ |
| 92 | H | H | H | H | F | H | $n-C_4H_9$ | $OCHF_2$ |
| 93 | H | H | H | H | F | F | $n-C_4H_9$ | F |
| 94 | H | H | H | H | F | F | $n-C_4H_9$ | $CF_3$ |
| 95 | H | H | H | H | F | F | $n-C_4H_9$ | $OCF_3$ |
| 96 | H | H | H | H | F | F | $n-C_4H_9$ | $OCHF_2$ |
| 97 | H | H | F | H | F | F | $n-C_4H_9$ | F |
| 98 | H | H | F | H | F | F | $n-C_4H_9$ | $CF_3$ |
| 99 | H | H | F | H | F | F | $n-C_4H_9$ | $OCF_3$ |
| 100 | H | H | F | H | F | F | $n-C_4H_9$ | $OCHF_2$ |
| 101 | H | H | F | F | F | F | $n-C_4H_9$ | F |
| 102 | H | H | F | F | F | F | $n-C_4H_9$ | $CF_3$ |
| 103 | H | H | F | F | F | F | $n-C_4H_9$ | $OCF_3$ |
| 104 | H | H | F | F | F | F | $n-C_4H_9$ | $OCHF_2$ |
| 105 | F | H | F | F | F | F | $n-C_4H_9$ | F |
| 106 | F | H | F | F | F | F | $n-C_4H_9$ | $CF_3$ |
| 107 | F | H | F | F | F | F | $n-C_4H_9$ | $OCF_3$ |
| 108 | F | H | F | F | F | F | $n-C_4H_9$ | $OCHF_2$ |
| 109 | H | H | F | H | F | H | $n-C_4H_9$ | F |
| 110 | H | H | F | H | F | H | $n-C_4H_9$ | $CF_3$ |
| 111 | H | H | F | H | F | H | $n-C_4H_9$ | $OCF_3$ |
| 112 | H | H | F | H | F | H | $n-C_4H_9$ | $OCHF_2$ |
| 113 | H | H | H | H | H | H | $n-C_5H_{11}$ | F |
| 114 | H | H | H | H | H | H | $n-C_5H_{11}$ | $CF_3$ |
| 115 | H | H | H | H | H | H | $n-C_5H_{11}$ | $OCF_3$ |
| 116 | H | H | H | H | H | H | $n-C_5H_{11}$ | $OCHF_2$ |
| 117 | H | H | H | H | F | H | $n-C_5H_{11}$ | F |
| 118 | H | H | H | H | F | H | $n-C_5H_{11}$ | $CF_3$ |
| 119 | H | H | H | H | F | H | $n-C_5H_{11}$ | $OCF_3$ |
| 120 | H | H | H | H | F | H | $n-C_5H_{11}$ | $OCHF_2$ |
| 121 | H | H | H | H | F | F | $n-C_5H_{11}$ | F |
| 122 | H | H | H | H | F | F | $n-C_5H_{11}$ | $CF_3$ |
| 123 | H | H | H | H | F | F | $n-C_5H_{11}$ | $OCF_3$ |
| 124 | H | H | H | H | F | F | $n-C_5H_{11}$ | $OCHF_2$ |
| 125 | H | H | F | H | F | F | $n-C_5H_{11}$ | F |
| 126 | H | H | F | H | F | F | $n-C_5H_{11}$ | $CF_3$ |
| 127 | H | H | F | H | F | F | $n-C_5H_{11}$ | $OCF_3$ |
| 128 | H | H | F | H | F | F | $n-C_5H_{11}$ | $OCHF_2$ |
| 129 | H | H | F | F | F | F | $n-C_5H_{11}$ | F |
| 130 | H | H | F | F | F | F | $n-C_5H_{11}$ | $CF_3$ |
| 131 | H | H | F | F | F | F | $n-C_5H_{11}$ | $OCF_3$ |
| 132 | H | H | F | F | F | F | $n-C_5H_{11}$ | $OCHF_2$ |
| 133 | F | H | F | F | F | F | $n-C_5H_{11}$ | F |
| 134 | F | H | F | F | F | F | $n-C_5H_{11}$ | $CF_3$ |
| 135 | F | H | F | F | F | F | $n-C_5H_{11}$ | $OCF_3$ |
| 136 | F | H | F | F | F | F | $n-C_5H_{11}$ | $OCHF_2$ |
| 137 | H | H | F | H | F | H | $n-C_5H_{11}$ | F |
| 138 | H | H | F | H | F | H | $n-C_5H_{11}$ | $CF_3$ |
| 139 | H | H | F | H | F | H | $n-C_5H_{11}$ | $OCF_3$ |
| 140 | H | H | F | H | F | H | $n-C_5H_{11}$ | $OCHF_2$ |

The preferred compounds of the invention furthermore include pyran derivatives of the formula I in which e is 1 and $A^{15}$-$R^{12}$ is —⬡=O or

—⬡(OR$^{13}$)(OR$^{14}$), where $R^{13}$ and $R^{14}$, independently of one another, are an alkanyl radical having from 1 to 7 carbon atoms or together are an alkylene bridge having from 2 to 7 carbon atoms. The cyclohexanones are illustrated by the formula I-R and their ketals by the formula I-S:

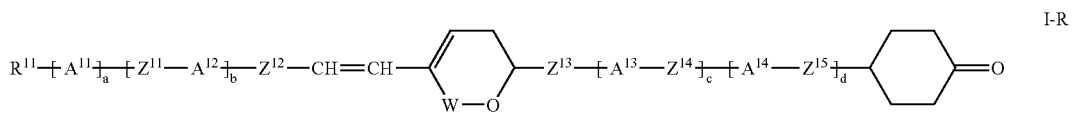

I-R

-continued

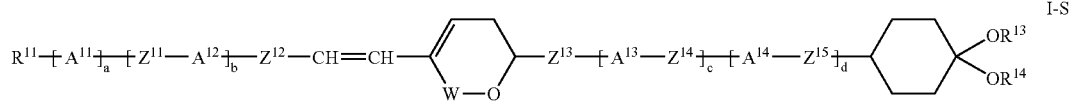
I-S where $R^{11}$, $R^{13}$, $R^{14}$, a, b, c, d, $Z^{11}$, $Z^{12}$, $Z^{13}$, $Z^{14}$, $Z^{15}$, $A^{11}$, $A^{12}$, $A^{13}$ and $A^{14}$ are as defined for the formula I above. Preferred sub-groups of compounds of the formulae I-R and I-S are formed by compounds where W=—C(=O)— (formula I-RA and I-SA respectively) and in particular W=—CH$_2$— (formula I-RB and I-SB respectively).

Particularly preferred compounds of the formulae I-RB and I-SB are compounds of the formulae I-RBA, I-SBA, I-RBB and I-SBB:

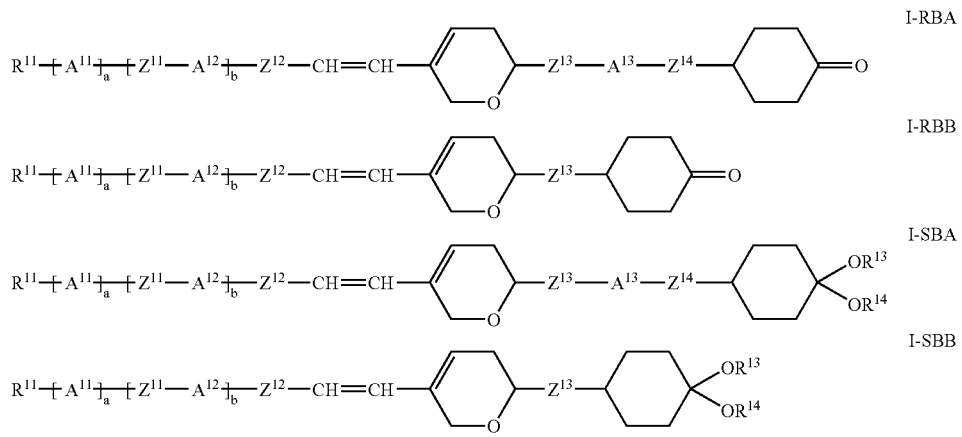

where $R^{11}$, $R^{13}$, $R^{14}$, a, b, $Z^{11}$, $Z^{12}$, $Z^{13}$, $Z^{14}$, $A^{11}$, $A^{12}$ and $A^{13}$ are as defined for the formula I above. $R^{11}$ is preferably a straight-chain alkenyl or in particular alkanyl radical having from 1 to 7 carbon atoms. $R^{13}$ and $R^{14}$ are preferably each methyl or ethyl or together are —CH$_2$CH$_2$— or —CH$_2$C(CH$_3$)$_2$—CH$_2$—. $Z^{12}$ and $Z^{14}$ are each preferably a single bond, while $Z^{13}$ is preferably a single bond, —C(=O)O— or —CF$_2$O—. Of these compounds, those of the formulae I-RBAI, I-RBAII, I-RBBI and I-RBBII and the corresponding ketals I-SBAI, I-SBAII, I-SBBI and I-SBBII are very particularly preferred:

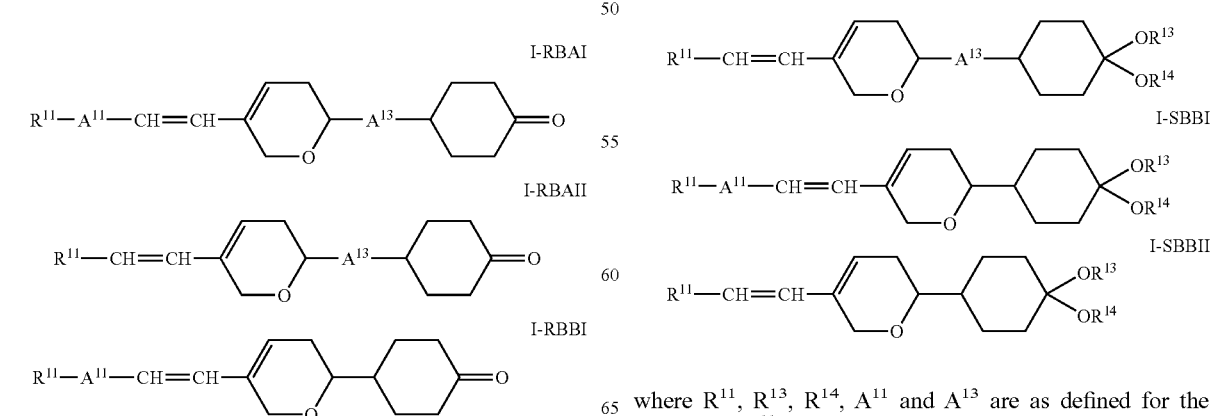

where $R^{11}$, $R^{13}$, $R^{14}$, $A^{11}$ and $A^{13}$ are as defined for the formula I. $R^{11}$ is preferably H, alkanyl or alkenyl having from 1 to 5 carbon atoms, $A^{11}$ is 1,4-cyclohexylene and $A^{13}$ is 1,4-cyclohexylene, or 1,4-phenylene which is optionally substituted by fluorine in the 3- and/or 5-position. $R^{13}$ and $R^{14}$ are preferably each methyl or ethyl or together are —$CH_2CH_2$— or —$CH_2C(CH_3)_2$—$CH_2$—.

The invention furthermore relates to processes for the preparation of pyran derivatives, in particular of the general formula I.

A first process according to the invention is characterised in that it includes, as one process step, an enyne metathesis reaction of an enyne of the general formula II to give a pyran derivative of the formula I according to the invention in the presence of a metathesis catalyst:

Scheme 1

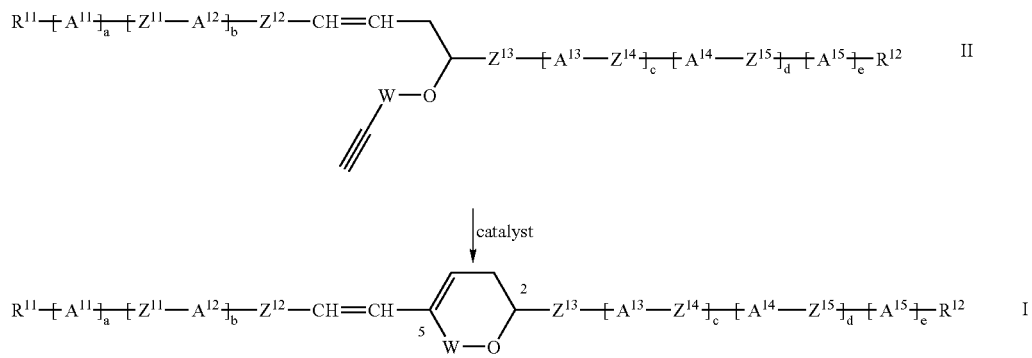

where a, b, c, d, e, W, $R^{11}$, $R^{12}$, $Z^{11}$, $Z^{12}$, $Z^{13}$, $Z^{14}$, $Z^{15}$, $A^{11}$, $A^{12}$, $A^{13}$, $A^{14}$ and $A^{15}$ in the formulae I and III are as defined for the formula I above; with the proviso that, in the case of direct linking of $Z^{13}$ and $R^{12}$ to give -$Z^{13}$-$R^{12}$, $R^{12}$ is H, aralkyl or alkanyl if $Z^{13}$ is —C(=O)—, $R^{12}$ is aralkyl or alkanyl if $Z^{13}$ is —C(=O)—O—, and $Z^{13}$ is not —$CH_2$O— or —$CF_2$O—; that, in the case of direct linking of $Z^{14}$ and $R^{12}$ to give -$Z^{14}$-$R^{12}$, $R^{12}$ is H, aralkyl or alkanyl if $Z^{14}$ is —C(=O)—, $R^{12}$ is aralkyl or alkanyl if $Z^{14}$ is —C(=O)—O—, and $Z^{14}$ is not —$CH_2$O— or —$CF_2$O—; that, in the case of direct linking of $Z^{15}$ and $R^{12}$ to give -$Z^{15}$-$R^{12}$, $R^{12}$ is H, aralkyl or alkanyl if $Z^{15}$ is —C(=O)—, $R^{12}$ is aralkyl or alkanyl if $Z^{15}$ is —C(=O)—O—, and $Z^{15}$ is not —$CH_2$O— or —$CF_2$O—.

In general, the pyran derivative of the formula I is obtained predominantly or exclusively as the E isomer with respect to the exocyclic double bond.

Metathesis reactions (frequently also known as olefin metathesis) for the synthesis of carbocyclic compounds (or of (poly)olefins from carbocyclic compounds) are well known in the prior art (see, inter alia, R. H. Grubbs and S. Chang, *Tetrahedron* 54 (1998) 4413; T. M. Trnka and R. H. Grubbs, Acc. Chem. Res. 2001, 34, 18; S. K. Armstrong, *J. Chem. Soc., Perkin Trans. I*, 1998, 371; A. Fürstner et al., *Chem. Eur. J.* 2001, 7, 3236, and the references cited therein). They can be used to form new C—C bonds and thus more complex molecules by simultaneous breaking and formation of unsaturated carbon-carbon bonds, in particular in the presence of selected metal-carbene complexes.

A distinction can be made here between various ring-closing and ring-opening metathesis reaction types. Besides ring-opening metathesis polymerisation (ROMP), which is of no further interest here, (intramolecular) ring-closing metathesis (RCM), cross metathesis (CM) and enyne metathesis (enyne), in particular, are of particular importance.

The said metathesis types are illustrated in scheme 2 using the example of a hydrocarbon:

Scheme 2

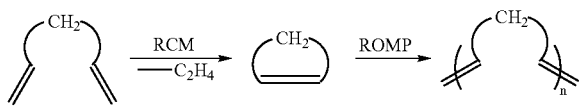

-continued

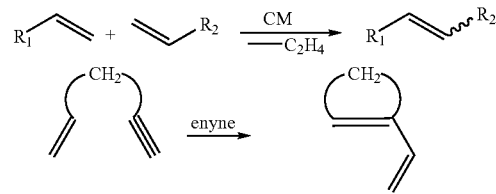

The metathesis reactions are preferably catalysed by so-called Schrock (or Grubbs) carbene complexes (metal-alkylidene complexes) of transition metals, such as tungsten, molybdenum and in particular ruthenium. These complexes usually have a structure which can be reproduced by the following formula COMP-A (cf., inter alia, WO 96/04289, WO 97/06185, WO 99/00396 and WO 99/00397):

COMP-A where Met is a transition metal, $(L)_x$ stands for a plurality of identical or different ligands, and $R_y$ is an organic radical, usually aryl, alkanyl or alkenyl.

The ring-closing metathesis reactions mentioned have also been employed to form heterocyclic ring systems and to prepare corresponding compounds. Thus, nitrogen heterocyclic compounds are accessible in large number by olefin metathesis. According to the literature, oxygen heterocyclic compounds can also be prepared with the aid of this synthetic methodology, but apparently in a significantly smaller structural breadth.

Thus, metathesis processes for the synthesis of pyran derivatives containing both an exocyclic substituent on a carbon atom of the endocyclic C=C double bond formed by metathesis and a 2,5-disubstituted

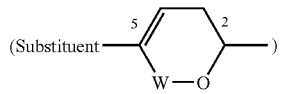

and having industrially useful properties and which can be used, for example, as mesogenic materials or as precursors for the preparation of other compounds having mesogenic properties which contain a pyran ring, starting from readily accessible starting compounds have hitherto not been described in the prior art. This is possibly attributable to the fact that the ring-closure reaction to give O-heterocyclic compounds under metathesis conditions has, until the present invention, usually not succeeded or not succeeded reproducibly if one of the carbon atoms of one of the reacting C=C double bonds of the starting compound(s) is disubstituted (cf. also S. K. Armstrong, *J. Chem. Soc., Perkin Trans. I*, 1998, 371, in particular p. 376).

With respect to enyne metathesis of pyran derivatives, only a single synthesis starting from an alkyn-1-yl boronate has been described in the prior art (J. Renaud et al., *Angew. Chem.* 2000, 112, 3231), but this firstly requires the preparation of the corresponding boronate.

It is therefore particularly surprising that the enyne metathesis starting from compounds of the formula II in the presence of a metathesis catalyst leads reliably and efficiently to the pyran derivatives of the formula I according to the invention.

Preferred metathesis catalysts for the enyne metathesis are the transition-metal-alkylidene complexes of the general formula COMP-A described in the prior art (see, inter alia, R. H. Grubbs and S. Chang, *Tetrahedron* 54 (1998) 4413; T. M. Trnka and R. H. Grubbs, Acc. Chem. Res. 2001, 34, 18; S. K. Armstrong, *J. Chem. Soc.*, Perkin Trans. I, 1998, 371; A. Fürstner et al., *Chem. Eur. J.* 2001, 7, 3236, and the references cited therein). This is preferably a complex of the formula COMP-A where Met=tungsten, molybdenum or ruthenium. Oxo-tungsten complexes of the trans-W(=O)Cl$_2$(aryl)$_2$ type (where aryl is preferably 2,6-dibromophenyl), which have been described, inter alia, by W. A Nugent et al., J. Am. Chem. Soc., 1995, 117, 8992, are furthermore used as metathesis catalysts in the processes according to the invention.

Preferred molybdenum metathesis catalysts are those of the formulae COMP-Mo1, COMP-Mo2, COMP-Mo3 and COMP-Mo4, while the formula COMP-W1 shows a preferred tungsten metathesis catalyst:

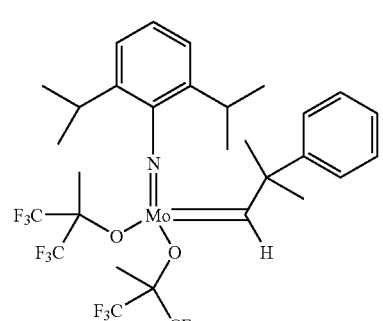
COMP-Mo1

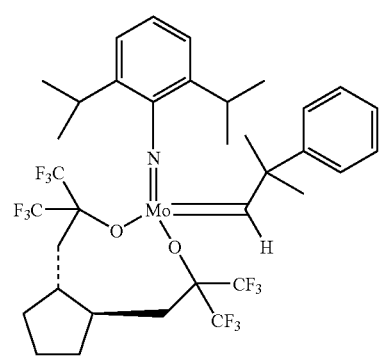
COMP-Mo2

COMP-Mo3 a: R = i-propyl
b: R = methyl
c: R = chlorine

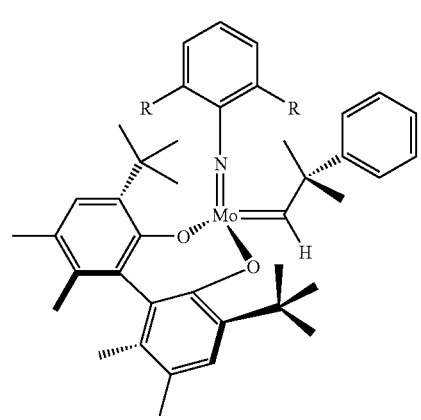

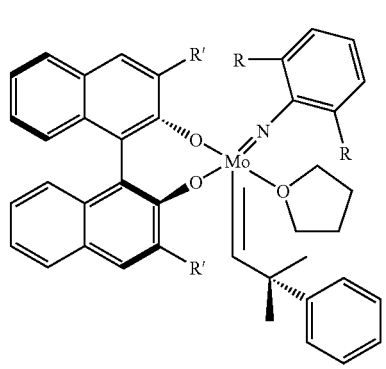
COMP-Mo4

-continued

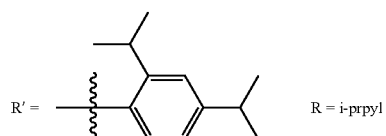

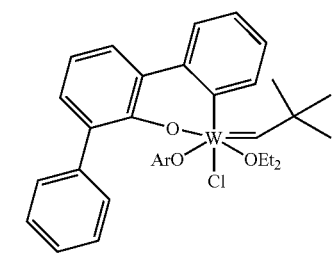

COMP-W1

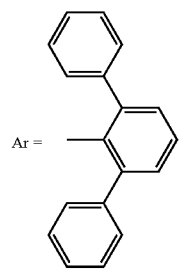

Et = ethyl

Particularly preferred complexes for use as enyne metathesis catalyst in the first process according to the invention are ruthenium-alkylidene complexes of the COMP-RuA type, which are known per se from the literature (see, inter alia, WO 96/04289, WO 97/06185, WO 99/00396, WO 99/00397, WO 99/29701, WO 99/51344, WO 00/15339, EP 1 022 282 A2, WO 00/58322, WO 00/71554, WO 02/14336, WO 02/14376, WO 02/083742):

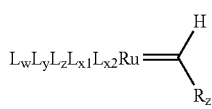

COMP-RuA $L_{x1}$ and/or $L_{x2}$ here are preferably anionic ligands, preferably bromine, iodine or in particular chlorine, if desired also O-aralkyl, while $L_y$ and $L_z$ are preferably other, usually neutral ligands, such as, for example, $PPh_3$ (Ph=phenyl), $P(i-Pr)_3$ (i-Pr=isopropyl), $PCy_3$ (Cy=cyclohexyl), $P(Cp)_3$ (Cp=cyclopentadienyl), unsubstituted or substituted pyridyl, $Im^1$, $Im^2$ or alkoxy coordinated via the oxygen atom. $L_w$ is an optionally present ligand, i.e. W is 0 or 1, where this usually has the same meaning as $L_{x1}$, $L_{x2}$, $L_y$ and/or $L_z$. $R_z$ is an organic radical, in particular aryl, alkanyl or alkenyl.

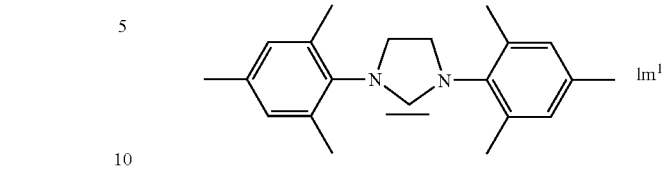

$Im^1$

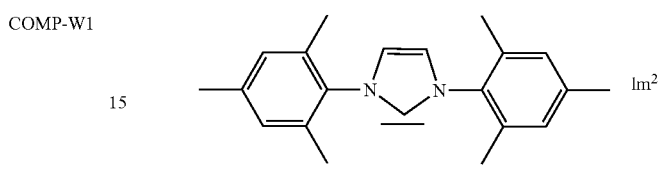

$Im^2$

These ruthenium complexes are generally less sensitive to atmospheric oxygen and tolerate both traces of moisture and also slight impurities. Of the ruthenium-alkylidene complexes COMP-RuA, those of the following formula COMP-Ru1 to COMP-Ru13 may be mentioned by way of example:

COMP-Ru1

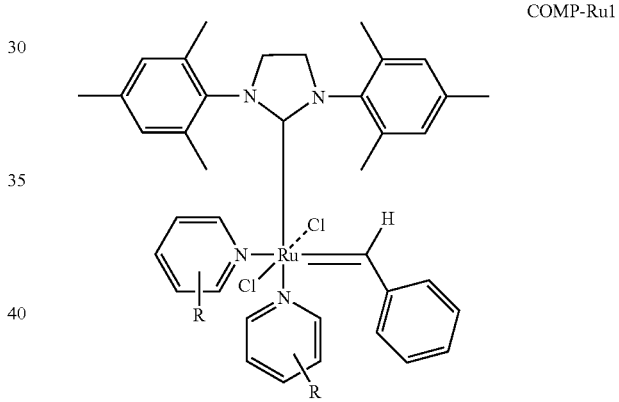

a: R = H
b: R = 3-Br
c: R = 4-phenyl

COMP-Ru2

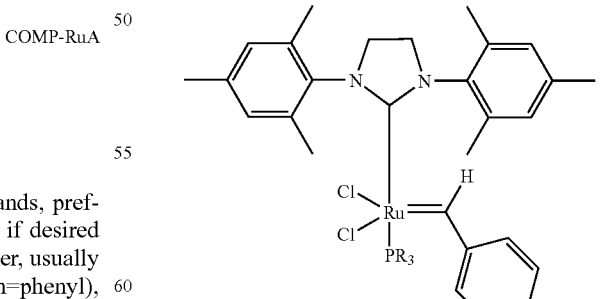

a: R = Cy
b: R = phenyl
c: R = p-$CF_3$-phenyl

-continued
COMP-Ru3
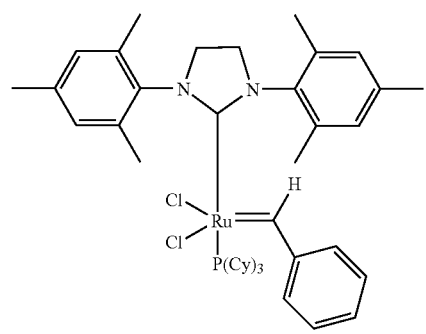
COMP-Ru4
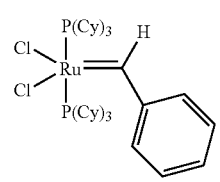
COMP-Ru5
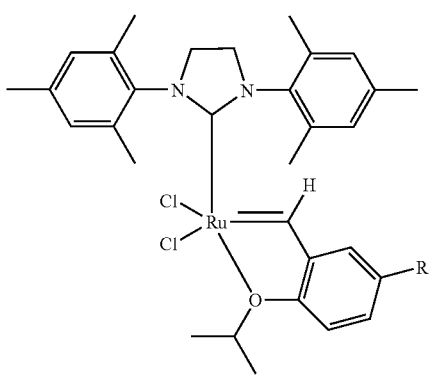
a: R = H
b: R = Br
c: R = NO₂
COMP-Ru6
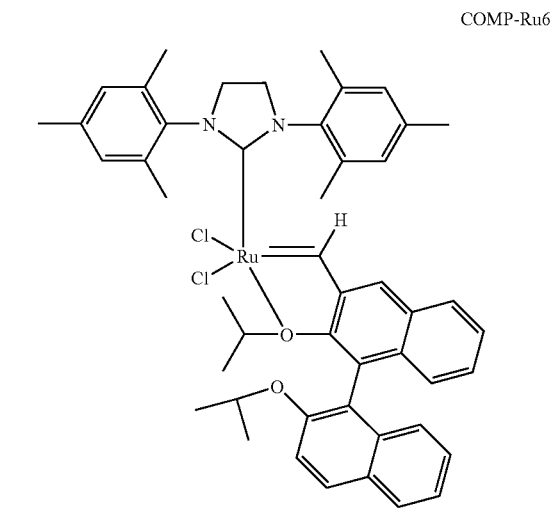
-continued
COMP-Ru7
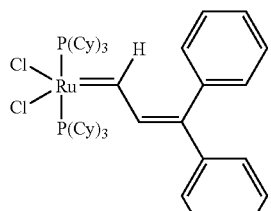
COMP-Ru8
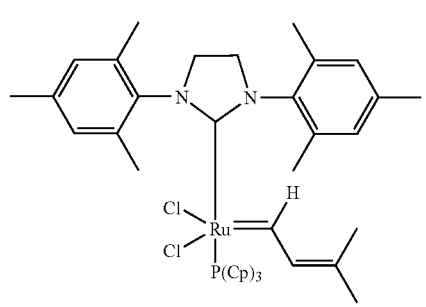
COMP-Ru9
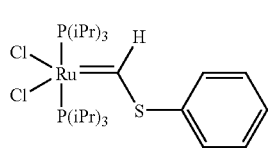
COMPU-Ru10
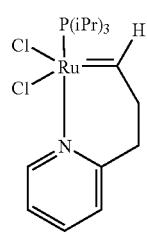
COMPU-Ru11
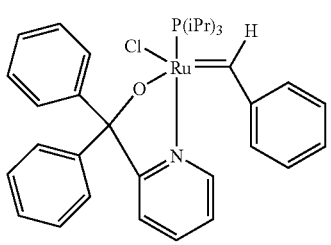
COMPU-Ru12
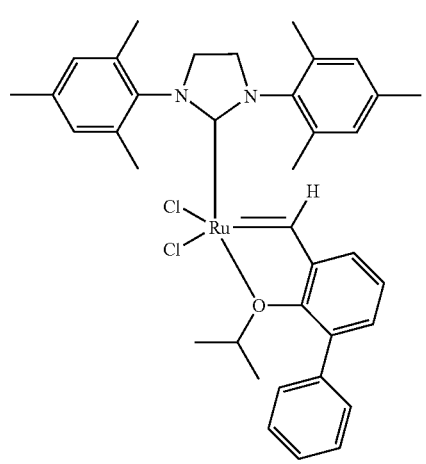

COMPU-Ru13

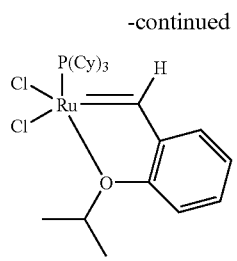

The alkylidene complexes employed as metathesis catalysts are either prepared by processes known from the literature (besides WO 96/04289, WO 97/06185, WO 99/00396, WO 99/00397, WO 99/29701, WO 99/51344, WO 00/15339, EP 1 022 282 A2, WO 00/58322, WO 00/71554, WO 02/14336, WO 02/14376, WO 02/083742, see, inter alia, also R. H. Grubbs and S. Chang, *Tetrahedron* 54 (1998) 4413; T. M. Trnka and R. H. Grubbs, Acc. Chem. Res. 2001, 34, 18; S. K. Armstrong, *J. Chem. Soc., Perkin Trans. I*, 1998, 371; A. Fürstner et al., *Chem. Eur. J.* 2001, 7, 3236; J. A. Love et al., Angew. Chem. 2002, 114, 4207; K. Grela et al., Angew. Chem. 2002, 114, 4210; G. S. Weatherhead et al., Tetrahedron Lett. 41 (2000) 9553, J. S. Kingsbury et al., J. Am. Chem. Soc. 1999, 121, 791, and the references indicated therein) or are commercially available, for example from Sigma-Aldrich, Inc. (USA), or Strem Chemicals Inc. (Kehl, Germany).

Some of these catalysts can also be attached to immobilising supports, for example made from polystyrene (for example COMP-Ru3: M. Ahmed et al., Synlett 2000, 1007; or COMP-Ru5a and complexes derived therefrom: St. Randl et al., Synlett 2001, 1547) or glass (for example COMP-Ru5 and complexes derived therefrom: J. S. Kingsbury et al., Angew. Chem. 2001, 113, 4381).

The catalyst used for the enyne metathesis step of the first process according to the invention is very particularly preferably a metal complex selected from the group consisting of complexes of the formulae COMP-Ru1, -Ru2, -Ru3, -Ru4, -Ru5, -Ru6, -Ru7, -Ru8, -Ru9, -Ru10, -Ru11, -Ru12, -Ru13, in particular of the formulae COMP-Ru2a, COMP-Ru3, COMP-Ru4, COMP-Ru5a and COMP-Ru13. The catalyst content is usually from 0.01 to 10 mol % (based on the enyne), preferably from 0.1 to 5 mol %, in particular from 0.5 mol % to 2.5 mol %.

The enyne metathesis of the process according to the invention is carried out under conventional conditions for metal complex-catalysed reactions of this type. The reaction is carried out without a solvent or in a suitable solvent. The solvent used is an inert solvent, preferably an aromatic and/or halogenated organic solvent and in particular toluene, benzene, chlorobenzene or dichloromethane. The reaction is generally carried out at temperatures from room temperature to the boiling point of the solvent (for example from about 20° C. to 40° C. (dichloromethane) or up to 80° C. or 110° C. (toluene)). Preference is given to reaction temperatures between 20 and 60° C. The reaction time is not crucial per se since the enyne metathesis generally proceeds with complete conversion of the starting material of the formula II and gives the desired pyran derivative of the formula I in good yields. The reaction duration is usually from 30 minutes to 8 days, preferably from 1 hour to 3 days, in particular from 4 hours to 24 hours, where the precise reaction time can be selected by the person skilled in the art depending on the particular catalyst, its amount and concentration and on the course of the reaction.

It is furthermore advantageous to add the catalyst to the reaction mixture in portions, which allows better control of the reaction and results in a reduction in the total amount of catalyst. It is furthermore advantageous in some cases to employ a cocatalyst, for example copper(I) bromide, in amounts of up to about 5 equivalents (based on the metathesis catalyst) in addition to the actual metathesis catalyst in the enyne metathesis.

The present invention furthermore relates to a second process according to the invention for the preparation of pyrans which is characterised by a process step which includes a cross metathesis reaction of a dihydropyran derivative of the general formula I-C with an alkene of the formula IIIa or IIIb

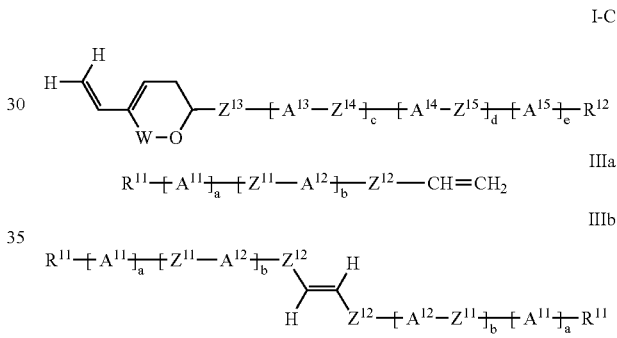

with formation of a pyran derivative of the formula I

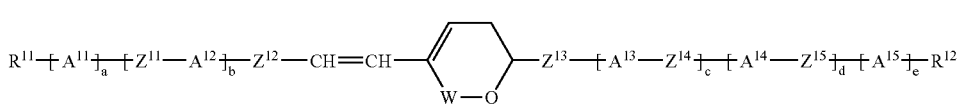

in the presence of a metathesis catalyst, where a, b, c, d, e, W, $R^{11}$, $R^{12}$, $Z^{11}$, $Z^{12}$, $Z^{13}$, $Z^{14}$, $Z^{15}$, $A^{11}$, $A^{12}$, $A^{13}$, $A^{14}$ and $A^{15}$ in the formulae I, I-C, IIIa and IIIb are as defined for the formula I above; with the proviso that, in the case of direct linking of $Z^{13}$ and $R^{12}$ to give -$Z^{13}$-$R^{12}$, $R^{12}$ is H, aralkyl or alkanyl if $Z^{13}$ is —C(=O)—, $R^{12}$ is aralkyl or alkanyl if $Z^{13}$ is —C(=O)—O—, and $Z^{13}$ is not —CH$_2$O— or —CF$_2$O—; that, in the case of direct linking of $Z^{14}$ and $R^{12}$ to give -$Z^{14}$-$R^{12}$, $R^{12}$ is H, aralkyl or alkanyl if $Z^{14}$ is —C(=O)—, $R^{12}$ is aralkyl or alkanyl if $Z^{14}$ is —C(=O)—O—, and $Z^{14}$ is not —CH$_2$O— or —CF$_2$O—; that, in the case of direct linking of $Z^{15}$ and $R^{12}$ to give -$Z^{15}$-$R^{12}$, $R^{12}$ is H, aralkyl or alkanyl if $Z^{15}$ is —C(=O)—, $R^{12}$ is aralkyl or alkanyl if $Z^{15}$ is —C(=O)—O—, and $Z^{15}$ is not —CH$_2$O— or —CF$_2$O—.

In general, the pyran derivative of the formula I is obtained predominantly or exclusively as the E isomer with respect to the exocyclic double bond.

The alkene of the formula IIIb has the trans-configuration at the central C=C double bond. In the metathesis reaction according to the invention, 1 mol-equivalent of this trans-alkene liberates 2 equivalents of a reactive intermediate (which may also be rewritten as "$R^{11}$-[-$A^{11}$-]$_a$-[-$Z^{11}$-$A^{12}$-]$_b$-$Z^{12}$-CH=") with breaking of the central C=C double bond, and this intermediate then reacts with 2 equivalents of the compound of the formula I-C. This means that, on use of an alkene of the formula IIIb in the process according to the invention, only 0.5 mol of the alkene of the formula IIIb has to be employed per mole of the pyran derivative of the formula I-C.

In connection with the present invention, the term "alkene of the formula III" or "compound of the formula III"—unless stated otherwise in an individual case—covers both alkenes of the formula IIIa and alkenes of the formula IIIb.

This second process according to the invention likewise allows the synthesis of pyran derivatives containing an exocyclic C=C double bond and having 2,5-disubstitution which have advantageous technical features, such as mesogenic properties, and/or can serve as starting compounds for the preparation of further compounds, for example mesogenic compounds, containing a central pyran ring, using the cross metathesis (CM) explained in general form above.

In a particularly preferred embodiment of the processes according to the invention, firstly, in an enyne metathesis reaction, a compound of the formula I-C is prepared, which is subsequently converted into the corresponding compound of the formula I according to the invention by cross metathesis according to the invention (where it is preferred that $R^{11}$ in the formula III and the formula I is then not H):

Scheme 3

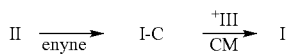

This reaction sequence according to the invention can be carried out as a "one-pot" synthesis, i.e. the enyne metathesis product I—C is not isolated, but instead the alkene III and, if desired, further metathesis catalyst are added directly. It is furthermore possible to add the alkene of the formula III to the starting reaction mixture comprising the enyne of the formula II and the metathesis catalyst without the formation of the compound of the formula I according to the invention via I-C being impaired to a significant extent; it appears that the enyne of the formula II undergoes an intramolecular reaction with formation of I-C significantly more quickly under the selected metathesis conditions than it undergoes an intermolecular reaction with the alkene III. In general, the reaction sequence is preferably carried out with isolation and, if desired, purification of the pyran derivative of the formula I-C before the further reaction.

The metathesis catalysts used for the cross metathesis are the same oxo-tungsten or transition-metal-alkylidene complexes employed for the enyne metathesis described above. The cross metathesis step of the second process according to the invention is particularly preferably carried out using a ruthenium-alkylidene complex, very particularly preferably selected from the group consisting of complexes of the formulae COMP-Ru1, -Ru2, -Ru3, -Ru4, -Ru5, -Ru6, -Ru7, -Ru8, -Ru9, -Ru10, -Ru11, -Ru12, -Ru13, in particular of the formulae COMP-Ru2a, COMP-Ru3, COMP-Ru4, COMP-Ru5a, COMP-Ru6 and COMP-Ru13. The catalyst content is usually from 0.01 to 10 mol % (based on compound I-C), preferably from 0.1 to 5 mol %, in particular from 0.5 mol % to 2.5 mol %.

The cross metathesis is carried out under conventional conditions for metal complex-catalysed reactions of this type. The reaction is carried out without a solvent or in a suitable solvent. The solvent used is an inert solvent, preferably an aromatic and/or halogenated organic solvent and in particular toluene, benzene, chlorobenzene or dichloromethane. The reaction is generally carried out at temperatures from room temperature to the boiling point of the solvent (for example from about 20° C. to 40° C. (dichloromethane) or up to 80° C. or 110° C. (toluene)). It can also be carried out without a solvent and, if desired, in an autoclave under increased pressure, for example at from 2 to 10 bar. The reaction time is not crucial per se since the cross metathesis generally proceeds with complete conversion of the starting material of the formula I-C and gives the desired pyran derivative of the formula I in good yields. The reaction duration is usually from 30 minutes to 8 days, preferably from 1 hour to 3 days, in particular from 4 hours to 24 hours, where the precise reaction time can be selected by the person skilled in the art depending on the particular catalyst, its amount and concentration and on the course of the reaction.

The alkenes of the formula III employed in the cross metathesis reaction of the process according to the invention are either commercially available or are prepared by methods known per se, as described in the literature (for example the standard works, such as Houben-Weyl, Methoden der Organischen Chemie [Methods of Organic Chemistry], Georg-Thieme-Verlag, Stuttgart), to be precise under reaction conditions which are known and suitable for the reactions mentioned therein. Use can also be made here of variants which are known per se, but are not mentioned here in greater detail.

In respect of the compounds of the formula I according to the invention which are lactones (compounds of the formula I-A), the enyne metathesis step of the processes according to the invention is carried out starting from the corresponding propiolic acid esters II-A. These are accessible as shown in scheme 4 by esterification of a commercially available activated propiolic acid derivative V-I (where, for example, X=methoxy, ethoxy, propoxy, t-butoxy, chlorine, bromine or anhydride radical, in particular acetoxy) using a corresponding homoallyl alcohol V-II (the preparation of which is shown below in scheme 5). This process step proceeds under conventional conditions for ester formation reactions of this type (cf., inter alia, J. March: Advanced Organic Chemistry; John Wiley & Sons, New York inter alia, 3rd Edn., 1985, pp. 346-351, 0-22, 0-23 and 0-24).

Scheme 4

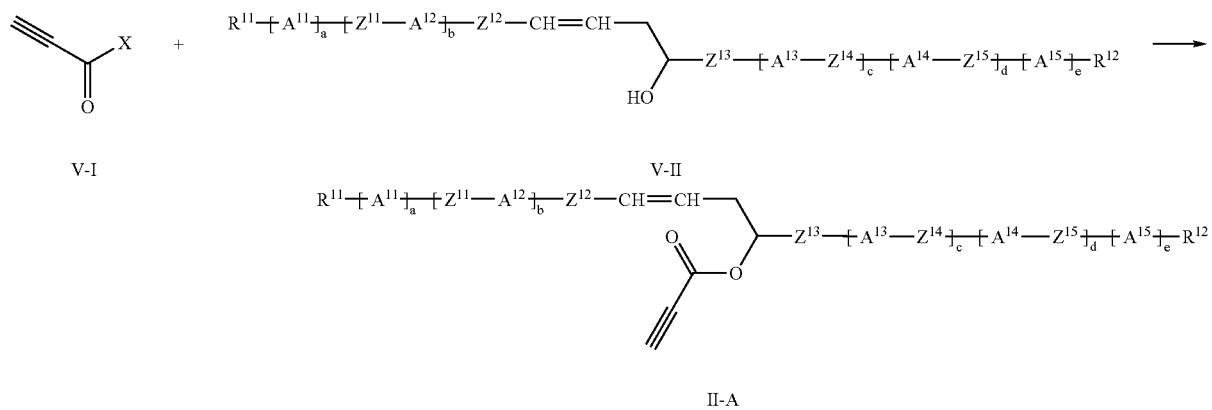

where a, b, c, d, e, $R^{11}$, $R^{12}$, $Z^{11}$, $Z^{12}$, $Z^{13}$, $Z^{14}$, $Z^{15}$, $A^{11}$, $A^{12}$, $A^{13}$, $A^{14}$ and $A^{15}$ are as defined for the formula I above, and X is as defined above and is preferably bromine or methoxy.

The homoallyl alcohols of the formula V-II and the propiolic acid esters of the formula II-A are themselves each a subject-matter of the present invention as useful intermediates for the synthesis of the compounds of the formula I according to the invention.

Lactones of the formula I-A where a=b=0, $Z^{11}$=single bond and $R^{11}$=H (which may also be depicted by the formula I-CA) can, if desired, be reacted with corresponding alkenes of the formula III in the cross metathesis step of the second process according to the invention to give the corresponding pyran derivatives of the formula I-A, where the resultant reaction products then have a substituent other than H on the exocyclic double bond in the formula I-A, as is the case, for example, for compounds of the formula I-DAA.

Furthermore, it is possible, on selection of suitable radicals, rings or functional groups for $R^{12}$, $A^{13}$, $A^{14}$, $A^{15}$, $Z^{13}$, $Z^{14}$ and $Z^{15}$, to introduce the "right-hand" side chain of the pyran derivative I-A ($-Z^{13}$-$[A^{13}$-$Z^{14}]_c$-$[A^{14}$-$Z^{15}]_d$-$[A^{15}]_e$-$R^{12}$) into the respective molecule in full or part after the ring-closing enyne metathesis. In principle, the same synthetic methods which are also used for the further derivatisation of the pyrans of the formula I-B according to the invention and are described in detail below are available here, where the person skilled in the art can readily carry out any adaptations necessary or advisable owing to the lactone function of the central O-heterocyclic ring.

For the compounds of the formula I-A (or of the formula I where W=—C(=O)—), it is furthermore preferred for a reduction reaction for conversion of the pyran derivative of the formula I in which W is —C(=O)— and $Z^{13}$, $Z^{14}$ and $Z^{15}$ are not —C(O)— into a pyran derivative of the formula I in which W is a methylene group (i.e. a pyran of the formula I-B) to be carried out as a further reaction step in the processes according to the invention after the respective metathesis reaction step. This reduction reaction can be carried out using suitable reducing agents, for example diisobutylaluminium hydride (DIBAH) or boron trifluoride etherate+lithium aluminium hydride or lithium borohydride or sodium borohydride (see J. March: Advanced Organic Chemistry; John Wiley & Sons, New York inter alia, 3rd Edn., 1985, p. 1100, 9-41). Other carboxyl functions (C(=O)O) present in the molecule are also reduced to ether functions ($CH_2O$) at the same time.

The starting compounds and precursors necessary for the preparation according to the invention of the compounds of the formula I according to the invention which are pyrans (compounds of the formula I-B) are accessible by various synthetic routes if they are not also commercially available. Some compounds of the formula I-B are prepared by chemical modification of other compounds of the formula I-B or—as stated above—by reduction of compounds of the formula I-A.

Thus, the starting compounds of the formula II where W=—$CH_2$— (=formula II-B), which are themselves a subject-matter of the present invention as useful intermediates for the preparation of the compounds of the formula I-B according to the invention, are generally accessible starting from compounds of the formula V-III in accordance with scheme 5. Instead of the allyl bromide V-III, it is possible to employ other allyl halides, in particular allyl chlorides.

Scheme 5

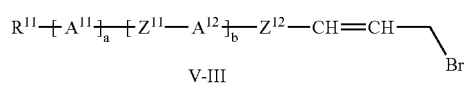

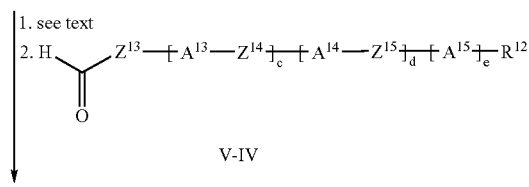

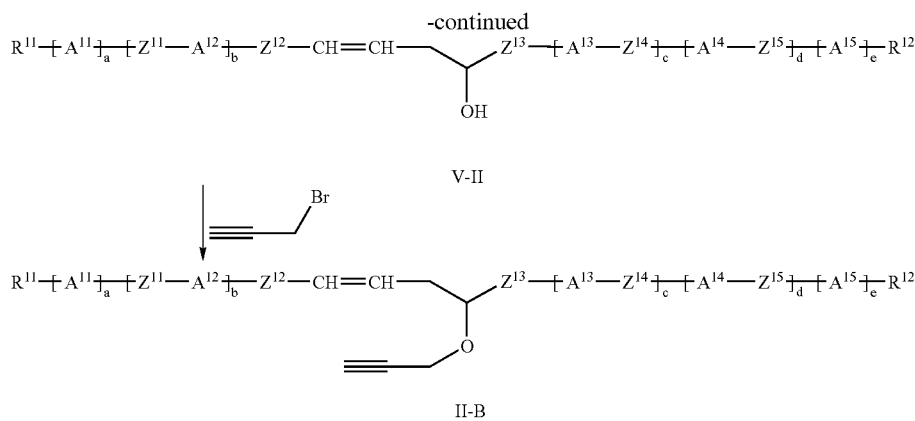

The requisite activation of the allyl bromide V-III (or corresponding allyl halides) in reaction step 1 can be carried out in various ways. For example, addition of V-III to indium powder in a suitable reaction medium, for example water or water/tetrahydrofuran, firstly forms a corresponding intermediate allylindium compound (by the method of T.-P. Loh et al., Tetrahedron Letters 42 (2001) 8701 and 8705) which reacts with the aldehyde V-IV in step 2 with formation of the corresponding homoallyl alcohol V-II. The allyl bromide V-III can also be converted into the corresponding intermediate allyllithium or allylmagnesium bromide compound using lithium or an organolithium base or using magnesium, usually in excess, or a reactive Grignard base with halogen-metal exchange, and this intermediate then reacts with the aldehyde V-IV to give the homoallyl alcohol V-II.

If the aldehyde V-IV additionally contains a functional group which is able to react with the allyl-Grignard or allyllithium compound like the aldehydic carbonyl function, for example an ester function or a nitrile function, it is advantageous to transmetallate the intermediate allyllithium or allylmagnesium bromide compound in a known manner using zinc or titanium salts, since the corresponding allylzinc or allyltitanium compounds only react chemoselectively with the aldehydic carbonyl function and not with the ester carboxyl or the CN function.

It is furthermore also possible to employ allyl derivatives of other metals and semimetals, for example allyl derivatives of chromium, tin, zinc, samarium, boron and silicon, for the preparation of the homoallyl compounds V-II according to the invention. Starting from allyl mesylates carrying a mesylate radical (—$OSO_2CH_3$) instead of bromine in the formula V-III, the corresponding allyl stannanes are accessible by transmetallation using, for example, LiSn(butyl)$_3$, and can also be prepared by reaction of the allyl bromide V-III with tin(II) chloride and potassium iodide in water (cf. V. V. Samoshin et al., Tetrahedron Lett. 43 (2002) 6329) or with tin metal under the action of ultrasound and water (cf. P. C. Andrews, Tetrahedron Lett. 43 (2002) 7541) and can be reacted with the aldehyde V-IV to give the homoallyl alcohol V-II. Correspondingly, allylzinc compounds are obtainable, inter alia, using zinc dust in tetrahydrofuran (cf. B. C. Ranu et al., Tetrahedron Lett. 36 (1995), 4885), allylsamarium compounds are obtainable using $SmI_2$ in tetrahydrofuran (cf. B. Hamann-Gaudinet et al., Tetrahedron Lett. 38 (1997) 6585) or allylchromium compounds, which can be reacted with an aldehyde V-IV to give homoallyl alcohols V-II, are obtainable using Cr(II)Cl$_2$/Mn.

The homoallyl alcohol V-II is then converted into the enyne II-B using propargyl bromide. The ether-formation reaction step is generally carried out under the conditions of the Williamson ether synthesis (see, for example, J. March: Advanced Organic Chemistry; John Wiley & Sons, New York inter alia, 3rd Edn., 1985, p. 342, 0-14), i.e. under basic reaction conditions and at temperatures of from room temperature to about 60° C. in suitable solvents, for example ethers, such as tetrahydrofuran (THF), methyl tertbutyl ether (MTBE), dioxane or dimethoxyethane. A particularly preferred variant of this reaction works with granulated NaOH and THF in the presence of a phase-transfer catalyst and a little water, with the propargyl bromide and the homoallyl alcohol of the formula V-II being warmed at from 40° C. to 60° C. for from 4 to 48 hours. This variant is particularly suitable for homoallyl alcohols of the formula V-II which do not contain a carboxyl function (i.e. homoallyl alcohols of the formula V-II in which $Z^{13}$, $Z^{14}$ and $Z^{15}$ are not $CO_2$). Alternatively, the base employed can be sodium hydride, preferably in an organic solvent.

The enyne of the formula II-B formed in this way is then—after any purification necessary—converted into the compound of the formula I-B according to the invention (=formula I where W=—$CH_2$—) in the enyne metathesis reaction of the first process according to the invention.

If commercially available allyl bromide is employed as starting compound V-III in the synthesis according to scheme 5 (i.e. a=b=0, $Z^{12}$=single bond and $R^{11}$=H in the formula V-III), the compounds of the formula I-C according to the invention are finally obtained via the corresponding enyne of the formula II-B by the enyne metathesis reaction. These compounds of the formula I-C can then be converted into the corresponding compounds of the formula I in the second process according to the invention using an alkene of the formula III via a cross metathesis reaction. This (convergent) procedure may under certain circumstances prove advantageous compared with the first process according to the invention (with a linear synthesis strategy) if, for example, the alkene III is more readily accessible than the substituted allyl bromide V-III.

Since the aldehydes of the formula V-IV have a prochiral centre on the carbonyl carbon atom, a centre of chirality is formed on the carbon atom carrying the hydroxyl function in the reaction with the activated allyl derivative formed from the compound of the formula V-II to give the homoallyl alcohol V-II. In general, a racemate of the optical antipodes of the homoallyl alcohol V-II forms in the process. However, it is also possible to prepare one of the optical isomers of the homoallyl alcohol V-II stereoselectively or alternatively to isolate it from the racemic mixture.

The stereoselective synthesis is preferably carried out by catalytic asymmetric allylation of the aldehyde of the formula V-IV using an allyltin compound derived from compound V-III, usually the corresponding allyltributyl-stannane, in the presence of a chiral catalyst. Suitable chiral catalysts are, in particular, complexes of chiral binaphthol (BINOL) compounds with zirconium (for example (R,R)- or (S,S)-BINOL-Zr(O-tert-butyl)$_4$: M. Kurosu et al., Tetrahedron Lett. 43 (2002) 1765) or titanium (for example bis(((S)(naphthoxy)(isopropoxy)titanium oxide: H. Hanawa et al., J. Am. Chem. Soc. 2003, 125, 1708) or corresponding boronates (cf., for example, S. Thormeier et al., J. Organomet. Chem. 657 (2002) 136). In principle, the R- or S-isomer is accessible selectively in this way—depending on the choice of the chiral catalyst.

The enantiomers are isolated from the racemic mixture by conventional methods, for example by crystallisation with a chiral base or chromatography on a chiral column material.

Through use of an enantiomerically pure homoallyl alcohol of the formula V-II accessible in this way, the corresponding pyran derivative of the formula I, which has a centre of asymmetry in the 2-position, is obtained in enantiomerically pure form via the intermediate II-A or II-B by the enyne metathesis according to the invention and, if desired, the cross metathesis reaction according to the invention. A further possibility for obtaining one of the optical antipodes of the pyran derivative of the formula I stereoselectively consists in the use of a chiral metathesis catalyst, for example COMP-Mo3 or COMP-Mo4, which have been described by G. S. Weatherhead et al., Tetrahedron Lett. 41 (2000) 9553, and have been employed for stereoselective ring-closing metathesis reactions.

The compounds of the formula V-III, if they are not commercially available, are accessible starting from the corresponding aldehydes of the formula

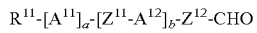  V-V:

a Wittig-Horner reaction (see, for example, J. March: Advanced Organic Chemistry; John Wiley & Sons, New York inter alia, 3rd Edn., 1985, p. 845, 6-47) with, for example, (ethyl-O)$_2$P(=O)CH$_2$CO$_2$-ethyl effects conversion into the ester R$^{11}$-[A$^{11}$]$_a$-[Z$^{11}$-A$^{12}$]$_b$-Z$^{12}$-CH=CH—CH$_2$CO$_2$-ethyl, which gives the desired allyl bromide V-III after reduction with, for example, DIBAH and bromination of the resultant allyl alcohol using, for example, bromine/triphenylphosphine.

The corresponding alkene of the formula III is also obtainable from the aldehyde of the formula V-V by the Wittig reaction (see, for example, J. March: Advanced Organic Chemistry; John Wiley & Sons, New York inter alia, 3rd Edn., 1985, p. 845, 6-47).

The aldehydes of the formula V-IV are known as such from the literature (see, for example, EP 0 122 389 A2). Aldehydes of the formula V-IV where Z$^{13}$=CF$_2$O are synthesised, for example, starting from the acid chloride ethyl-O—C(=O)—C(=O)—Cl   V-VI by reaction with firstly NaS—(CH$_2$)$_3$—SH. The resultant thiol thioester is reacted with trifluoromethanesulfonic acid (analogously to the processes described by P. Kirsch et al., Angew. Chem. 2001, 113, 1528, and WO 01/64667) to give the corresponding bis(alkylthio)carbenium salt

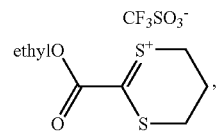   V-VII which is then subjected to oxidative fluorodesulfuration (as described by P.

Kirsch et al., Angew. Chem. 2001, 113, 1528, and WO 01/64667) by reacting the bis(alkylthio)carbenium salt of the formula V-VII firstly at low temperatures with NEt$_3$.3 HF (Et=ethyl) and an alcohol of the formula

   V-VIII, then with 1,3-dibromo-5,5-dimethylhydantoin (DBH) or N-bromosuccinimide (NBS) or bromine and finally with aqueous caustic lye to give the ester

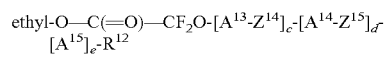   V-IX.

The final introduction of the aldehyde function to give the aldehyde of the formula V-IV is carried out either by direct reduction of the ester using a suitable reducing agent, such as diisobutylaluminium hydride, in an inert solvent, for example n-heptane, or via reduction of the ester to give the corresponding alcohol and subsequent oxidation to the aldehyde using a suitable oxidant, for example Dess-Martin reagent.

An alternative synthetic route which is suitable, in particular, for the preparation of aldehydes of the formula V-IV in which the difluorooxymethylene bridge is linked to an aromatic radical starts from the ester ethyl-O—C(=O)—CF$_2$Br, which is converted into the desired aldehyde V-IV using a suitable phenoxide in the presence of, for example, hexamethylenephosphoric tribromide or with Pd$^0$ complex catalysis with formation of the CF$_2$O bridge and after final reduction of the ester function.

If the aldehyde of the formula V-IV is a phenanthrene derivative of the formula

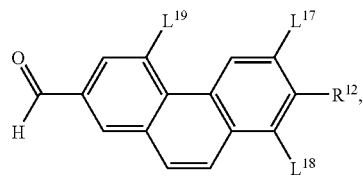

this is accessible in accordance with scheme 6 below:

Scheme 6

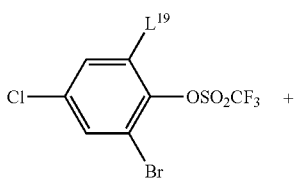

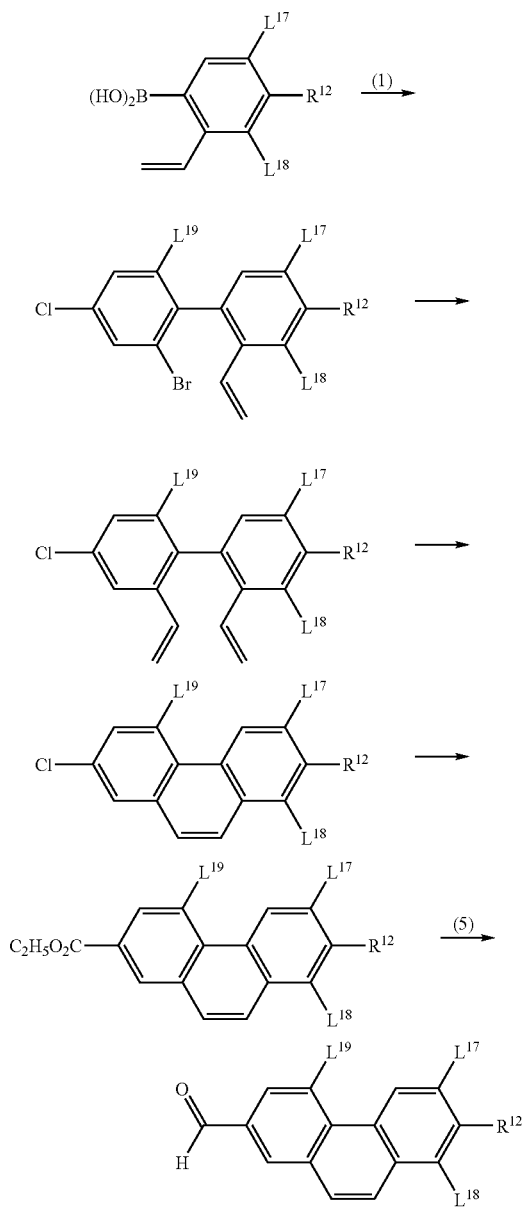

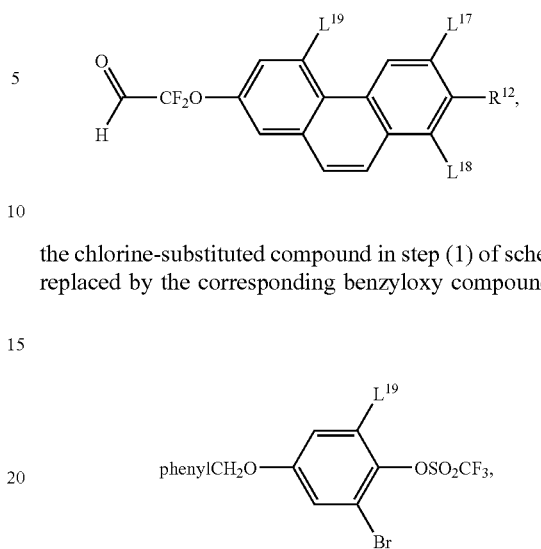

the chlorine-substituted compound in step (1) of scheme 6 is replaced by the corresponding benzyloxy compound which is correspondingly converted into the corresponding benzyloxy-substituted phenanthrene compound in steps (1) to (4). After reductive removal of the benzyloxy protecting group (using hydrogen and Pd/C), the resultant hydroxyphenanthrene is converted into the desired aldehyde as described above using ethyl-O—C(=O)—CF$_2$Br and after final reduction of the ester function. The starting compounds for these phenanthrene syntheses are either commercially available or readily accessible by known synthetic methods.

It goes without saying that on the one hand precursors and starting compounds of the formulae II-B and III for compounds of the formula I-B according to the invention can be prepared from other suitable precursors and starting compounds of the formulae II-B and III, and on the other hand compounds of the formula I-B according to the invention can also be converted into other pyran derivatives of the formula I-B according to the invention after ring closure. Carboxylic acid derivatives have proven particularly useful here.

If, for example, glyoxal ethyl ester is employed as aldehyde V-IV in the synthesis shown in scheme 5, the enyne of the formula II-B where $Z^{13}$-$R^{12}$=CO$_2$-ethyl is obtained. This ethyl enyne-carboxylate can then firstly be subjected to an enyne metathesis reaction with formation of the corresponding pyran derivative of the formula I-B (or—depending on the meaning of $R^{11}$, $A^{11}$, $A^{12}$, $Z^{11}$, $Z^{12}$, a and b—of the formula I-CBIIa or I-JB). Transesterification of the ester I-JB using synthetic units of the HO-[A$^{13}$-Z$^{14}$]$_c$-[A$^{14}$-Z$^{15}$]$_d$-[A$^{15}$]$_e$-R$^{12}$ type then enables other compounds of the formula I-B according to the invention to be obtained. However, a corresponding transesterification can also be carried out, if desired, before the enyne metathesis reaction with the precursor II-B.

If the glyoxalic acid ester is reacted with allyl bromide as allyl compound V-III, the cross metathesis reaction of 1-CBIIa with an alkene of the formula III, optionally followed by a further esterification, arises as a further synthetic route in addition to transesterification before the enyne metathesis or after the enyne metathesis to give the ester of the formula I-CBIIa.

In step (1), C-C coupling is carried out with Pd$^0$ catalysis to give the biphenyl, which is converted into the divinyl derivative in step (2) using vinylmagnesium bromide or vinylzinc bromide in the presence of a palladium complex (PdCl$_2$.dppf). In step (3), an intramolecular cross metathesis to give the phenanthrene derivative is carried out in the presence of a ruthenium-alkylidene complex COMP-RuA, preferably COMP-Ru2a-c or COMP-Ru4. The chlorophenanthrene is subsequently converted into the ethyl ester in step (4) using CO/ethanol at 70° C. and 5 bar in the presence of PdCl$_2$.[2P(cyclohexyl)$_3$] as catalyst, and this ethyl ester gives the desired phenanthrene aldehyde after final reduction using DIBAH in step (5). For the preparation of the phenanthrene aldehyde of the formula The carboxylic acids of the formulae I-CBIIa-1 and I-JB according to the invention where $R^{12}$=H, which are prepared from the corresponding esters by basic or acidic saponification, can be employed in order to obtain the corresponding $CF_2O$-bridged pyran derivative of the formula I-B (for example compounds of the formulae I-CBIII, I-DAB and I-HB) via the corresponding bis(alkylthio)carbenium salt followed by oxidative fluorodesulfuration (cf. WO 01/64667). The oxidative fluorodesulfuration can of course also be used for compounds of the formula I-B according to the invention in which the carboxyl function is not linked directly to the central pyran ring, i.e. if $Z^{14}$ or $Z^{15}$=-$CO_2$H; in this way, —$CF_2$O-$[A^{14}$-$Z^{15}]_d$-$[A^{15}]_e$-$R^{12}$- or —$CF_2$O-$A^{15}$-$R^{12}$— radicals respectively are then introduced.

Aldehydes according to the invention (formula I-B where $Z^{13}$-$R^{12}$=—C(=O)—H; for example I-CBIVa-1) are accessible from the carboxylic acid esters of the formulae I-CBIIa and I-JB according to the invention where $R^{12}$≠H either by direct reduction, for example using a suitable metal hydride, or in two steps by reduction to the primary alcohol followed by gentle oxidation using, for example, Dess-Martin reagent.

The corresponding compounds of the formula I-CBV (where $Z^{13}$=—CH=CH—) are accessible from the resultant aldehyde I-CBIVa-1, for example by means of the Wittig or Wittig-Horner reaction with molecules of the $R^x$-$[A^{13}$-$Z^{14}]_c$-$[A^{14}$-$Z^{15}]_d$-$[A^{15}]_e$-$R^{12}$ type (where $R^x$ is, for example, (phenyl)$_3$P=CH— or (ethyl-O)$_2$P(=O)—CH$_2$—). The compounds of the formula I-B according to the invention where $Z^{14}$-$R^{12}$ or $Z^{15}$-$R^{12}$=—CHO can also be prepared correspondingly and converted into those where $Z^{14}$ or $Z^{15}$=-CH=CH—.

The ketones according to the invention, for example of the formula I-CBIVa, are prepared, for example, by reaction of the carboxylic acid ester I-CBIIa-3 with a suitable organometallic reagent, for example with a compound $R^{12}$—Mg—Br by the Grignard method (see, for example, J. March: Advanced Organic Chemistry, John Wiley & Sons, New York inter alia, 3rd Edn., 1985, p. 434, 0-107). The other compounds of the formula I-CBIV are also accessible analogously by reaction with a suitable organometallic reagent Met*-$[A^{13}$-$Z^{14}]_c$-$[A^{14}$-$Z^{15}]_d$-$[A^{15}]_e$-$R^{12}$ (where "Met*" is, for example, Br—Mg or Li). If $Z^{14}$ and $Z^{15}$ are not $CO_2$ and $R^{12}$ does not contain a carboxyl function, the ketones of the formula I-CBIV are obtainable by reduction of the corresponding esters of the formula I-CBII. Keto functions can also be introduced analogously as $Z^{14}$ or $Z^{15}$.

Compounds of the formula I-RB according to the invention are also highly suitable for further derivatisations. Reaction with, for example, trimethylsilyl-1,3-dithiane in THF in the presence of n-butyllithium (in accordance with the method of J. Mlynarski and A. Banaszek, Tetrahedron 55 (1999) 2785) or analogously to the processes of P. Kirsch et al., Angew. Chem. 2001, 113, 1528, gives the corresponding ketene dithioketals (containing the structural unit

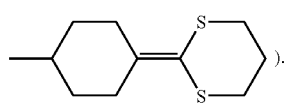).

Oxidative fluorodesulfuration (by the method of P. Kirsch et al., Angew. Chem. 2001, 113, 1528) then gives compounds of the formula I-B according to the invention containing

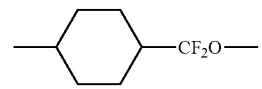

as structural unit.

The cyclohexanones of the formula I-RB according to the invention can also be reacted with a suitable Grignard reagent, for example of the Br—Mg-$Z^{14}$-$A^{14}$-$R^{12}$ type where $Z^{14}$ is, for example, —CH$_2$— or —CH$_2$CH$_2$—, to give the corresponding tertiary alcohols, in this example containing the structural unit

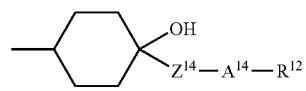

Subsequent reduction of the alcohol using triethylsilane and boron trifluoride etherate gives the corresponding 1,4-disubstituted cyclohexane derivative (in the example mentioned containing the structural unit

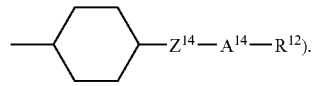

Compounds of the formula I according to the invention which contain a terminal phenyl ring where $R^{12}$=halogen, in particular bromine or iodine, for example corresponding compounds of the formula I-DABIa, I-DBBIa or I-K, can likewise be employed as starting compounds for the preparation of further compounds of the formula I according to the invention. Thus—after metallation with metal-halogen exchange, for example using an organometallic base, such as n-butyllithium—the intermediate metallated compound can be reacted further with various reagents, for example with $CO_2$ with formation of the corresponding carboxylic acid, with boric acid esters or related boron compounds with formation of the corresponding aryl boron compounds, or in the presence of suitable catalysts with reactants which undergo C—C cross-coupling reactions, for example of the Heck or Suzuki reaction type.

The said arylboron compounds or the halogenated compounds themselves can also be reacted in cross-coupling reactions of this type which are known from the literature (see, for example, N. Miyaura, A. Suzuki, Chem. Rev. 1995, 95, 2457). It should furthermore be noted that certain precursors and starting compounds of the processes according to the invention, for example those in which an aromatic ring $A^{13}$ is linked directly to an aromatic ring $A^{14}$ (or $A^{15}$) via $Z^{14}$ (or $Z^{15}$)=single bond, can also be prepared with the aid of these cross-coupling reactions.

It is furthermore preferred in the processes according to the invention, after the metathesis reaction step(s) and the optional reduction step of the lactone of the formula I-A to give the corresponding dihydropyran of the general formula I-B, to carry out, as a further reaction step, a catalytic hydrogenation to give a pyran of the general formula IV:

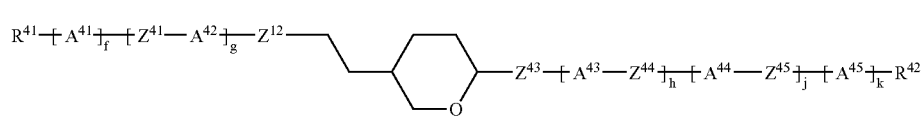

IV in which f, g, h, j and k are each, independently of one another, 0 or 1;

$R^{41}$ is H, a saturated alkyl radical having from 1 to 15 carbon atoms which is unsubstituted or mono- or polysubstituted, identically or differently, by halogen or —CN, where, in addition, one or more $CH_2$ groups in this radical may be replaced by —O—, —S—, —C(O)—O— and/or —O—C(O)— in such a way that hetero atoms (O and S) are not linked directly to one another;

$R^{42}$ is H, halogen, —CN, —NCS, aralkyl, —O-aralkyl or a saturated alkyl radical having from 1 to 15 carbon atoms which is unsubstituted or mono- or polysubstituted, identically or differently, by halogen or —CN, where, in addition, one or more $CH_2$ groups in this radical may be replaced by —O—, —S—, —C(O)—O— and/or —O—C(O)— in such a way that hetero atoms (O and S) are not linked directly to one another;

$Z^{41}$ and $Z^{42}$, independently of one another, are a single bond, —$CH_2$—, —$CH_2CH_2$—, —$CF_2CH_2$—, —$CH_2CF_2$— or —$CF_2CF_2$—;

$Z^{43}$, $Z^{44}$ and $Z^{45}$ are each, independently of one another, a single bond, —$CH_2CH_2$—, —$CF_2CH_2$—, —$CH_2CF_2$—, —$CF_2CF_2$—, —$CH_2O$—, —$CF_2O$—, —C(O)— or —C(O)—O—;

$A^{41}$ and $A^{42}$, independently of one another, are

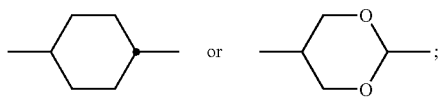

$A^{43}$ and $A^{44}$, independently of one another, are

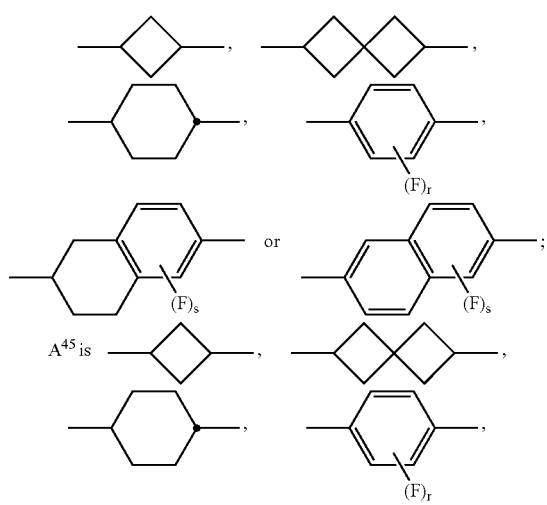

$A^{45}$ is

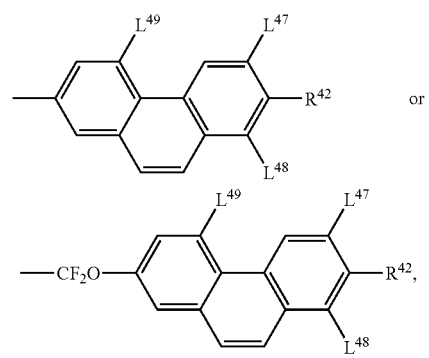

-continued

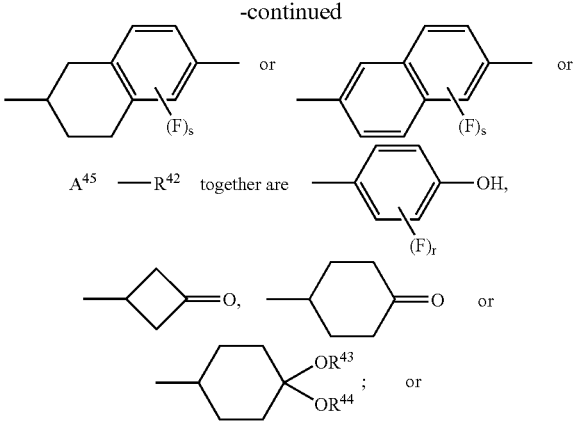

$Z^{43}$-[-$A^{43}$-$Z^{44}$-]$_h$[-$A^{44}$-$Z^{45}$-]$_j$-[-$A^{45}$-]$_k$-$R^{42}$ is where $R^{42}$ is as defined above, and $L^{47}$, $L^{48}$ and $L^{49}$, independently of one another, are H or F;

r is 0, 1, 2, 3 or 4;

s is 0, 1, 2 or 3;

$R^{43}$ and $R^{44}$, independently of one another, are an alkanyl radical having from 1 to 7 carbon atoms or together are an alkylene bridge having from 2 to 7 carbon atoms;

with the proviso that, in the case of direct linking of $Z^{43}$ and $R^{42}$ to give -$Z^{43}$-$R^{42}$, $R^{42}$ is H, aralkyl or alkanyl if $Z^{43}$ is —C(=O)—, $R^{42}$ is aralkyl or alkanyl if $Z^{43}$ is —C(=O)—O—, and $Z^{43}$ is not —$CH_2O$— or —$CF_2O$—;

that, in the case of direct linking of $Z^{44}$ and $R^{42}$ to give -$Z^{44}$-$R^{42}$, $R^{42}$ is H, aralkyl or alkanyl if $Z^{44}$ is —C(=O)—, $R^{42}$ is aralkyl or alkanyl if $Z^{44}$ is —C(=O)—O—, and $Z^{44}$ is not —$CH_2O$— or —$CF_2O$—;

that, in the case of direct linking of $Z^{45}$ and $R^{42}$ to give -$Z^{45}$-$R^{42}$, $R^{42}$ is H, aralkyl or alkanyl if $Z^{45}$ is —C(=O)—, $R^{42}$ is aralkyl or alkanyl if $Z^{45}$ is —C(=O)—O—, and $Z^{45}$ is not —CH$_2$O— or —CF$_2$O—.

Compounds of the formula IV are preferably mesogenic and in particular liquid-crystalline.

Starting compounds which can be employed for the preparation of a pyran of the general formula IV are in principle all compounds of the formula I according to the invention where W=—CH$_2$— (i.e. compounds of the formula I-B). Besides the (endocyclic) C=C double bond in the central pyran ring and the (exocyclic) C=C double bond on the central pyran ring, further aliphatic C=C double bonds optionally present in the compound of the formula I are also hydrogenated to a C—C single bond. Thus, for example, catalytic hydrogenation of a compound of the formula I-B can give the corresponding compound of the formula IV-B, where the meaning of f, g, h, j, k, $R^{41}$, $R^{42}$, $Z^{41}$, $Z^{42}$, $Z^{43}$, $Z^{44}$, $Z^{45}$, $A^{41}$, $A^{42}$, $A^{43}$, $A^{44}$ and $A^{45}$ corresponds to the meaning of a, b, c, d, e, $R^{11}$, $R^{12}$, $Z^{11}$, $Z^{12}$, $Z^{13}$, $Z^{14}$, $Z^{15}$, $A^{11}$, $A^{12}$, $A^{13}$, $A^{14}$ and $A^{15}$, with the proviso that, if $Z^{11}$, $Z^{12}$, $Z^{13}$, $Z^{14}$ and/or $Z^{15}$ are —CH=CH— or $R^{11}$ and/or $R^{12}$ contain a —CH=CH— group, these aliphatic —CH=CH— groups are converted into CH$_2$—CH$_2$ groups.

Analogously, the compounds of the formula I-CB according to the invention give the corresponding hydrogenated compounds IV-CB, I-DAB gives IV-DAB, I-DBB gives IV-DBB, I-DCB gives IV-DCB, I-EB gives IV-EB, I-FB gives IV-FB, I-GB gives IV-GB, I-HB gives IV-HB, I-JB gives IV-JB, I-KB gives IV-KB, I-LB gives IV-LB, I-MB gives IV-MB, I-NB gives IV-NB, I-OB gives IV-OB, I-PB gives IV-PB, I-QB gives IV-QB, I-RB gives IV-RB and I-SB gives IV-SB.

The catalytic hydrogenation is usually carried out at a hydrogen partial pressure of from 1 bar to 10 bar. The hydrogenation catalysts employed are usually transition-metal catalysts comprising nickel, platinum or palladium, such as, for example, Raney nickel, 5% or 10% platinum on carbon and 5% palladium on activated carbon, in a suitable solvent, such as, for example, n-heptane, toluene, ethyl acetate, ethanol, methanol or THF. The reaction time is not crucial per se; the hydrogenation is usually carried out to complete reaction of the respective starting compound. The reaction temperature is generally in the range between room temperature and 100° C.

In the hydrogenation of the pyran derivative I to the pyran derivative IV, a further chiral centre is formed in the 5-position in addition to the centre of asymmetry in the 2-position of the pyran ring. If the starting compound employed for the catalytic hydrogenation for formation of the tetrahydropyran IV is a pyran derivative of the formula I which, after corresponding stereoselective synthesis described above or purification, is in enantiomerically pure (or enantiomerically enriched) form, only 2 of the 4 theoretically conceivable diastereomers of IV are usually obtained (depending on the absolute configuration on the C-2 atom having the 2R,5R- and 2R,5S- or 2S,5R- and 2S,5S-configuration). These two isomers, which behave as diastereomers to one another, can be separated from one another by conventional methods, such as fractional crystallisation or chromatography, enabling the tetrahydropyran of the formula IV also to be obtained in enantiomerically pure form. The isomerically pure compounds of the formula IV, like the isomerically pure compounds of the formula I, are used, inter alia, as chiral dopants for nematic liquid-crystalline media which effect the twisted arrangement of the compounds present in the liquid-crystalline media which is necessary for various electro-optical applications.

It is of course possible for compounds of the formula IV themselves to be converted into other compounds of the formula IV, by means of the same synthetic processes explained in detail above, in particular for the compounds of the formula I-B. As also in the case of the compounds of the formula I-B according to the invention which contain a carboxyl function (for example I-CBIIa), carboxylic acid esters of the formula IV, in particular those of the formulae IV-CBIIa and IV-JB, are particularly suitable for this purpose. They can be saponified, for example, to give the corresponding free carboxylic acid, debenzylated by hydrogenation or desallylated with palladium catalysis and then further derivatised in order to facilitate, for example, the introduction of a difluorooxymethylene bridge. Of many other derivatisation possibilities, mention should also be made here of the possibility of reducing the ester of the formula IV-CBIIa (or of the formula IV-JB) to the corresponding aldehyde, which can itself be reacted via a Wittig or Wittig-Horner reaction with introduction of an aliphatic C=C double bond.

Furthermore, the compounds of the formula IV-RB are not only accessible directly by hydrogenation of corresponding compounds of the formula I-RB. They can also, for example, be prepared by firstly hydrogenating a pyran derivative of the formula I-B containing a terminal phenyl ring where $R^{12}$=O-aralkyl, such as, for example, compounds of the formula I-CBIa or I-DCBIa where $R^{12}$=O-aralkyl, with simultaneous debenzylation to give the corresponding compound of the formula IV-B containing a terminal phenol ring, and subsequently converted into the corresponding compound of the formula IV-RB containing a terminal cyclohexanone ring using suitable reducing agents (see, for example, J. March: Advanced Organic Chemistry; John Wiley & Sons, New York inter alia, 3rd Edn., 1985, p. 700, 5-11). For the illustrative compounds, this procedure is shown by scheme 7. The compounds of the formula IV-RB are particularly suitable for the introduction of CF$_2$O bridges, the details of which are described above for the reaction of the cyclohexanone derivatives of the formula I-RB, which are likewise in accordance with the invention.

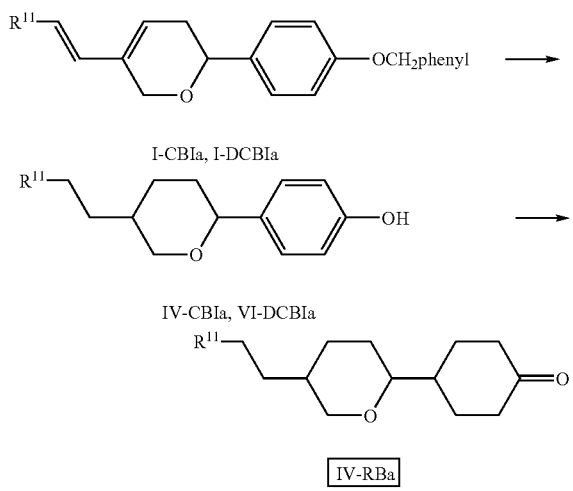

Scheme 7

Owing to the 2,5-disubstitution of the central pyran ring, the compound of the formula IV can be in the form of either the cis- or the trans-isomer. The trans-isomer, which is generally preferred for many uses, is occasionally obtained as the only hydrogenation product. If the pyran of the formula IV is formed predominantly as the cis-isomer or as a mixture of the two isomers, the preferred trans-isomer is obtained from the cis-isomer by treatment with a strong base, for example potassium tert-butoxide in N-methylpyrrolidone, or with a strong acid, for example sulfuric acid in dioxane.

The present invention furthermore relates to the use of a pyran derivative of the formula I above and preferably of the formula I-B or of the formula IV as constituent of a liquid-crystalline medium which is employed, in particular, in electro-optical display devices, such as TN, STN and active-matrix displays. These electro-optical display devices are, for example, displays of mobile radio equipment, screens of portable computers (notebooks) and TFT flat-panel screens.

Above and below, percentages are percent by weight. All temperatures are indicated in degrees Celsius. m.p. denotes melting point, cl.p. denotes clearing point. Furthermore, C=crystalline state, N=nematic phase, S=smectic phase and I=isotropic phase. $S_c$ denotes a smectic C phase, $S_B$ a smectic B phase, $S_A$ a smectic A phase. $\Delta n$ denotes the optical anisotropy ($\Delta n = n_e - n_o$, where $n_e$ denotes the refractive index of the extraordinary ray and $n_o$ denotes the refractive index of the ordinary ray) (589 nm, 20° C.). $\Delta \epsilon$ denotes the dielectric anisotropy ($\Delta \epsilon = \epsilon_\| - \epsilon_\perp$, where $\epsilon_\|$ denotes the dielectric constant parallel to the longitudinal molecular axes, and $\epsilon_\perp$ denotes the dielectric constant perpendicular thereto) (1 kHz, 20° C.). The optical data were measured at 20° C., unless expressly stated otherwise. The rotational viscosity $\gamma_1$ [mPa.s] was likewise determined at 20° C. The physical parameters were determined experimentally as described in "Licristal, Physical Properties Of Liquid Crystals, Description of the measurement methods", Ed. W. Becker, Merck KGaA, Darmstadt, revised edition, 1998, with the properties of individual compounds in some cases being determined after measurement of a defined amount of the compound (usually 5 or 10% by weight) in a defined host mixture having known properties followed by extrapolation.

The attached examples illustrate the present invention in greater detail without restricting it in any way.

EXAMPLES

The starting compounds, reagents and solvents employed in the illustrative syntheses were either purchased or prepared by processes known from the literature. The illustrative syntheses were usually carried out in dry apparatuses with exclusion of moisture and—if required by the reaction in question—also under a protective-gas atmosphere for exclusion of air.

The course of reactions was generally monitored by thin-layer chromatography or gas chromatography. The reaction products were worked up and purified by conventional methods, for example by column chromatography or crystallisation. Their structural identity was ensured by mass spectrometry and ¹H-NMR spectroscopy. Yields are not optimised.

Example 1

Enyne Metathesis Reaction

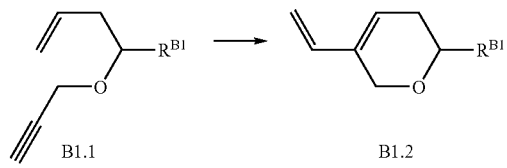

General Working Procedure B1 (GWP-B1)

Bis(tricyclohexylphosphine)benzylideneruthenium dichloride (COMP-Ru4) (0.5 mol; from Strem Chemicals Inc., Kehl, Germany) is added in portions at room temperature to starting compound B1.1 (1 mol), dissolved in dichloromethane, under a nitrogen atmosphere, and the mixture is stirred for 72 hours. The reaction mixture is concentrated and subjected to column chromatography on silica gel. The product B1.2 is recrystallised from heptane or ethanol and characterised by MS and ¹H-NMR. Yields: 50-75%.

The following compounds of the formula B1.2 with the meanings for $R^{B1}$ shown in Table B1 were prepared by GWP-B1:

TABLE B1

| Compound B1.2 No. | $R^{B1}$ |
|---|---|
| 1 | —⌬—Br |
| 2 | —⌬ (m-F) |
| 3 | —⌬ (3,4-diF) |
| 4 | —⌬ (3,4,5-triF) |
| 5 | —⌬—OCF₃ (3,5-diF) |
| 6 | —⌬—⌬ (3,4,5-triF) |

TABLE B1-continued
| Compound B1.2 No. | $R^{B1}$ |
|---|---|
| 7 | 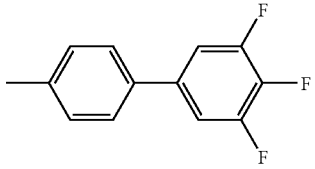 |
| 8 | 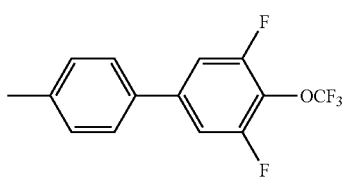 |
| 9 | 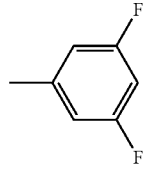 |
| 10 | 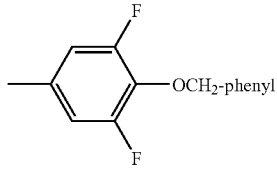 |
| 11 | 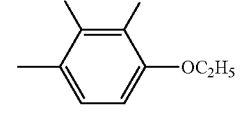 |
| 12 | 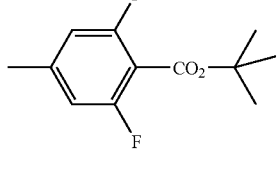 |
| 13 | 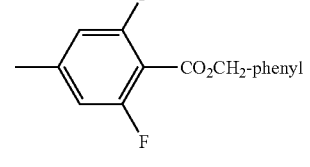 |
| 14 | 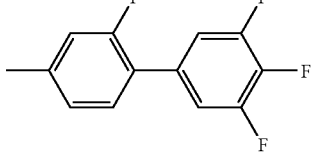 |
| 15 | 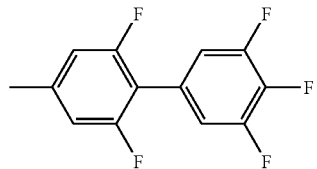 |
| 16 | 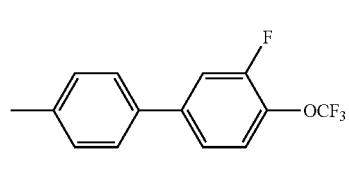 |
| 17 | 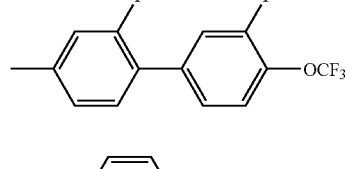 |
| 18 | 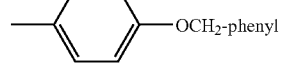 |
| 19 | 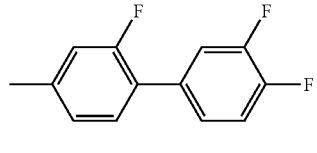 |
| 20 | 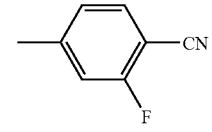 |
| 21 | 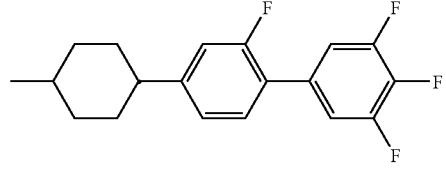 |
| 22 | 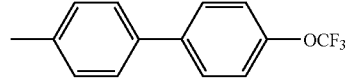 |
| 23 | 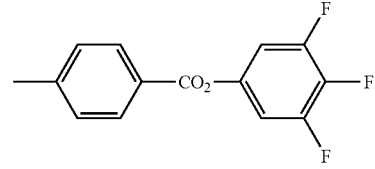 |

Example 2

Cross Metathesis Reaction

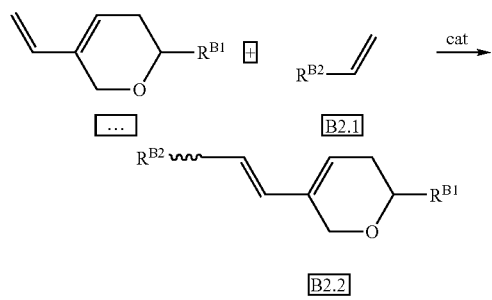

General Working Procedure B2a (GWP-B2a)

Starting compound B1.2 (0.05 mol) and tricyclohexylphospine(1,3-bis(2,4,6-trimethylphenyl)-4,5-dihydroimidazol-2-ylidenebenzylideneruthenium dichloride (COMP-Ru2) (0.001 mol; from Strem Chemicals Inc., Kehl, Germany) are dissolved in dichloromethane and then stirred with prop-1-ene (B2.1-1) at about 5 bar for 20 hours. The reaction mixture is concentrated and subjected to column chromatography on silica gel. The product B2.2 is obtained as the E-isomer and recrystallised from heptane or ethanol and characterised by MS and $^1$H-NMR. Yields: 45-75%. Instead of propene, it is also possible to employ trans-but-2-ene.

General Working Procedure B2b (GWP-B2b)

Starting compound B1.2 (0.05 mol), the alkene B2.1 (0.05 mol) and tricyclohexylphospine(1,3-bis(2,4,6-trimethylphenyl)-4,5-dihydroimidazol-2-ylidenebenzylideneruthenium dichloride (COMP-Ru2) or bis(tricyclohexylphosphine)benzylideneruthenium dichloride (COMP-Ru4) (0.01 mol; from Strem Chemicals Inc., Kehl, Germany) are dissolved in toluene and refluxed for from 24 to 48 hours. The reaction mixture is concentrated and subjected to column chromatography on silica gel. The product B2.2 is obtained as the E-isomer and recrystallised from heptane or ethanol and characterised by MS and $^1$H-NMR. Yields: 45-75%. Instead of the alkene B2.1 containing a terminal C=C double bond, it is also possible to employ the corresponding trans-alkene

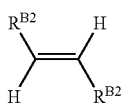

0.5 equivalent, based on the pyran derivative B1.2).

The compounds shown in Table B2 were prepared by GWP-B2a or GWP-B2b:

TABLE B2

| Compound B1.2 No. | Alkene B2.1 No. | Catalyst | Product B2.2 No. | $R^{B1}$ | $R^{B2}$ |
|---|---|---|---|---|---|
| 1 | 1 | COMP-Ru2 | 1 | —⟨phenyl⟩—Br | $CH_3$— |
| 1 | 2 | COMP-Ru2 | 2 | —⟨phenyl⟩—Br | $n\text{-}C_4H_9$— |
| 4 | 3 | COMP-Ru2 or COMP-Ru4 | 3 | —⟨2,3,4-trifluorophenyl⟩ | $n\text{-}C_3H_7$—⟨cyclohexyl⟩— |
| 6 | 4 | COMP-Ru2 | 4 | —⟨cyclohexyl⟩—⟨3,4,5-trifluorophenyl⟩ | $n\text{-}C_3H_7$ |
| 5 | 3 | COMP-Ru4 | 5 | —⟨2,6-difluoro-4-OCF3-phenyl⟩ | $n\text{-}C_3H_7$—⟨cyclohexyl⟩— |

TABLE B2-continued

| Compound B1.2 No. | Alkene B2.1 No. | Catalyst | Product B2.2 No. | R^{B1} | R^{B2} |
|---|---|---|---|---|---|
| 7 | 1 | COMP-Ru2 | 6 | 4'-methyl-3,4,5-trifluorobiphenyl group | CH$_3$ |
| 8 | 1 | COMP-Ru2 | 7 | 4'-methyl-3,5-difluoro-4-trifluoromethoxybiphenyl group | CH$_3$ |
| 6 | 1 | COMP-Ru2 | 8 | 4-methylcyclohexyl-3,4,5-trifluorophenyl group | CH$_3$ |
| 14 | 1 | COMP-Ru2 | 9 | 4'-methyl-2',3,4,5-tetrafluorobiphenyl group | CH$_3$ |
| 16 | 1 | COMP-Ru2 | 10 | 4'-methyl-3-fluoro-4-trifluoromethoxybiphenyl group | CH$_3$ |
| B3.1–5 | 1 | COMP-Ru2 | 11 | 4'-methyl-3,5-difluoro-4-(difluoromethyleneoxy-3,4,5-trifluorophenyl)biphenyl group | CH$_3$ |
| 19 | 1 | COMP-Ru2 | 12 | 4'-methyl-2',3,4-trifluorobiphenyl group | CH$_3$ |
| 21 | 1 | COMP-Ru2 | 13 | 4-methylcyclohexyl-2-fluoro-3',4',5'-trifluorobiphenyl group | CH$_3$ |
| 20 | 1 | COMP-Ru2 | 14 | 4-methyl-2-fluorobenzonitrile group | CH$_3$ |

TABLE B2-continued

| Compound B1.2 No. | Alkene B2.1 No. | Catalyst | Product B2.2 No. | $R^{B1}$ | $R^{B2}$ |
|---|---|---|---|---|---|
| Analogous to B3.1–5 | 1 | COMP-Ru2 | 15 | 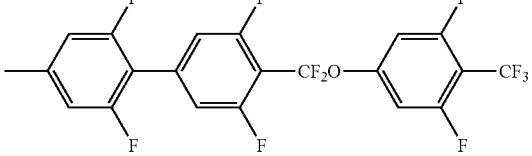 | CH₃ |
| Analogous to B3.1–5 | 1 | COMP-Ru2 | 16 | 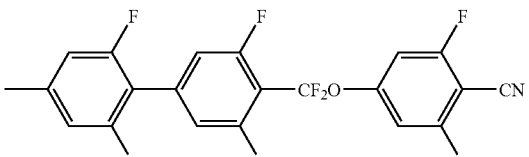 | CH₃ |
| Analogous to B3.1–5 | 1 | COMP-Ru2 | 17 | 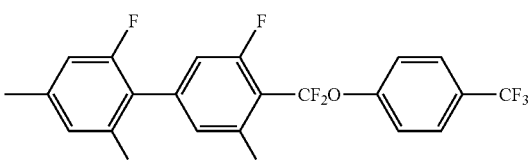 | CH₃ |
| Analogous to B3.1–5 | 1 | COMP-Ru2 | 18 | 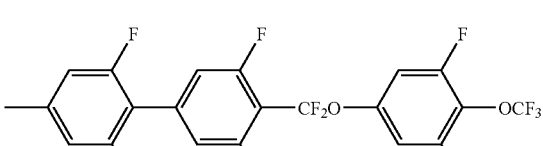 | CH₃ |
| Analogous to B3.1–5 | 1 | COMP-Ru2 | 19 | 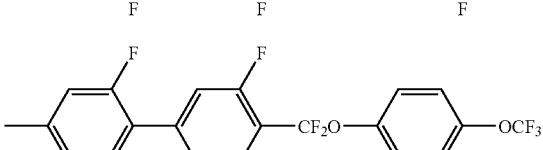 | CH₃ |

Example 3

Derivatisations a)

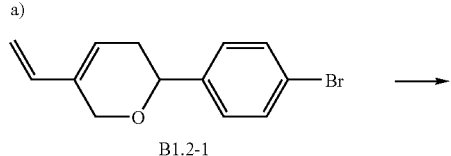

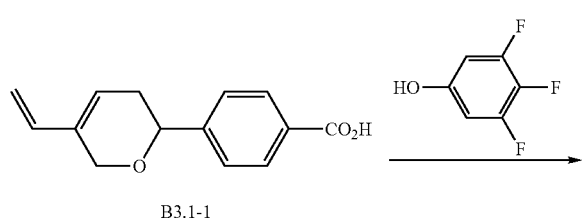

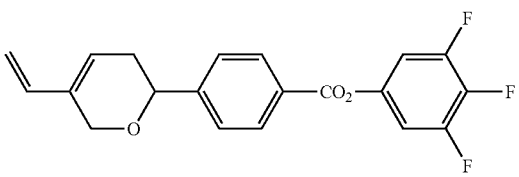

General Working Procedure B3a (GWP-B3a)

Compound B1.2-1 (0.3 mol) is dissolved in THF and cooled to −78° C. A 15% solution of n-butyllithium in n-hexane (0.3 mol) is added dropwise. The mixture is stirred for a further hour and then poured onto anhydrous solid carbon dioxide (about 6 mol) and subjected to aqueous acidic work-up. The organic phase is concentrated, and the crude product B3.1-2 is recrystallised from acetone. Yield: 62%.

N,N-dicyclohexylcarbodiimide (76 mmol) is added dropwise with water-bath cooling to a solution of B3.1-1 (68 mmol), 3,4,5-trifluorophenol (68 mmol) and 4,4-dimethylaminopyridine (DMAP) (2 mmol) in toluene. The mixture is stirred at room temperature for a further 18 hours, oxalic acid dihydrate (10 mmol) is then added, and the mixture is stirred for 1 hour. After filtration, the reaction mixture is concentrated and chromatographed on silica gel. The crude product B3.1-2 is recrystallised from acetone. Yield: 80%.

b)

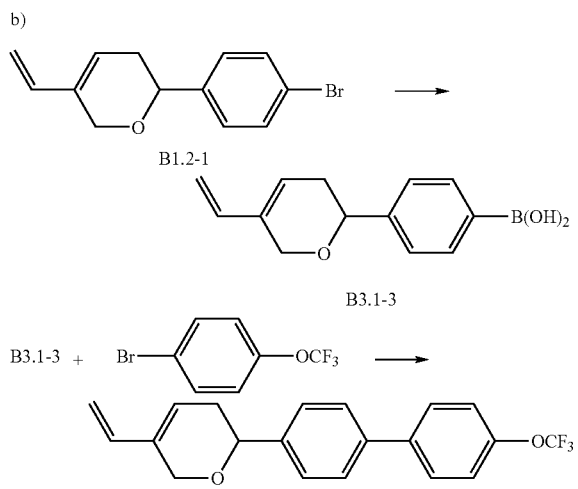

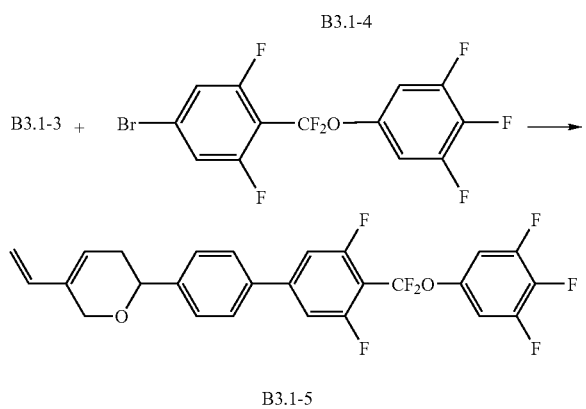

General Working Procedure B3b (GWP-B3b)

Bromoethane (15 mmol) and a few drops of a solution of compound B1.2-1 in THF are added to magnesium turnings (0.3 mol) in boiling THF; the remaining solution of compound B1.2-1 (a total of 0.3 mol) in THF is subsequently added dropwise under reflux. When the addition is complete and the mixture has been stirred for a further 1 hour, this reaction solution is added dropwise at −10° C. to a solution of trimethyl borate (0.36 mmol) in heptane. The pH is adjusted to 5 using hydrochloric acid, and the mixture is subjected to aqueous work-up. The crude product B3.1-3 is dried and evaporated and recrystallised from heptane. Yield: 82-96%.

A solution of sodium metaborate octahydrate (75 mmol), bis(triphenylphosphine)palladium(II) chloride (2 mmol) and hydrazinium hydroxide (2 mmol) in water/THF is prepared. Compound B3.1-3 (100 mmol) and the aryl bromide (100 mmol) are added to this solution, which is heated at the boil for 3 hours. Aqueous work-up and chromatography on silica gel gives compound B3.1-4 (30% yield) or B3.1-5 (35% yield). Further compounds having different substitution patterns on the phenyl rings whose structure can be seen, inter alia, in Table B2, are accessible analogously.

Example 4

Hydrogenations

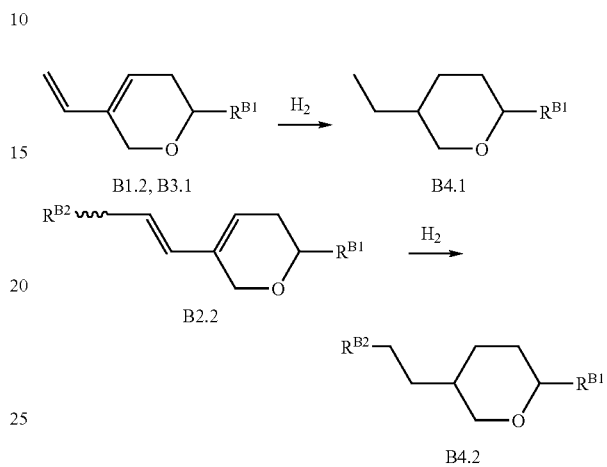

General Working Procedure B4 (GWP-B4)

The compounds B1.2, B3.1 and B2.2 are hydrogenated in the presence of 5% platinum on carbon or 5% palladium on carbon (about 10% by weight, based on the compound to be hydrogenated) in heptane or tetrahydrofuran at a hydrogen pressure of from 1 to 10 bar to give the corresponding compounds B4.1 and B4.2 respectively. After conventional work-up, the desired trans-pyran isomer is obtained by column chromatography, distillation or recrystallisation and, if necessary, after isomerisation using 30 mol % of potassium tert-butoxide in N-methylpyrrolidone with cooling and stirring and subsequent neutralisation. Tables B3 and B4 show the corresponding compounds.

TABLE B3

| Product B4.1 No. | $R^{B1}$ |
|---|---|
| 1 | ![](—⟨ ⟩—Br) |
| 2 | ![](—⟨ ⟩ with F,F,F) |
| 3 | ![](—⟨ ⟩ with F,F,OCF3,F) |

TABLE B3-continued
| Product B4.1 No. | $R^{B1}$ |
|---|---|
| 4 | 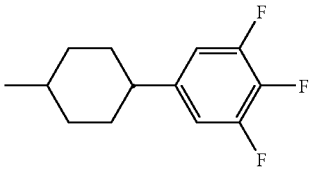 |
| 5 | 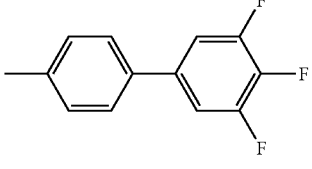 |
| 6 | 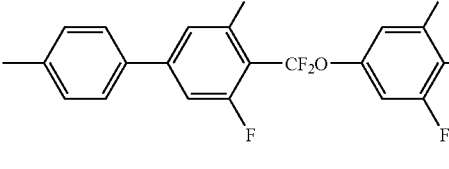 |
| 7 | 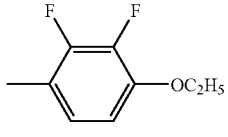 |
| 8 | 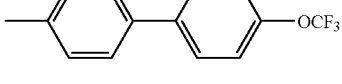 |
| 9 | 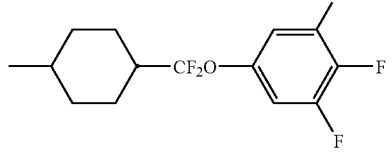 |
| 10 | 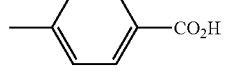 |
| 11 | 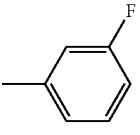 |
| 12 | 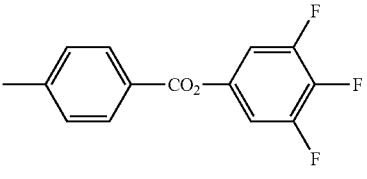 |
| 13 | 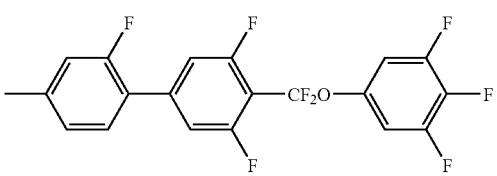 |
| 14 | 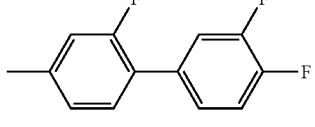 |
| 15 | 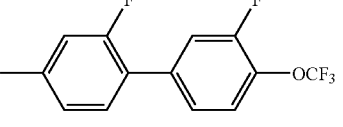 |
| 16 | 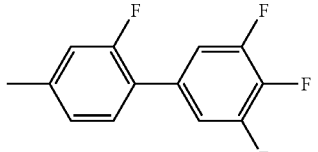 |
TABLE B4
| Product B4.2 No. | $R^{B1}$ | $R^{B2}$ |
|---|---|---|
| 1 | | |
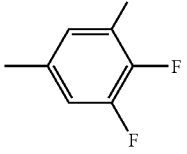

TABLE B4-continued

| Product B4.2 No. | $R^{B1}$ | $R^{B2}$ |
|---|---|---|
| 2 | (cyclohexyl)-(3,4,5-trifluorophenyl) | n-C$_3$H$_7$ |
| 3 | (cyclohexyl)-(3,4,5-trifluorophenyl) | n-C$_4$H$_9$ |
| 4 | (phenyl)-(3,4,5-trifluorophenyl) | CH$_3$ |
| 5 | (phenyl)-(3,5-difluoro-4-trifluoromethoxyphenyl) | CH$_3$ |
| 6 | (cyclohexyl)-(3,4,5-trifluorophenyl) | CH$_3$ |
| 7 | (cyclohexyl)-CF$_2$O-(3,4,5-trifluorophenyl) | CH$_3$ |
| 8 | (phenyl)-(3,4-difluorophenyl) | CH$_3$ |
| 9 | (phenyl)-(3-fluoro-4-trifluoromethoxyphenyl) | CH$_3$ |
| 10 | (cyclohexyl)-CF$_2$O-(3,4-difluorophenyl) | CH$_3$ |

TABLE B4-continued
| Product B4.2 No. | R^{B1} | R^{B2} |
|---|---|---|
| 11 | 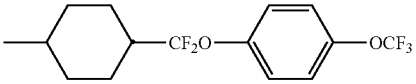 | $CH_3$ |
| 12 | 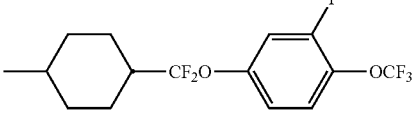 | $CH_3$ |
| 13 | 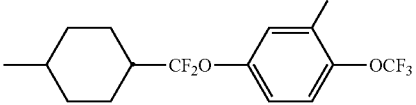 | $C_2H_5$ |
| 14 | 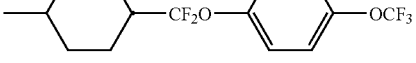 | $C_2H_5$ |
| 15 | 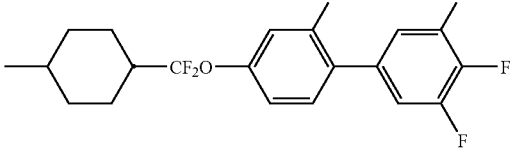 | $CH_3$ |
| 16 | 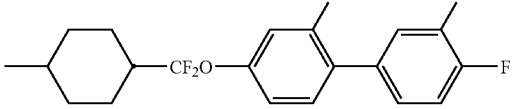 | $CH_3$ |
| 17 | 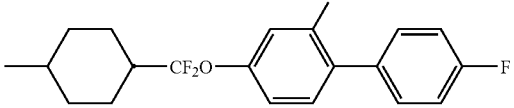 | $CH_3$ |
| 18 | 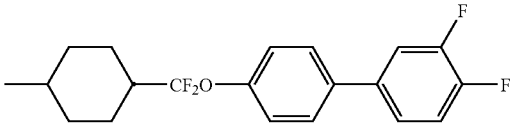 | $CH_3$ |
| 19 | 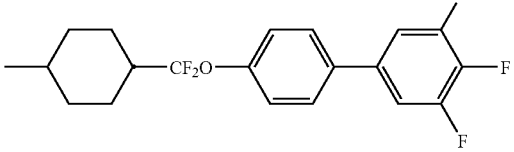 | $CH_3$ |
| 20 | 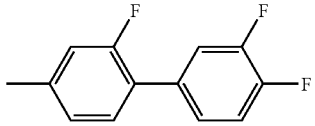 | $CH_3$ |

TABLE B4-continued
| Product B4.2 No. | $R^{B1}$ | $R^{B2}$ |
|---|---|---|
| 21 | 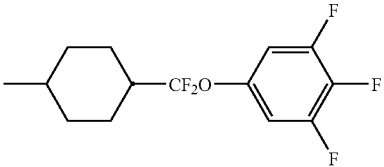 | n-C$_3$H$_7$ |
| 22 | 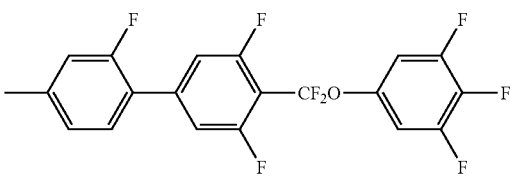 | CH$_3$ |
| 23 | 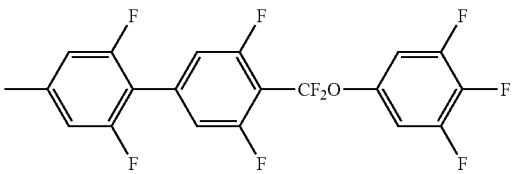 | CH$_3$ |
| 24 | 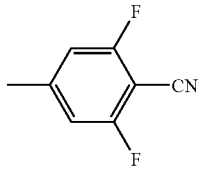 | CH$_3$ |
| 25 | 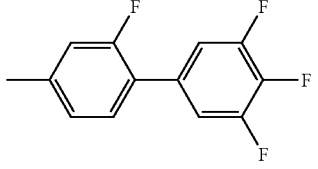 | CH$_3$ |
| 26 | 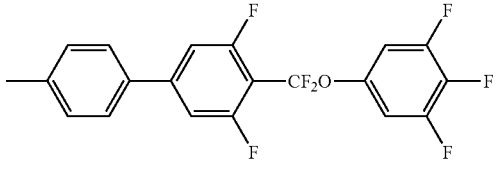 | CH$_3$ |
| 27 | 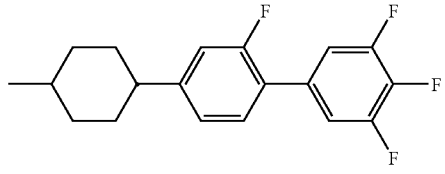 | CH$_3$ |
| 28 | 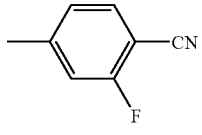 | CH$_3$ |

TABLE B4-continued

| Product B4.2 No. | $R^{B1}$ | $R^{B2}$ |
|---|---|---|
| 29 | ![structure with 2,6-difluorophenyl-3,5-difluorophenyl-CF2O-3,5-difluoro-4-CF3-phenyl] | $CH_3$ |
| 30 | ![structure with 2,6-difluorophenyl-3,5-difluorophenyl-CF2O-2,6-difluoro-4-CN-phenyl] | $CH_3$ |
| 31 | ![structure with 2,6-difluorophenyl-3,5-difluorophenyl-CF2O-4-CF3-phenyl] | $CH_3$ |
| 32 | ![structure with 2,6-difluorophenyl-3,5-difluorophenyl-CF2O-3,5-difluoro-4-OCF3-phenyl] | $CH_3$ |
| 33 | ![structure with 2,6-difluorophenyl-3,5-difluorophenyl-CF2O-4-OCF3-phenyl] | $CH_3$ |

Example 5

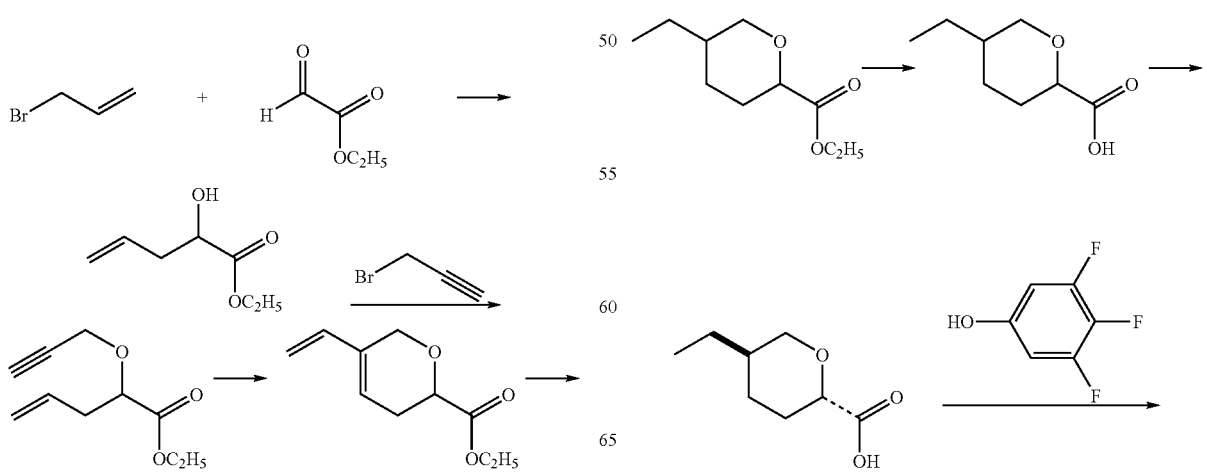

-continued

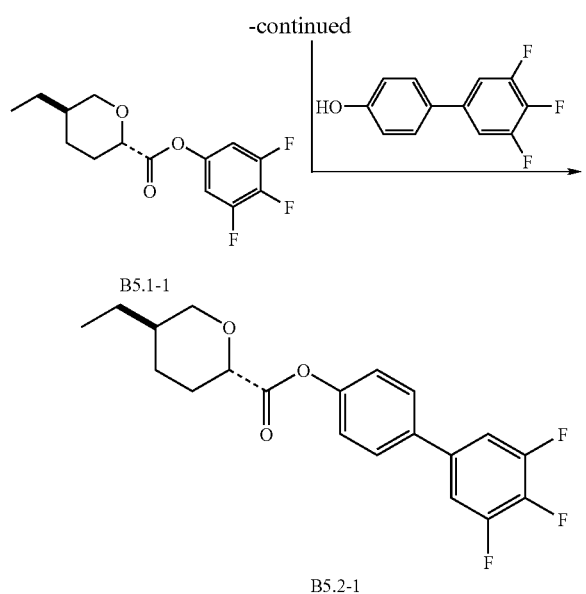

B5.1-1

B5.2-1

Indium powder (200 mmol) is initially introduced in water, and ethyl glyoxalate (400 mmol) is added. Allyl bromide (600 mmol) is added dropwise with stirring. After the mixture has been stirred overnight, ethyl acetate (300 ml) is added, and the mixture is again stirred for 30 minutes. The aqueous phase is extracted with ethyl acetate. After the combined organic phases have been dried, the solution is concentrated, giving the α-hydroxy ester (yield 44%) in a purity which is adequate for the further reaction.

Alternatively, the glyoxalic acid ester is initially introduced in toluene/water, indium powder and allyl bromide are added successively, and the mixture is stirred. Work-up, drying and concentration gives the α-hydroxy ester, which is employed in the next reaction step without further purification.

Ethyl 2-hydroxypent-4-enoate (139 mmol) is dissolved in toluene, and sodium hydride (139 mmol) is added in portions at −20° C. After the mixture has been stirred for 1 hour, propargyl bromide (146 mmol) is added. The mixture is warmed to room temperature and re-cooled to −20° C., moist THF is added, and the mixture is extracted with diethyl ether. Drying, evaporation and vacuum distillation gives the desired propargyl ether as a racemic mixture of the enantiomers.

Bis(tricyclohexylphosphine)benzylideneruthenium dichloride COMP-Ru4 (1 mmol) in dichloromethane is added to ethyl 2-propynyloxypent-4-ene-carboxylate (64 mmol) under an inert-gas atmosphere, and the mixture is stirred for 8 days. The reaction mixture is chromatographed on silica gel, giving the desired dihydropyran ester. This is hydrogenated with catalysis by Raney nickel. The hydrogenated ester is saponified using sodium hydroxide to give 1,4-dioxane, and the cis/trans isomer mixture of 5-ethyltetrahydropyran-2-carboxylic acid is isomerised to the trans product in the KOH melt. After recrystallisation from toluene, the ester B5.1-1 is obtained with 3,4,5-trifluorophenol in the presence of dicyclohexylcarbodiimide and DMAP or the ester B5.2-1 is obtained with 3,4,5-trifluoro-4'-hydroxybiphenyl.

Alternatively, the enyne metathesis is carried out in the presence of 1 mmol of COMP-Ru4 and 5 mmol of copper(I) bromide as cocatalyst.

Example 6

Precursors a1)

a) General Working Procedure B6a1 (GWP B6a1)

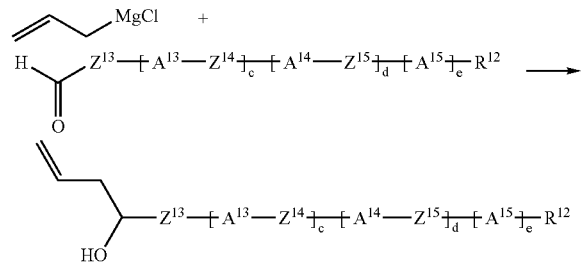

The aldehyde, dissolved in 100 ml of THF, is added dropwise with gentle ice cooling to 200 ml (2 mol) of allylmagnesium chloride in diethyl ether (Aldrich Co.), and the mixture is then stirred at room temperature for 4 hours. The reaction mixture is subsequently poured into 100 ml of 0.5 N HCl and stirred for five minutes. The organic phase is separated off, and the aqueous phase is extracted twice with methyl tert-butyl ether. The combined organic extracts are rinsed with water, dried, filtered and evaporated. The crude product obtained quantitatively can, owing to its purity, be used directly in the subsequent reaction.

a2)

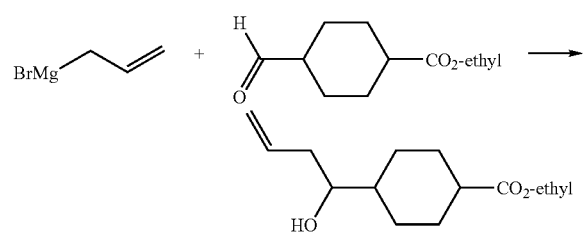

General Working Procedure B6a2 (GWP-B6a2)

Allylmagnesium bromide in ether (3.1 mol; from Sigma-Aldrich Co.) is initially introduced under an inert-gas atmosphere, and a solution of zinc bromide (3.1 mol) in tetrahydrofuran is added dropwise with cooling at about 10° C. The resultant suspension is stirred further at this temperature, and a solution of the aldehyde (3.1 mol) in diethyl ether is then added dropwise. The mixture is stirred overnight and then poured into dilute hydrochloric acid and subjected to aqueous work-up. The organic phase is dried and concentrated to give an oil, which is employed without further purification for the preparation of the corresponding propargyl ether. Yield: 82%. Further homoallyl alcohols of the general formula V-II according to the invention are prepared correspondingly.

This reaction procedure with transmetallation is particularly suitable for the reaction of aldehydes which contain a functional group which is reactive towards Grignard reagents, such as a carboxylate or nitrile group, in addition to the aldehydic carbonyl function. The transmetallation is generally superfluous if a carboxyl or nitrile group functionality is not present in the particular aldehyde, and can therefore be omitted for economic reasons.

b)

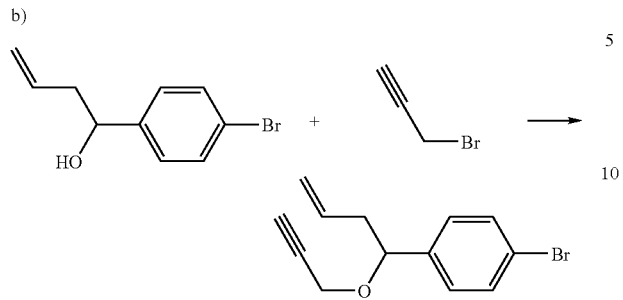

General Working Procedure B6b (GWP-B6b)

Solid sodium hydroxide (1.6 mol) is initially introduced in tetrahydrofuran, and a little water is added. N-Cetyl-N,N,N-trimethylammonium bromide is then added, and subsequently a solution of the homoallyl alcohol (0.8 mol) in tetrahydrofuran and finally propargyl bromide (1.32 mol) are added dropwise at room temperature. The mixture is warmed to about 45° C. and stirred at this temperature for 16 hours. The reaction mixture is then poured into ice-water and subjected to conventional work-up. The organic phase is dried and concentrated and chromatographed on silica gel. After the solvent has been distilled off, the product fraction gives the enyne. Yield: 75%. Further enynes according to the invention having a different substitution pattern are prepared correspondingly.

c)

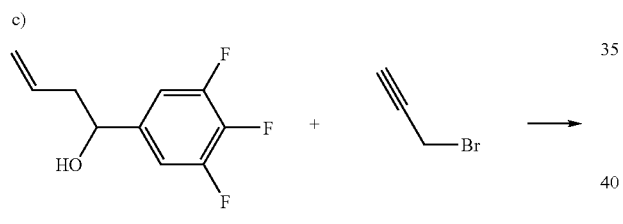

-continued

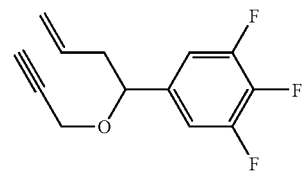

General Working Procedure B6c (GWP-B6c)

Solid sodium hydroxide (8.1 mol) is suspended in tetrahydrofuran, and a little water is added. The homoallyl alcohol (4.03 mol) and cetyltrimethylammonium bromide (0.2 mol) are subsequently added. Propargyl bromide (4.1 mol) is added dropwise at room temperature. The mixture is then warmed to about 40° C. and stirred at this temperature for 20 hours. Propargyl bromide (0.5 mol) is subsequently added dropwise again, and the mixture is stirred for a further 12 hours. The mixture is cooled and poured into ice-water. The organic phase is subjected to conventional work-up and dried and concentrated and then chromatographed on silica gel. After the solvent has been distilled off, the product fraction gives the enyne. Yield: 98%. Further enynes according to the invention having a different substitution pattern are prepared correspondingly.

Example 7

Physical Parameters of Compounds According to the Invention

Table B5 shows selected physical parameters of some compounds according to the invention which have been prepared in accordance with the procedures in the above examples. (The entries in the "Compound" column refer to the names given in Examples 1 to 6.)

TABLE B5

| Compound | $\Delta n$ | $\Delta\epsilon$ | $\gamma_1$ [mPa · s] | m.p. [° C.] | cl.p. [° C.] | Phase transitions |
|---|---|---|---|---|---|---|
| B1.2-3* | 0.0469 | 3.1 | 20 | 14 | | |
| B1.2-4* | 0.0240 | 7.7 | 23 | 28 | | C 28 I |
| B1.2-6** | 0.0850 | 11.5 | 144 | 131 | 31*** | C 131 I |
| B1.2-7* | 0.1753 | 13.7 | 211 | 95 | 48*** | C 95 I |
| B1.2-11* | 0.0870 | −3.4 | 92 | 53 | −25*** | C 53 I |
| B1.2-22* | 0.1841 | 9.9 | | 117 | 124*** | C 117 I |
| B2.2-3* | 0.1020 | 11.7 | 398 | 70 | 72 | C 70 N 72 I |
| B2.2-5* | 0.0920 | 12.9 | | 59 | 75 | C 59 N 75 I |
| B2.2-11** | 0.1785 | 26.8 | | 125 | 159 | C 125 N 159 I |
| B3.1-5** | 0.1745 | 22.6 | 312 | 116 | 128 | C 116 N 128 I |
| B4.1-4* | 0.0475 | 14.0 | 140 | 72 | 16*** | C 72 I |
| B4.1-5* | 0.1159 | 14.5 | 130 | 52 | 20*** | C 52 I |
| B4.1-6* | 0.1493 | 27.3 | 287 | 78 | 92 | C 78 N 92 I |
| B4.1-7* | 0.0440 | −2.5 | 84 | 22 | −40*** | |
| B4.1-8* | 0.1422 | 10.1 | 116 | 54 | 107*** | C 54 Sm? 87 SmB 154 SmA 168 I |
| B4.1-9* | 0.0540 | 14.1 | 124 | 45 | 26*** | |
| B4.1-12* | 0.1070 | 29.7 | 213 | 89 | 45*** | C 89 I |
| B4.1-13* | 0.1310 | 29.9 | | 89 | 57*** | |
| B4.1-14* | 0.1157 | 12.3 | | 28 | 25*** | C 28 N (11) I |
| B4.1-15* | 0.1100 | 15.2 | | 37 | 39 | C 37 SmA(35) N 39 I |
| B4.1-16* | 0.0920 | 17.8 | | 68 | −12*** | C 68 I |
| B4.2-4* | 0.1243 | 14.8 | 178 | 41 | 44*** | C 41 I |

TABLE B5-continued

| Compound | Δn | Δε | γ₁ [mPa·s] | m.p. [°C.] | cl.p. [°C.] | Phase transitions |
|---|---|---|---|---|---|---|
| B4.2-5* | 0.1256 | 18.0 | 239 | 58 | 61 | C 58 SmA (37) N 61 I |
| B4.2-6* | 0.0599 | 14.1 | 136 | 71 | 31*** | C 71 I |
| B4.2-7* | 0.0570 | 13.4 | 160 | 35 | 66 | C 35 N 66 I |
| B4.2-8* | 0.1430 | 9.6 | 189 | 50 | 99 | C 50 Sm? (32) SmA 64 N 99 I |
| B4.2-9* | 0.1380 | 12.7 | 236 | 45 | 89*** | C 45 Sm? 68 Sm? 118 I |
| B4.2-10* | 0.0688 | 9.7 | 187 | 41 | 96 | C 41 SmB 51 N 96 I |
| B4.2-11* | 0.0780 | 9.1 | 178 | −41 | 129 | C −41 SmB 123 N 129 |
| B4.2-12* | 0.0701 | 11.7 | 199 |  | 106 | SmB 74 N 106 I |
| B4.2-13* | 0.0623 | 11.5 |  |  | 106 | SmB 81 N 106 I |
| B4.2-14* | 0.0689 | 9.1 |  | −54 | 124*** | C −54 SmB 129 I |
| B4.2-15* | 0.1220 | 19.1 | 625 | 61 | 192 | C 61 N 192 I |
| B4.2-16* | 0.1328 | 13.4 | 806 | 44 | 213 | C 44 Sm? 45 N 213 |
| B4.2-17* | 0.1390 | 9.4 |  | 84 | 232 | C 84 N 232 I |
| B4.2-18* | 0.1370 | 10.7 |  | 47 | 238 | C 47 SmB 91 N 238 I |
| B4.2-19* | 0.1291 | 15.7 | 725 | 60 | 207 | C 60 SmB 81 N 207 I |
| B4.2-20* | 0.1254 | 12.7 |  | 43 | 44 | C 43 N 44 I |
| B4.2-21* | 0.0568 | 11.8 | 216 | 39 | 75 | C 39 N 75 I |
| B4.2-22* | 0.1364 | 29.7 |  | 70 | 102 | C 70 N 102 I |
| B4.2-23* | 0.1231 | 34.9 | 457 | 81 | 83 | C 81 N 83 I |
| B4.2-24* | 0.1060 | 40.0 |  | 27 |  |  |
| B4.2-25* | 0.1071 | 17.3 | 176 | 64 | 13*** | C 64 I |
| B4.2-26* | 0.1450 | 32.2 | 300 | 75 | 118 | C 75 N 118 I |
| B4.2-27* | 0.1384 | 19.7 | 718 | 74 | 198 | C 74 N 198 I |
| B4.2-28* | 0.0800 | 28.2 | 128 | 32 | −50*** | C 32 I |
| B4.2-29** | 0.1190 | 40.8 |  | 91 | 55*** | C 91 I |
| B4.2-30* | 0.1561 | 66.5 |  | 74 | 141 | C 74 SmC? (65) N 141 I |
| B4.2-31* | 0.1330 | 31.5 |  | 95 | 75*** | C 95 N (87) I |
| B4.2-32* | 0.1158 | 35.6 |  | 73 | 98 | C 73 N 98 I |
| B4.2-33* | 0.1330 | 25.3 |  | 80 | 120 | C 80 N 120 I |

*The parameters Δn, Δε and γ₁ were determined by measurement of a mixture of 10% by weight of the compound in the host ZLI-4792 (Merck KGaA, Darmstadt) followed by extrapolation.
**The parameters Δn, Δε and γ₁ were determined with 5% by weight of the compound in ZLI-4792.
***The clearing point was determined by measurement of a mixture of 10 or 5% by weight of the compound in the host ZLI-4792 followed by extrapolation.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The entire disclosures of all applications, patents and publications, cited herein and of corresponding German application No. 10324348.8, filed May 27, 2003 are incorporated by reference herein.

The preceding examples can be repeated with similar success by substituting the generically or specifically described reactants and/or operating conditions of this invention for those used in the preceding examples.

From the description, one skilled in the art can easily ascertain the essential characteristics of this invention and, without departing from the spirit and scope thereof, can make various changes and modifications of the invention to adapt it to various usages and conditions.

The invention claimed is:

1. A compound of formula I

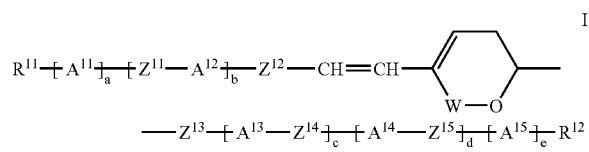

wherein a, b, c, d and e are each, independently of one another, 0 or 1;

W is —CH₂— or —C(=O)—;

$R^{11}$ is H, or an alkyl radical having 1 to 15 carbon atoms which is unsubstituted or mono- or polysubstituted, identically or differently, by halogen or —CN, in which one or more CH₂ groups are optionally replaced by —C≡C—, —CH=CH—, —O—, —S—, —C(O)—O— and/or —O—C(O)— in such a way that hetero atoms are not linked directly to one another;

$R^{12}$ is H, halogen, —CN, —NCS, aralkyl, —O-aralkyl or an alkyl radical having 1 to 15 carbon atoms which is unsubstituted or mono- or polysubstituted, identically or differently, by halogen or —CN, in which one or more CH₂ groups are optionally replaced by —C≡C—, —CH=CH—, —O—, —S—, —C(O)—O— and/or —O—C(O)— in such a way that hetero atoms are not linked directly to one another;

$Z^{11}$ is a single bond, —CH₂—, —CH₂CH₂—, —CF₂CH₂—, —CH₂CF₂—, —CF₂CF₂—, —CH=CH— or —C≡C—;

$Z^{12}$ is a single bond, —CH₂—, —CH₂CH₂—, —CF₂CH₂—, —CH₂CF₂— or —CF₂CF₂—;

$Z^{13}$, $Z^{14}$ and $Z^{15}$ are each, independently of one another, a single bond, —CH₂CH₂—, —CF₂CF₂—, —CH₂CF₂—, —CF₂CF₂—, —CH=CH—, —C≡C—, —CH₂O—, —CF₂O—, —C(O)— or —C(O)—O—;

$A^{11}$ and $A^{12}$, independently of one another, are

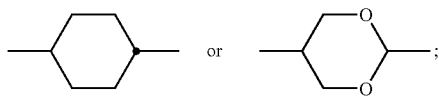

$A^{13}$ and $A^{14}$, independently of one another, are

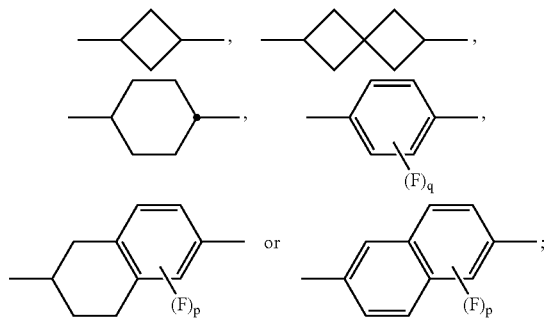

and
$A^{15}$ is

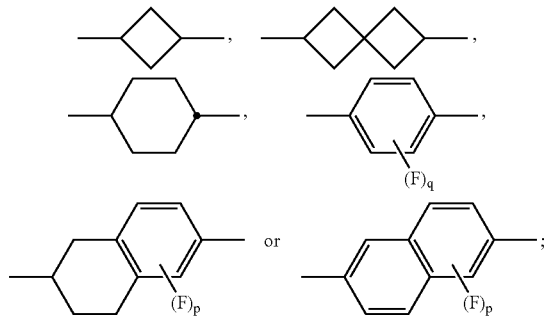

or
$A^{15}$-$R^{12}$ together are

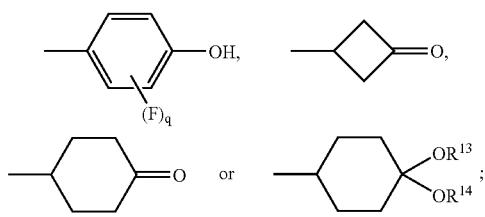

or
$Z^{13}$-[-$A^{13}$-$Z^{14}$-]$_c$-[-$A^{14}$-$Z^{15}$-]$_d$-[-$A^{15}$-]$_e$-$R^{12}$ is

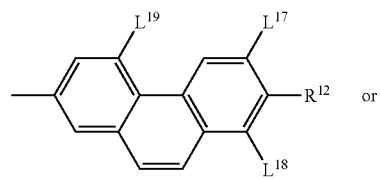

-continued

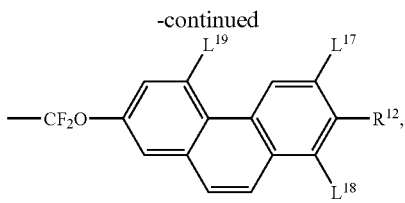

wherein $R^{12}$ is as defined above,
$L^{17}$, $L^{18}$ and $L^{19}$ independently of one another, are H or F;
q is 0, 1, 2, 3 or 4;
p is 0, 1, 2 or 3; and
$R^{13}$ and $R^{14}$ independently of one another, are an alkanyl radical having 1 to 7 carbon atoms or together are an alkylene bridge having 2 to 7 carbon atoms;
wherein in each case independently of each other, aralkyl and —O— aralkyl radicals are optionally substituted by one or more halogen, $NO_2$, alkanyl and/or alkoxy groups,
with the following provisos:
1) when $Z^{13}$ is directly linked to $R^{12}$, $R^{12}$ is H, aralkyl, alkanyl or alkenyl when $Z^{13}$ is —C(=O)—O— or —C(=O)—, and $Z^{13}$ is not —CH$_2$O— or —CF$_2$O—;
2) when $Z^{14}$ is directly linked to $R^{12}$, $R^{12}$ is H, aralkyl, alkanyl or alkenyl when $Z^{14}$ is —C(=O)—O— or —C(=O)—, and $Z^{14}$ is not —CH$_2$O— or —CF$_2$O—;
3) when $Z^{15}$ is directly linked to $R^{12}$, $R^{12}$ is H, aralkyl, alkanyl or alkenyl when $Z^{15}$ is —C(=O)—O— or —C(=O)—, and $Z^{15}$ is not —CH$_2$O— or —CF$_2$O—; and
4) when a and b are 0, and $Z^{12}$ and $Z^{13}$ are single bonds, $R^{12}$ is not H.

2. A compound according to claim 1, wherein a+b+c+d+e≦3.

3. A compound according to claim 1, wherein W is —CH$_2$—.

4. A compound according to claim 1, wherein $Z^{12}$ is a single bond.

5. A compound according to claim 4, wherein a and b are zero; and
$R^{11}$ is H.

6. A compound according to claim 1, wherein $Z^{13}$ is a single bond, —C(O)—O— or —CF$_2$O—.

7. A compound according to claim 1, wherein a is zero;
b is 1;
$Z^{11}$ is a single bond; and
$A^{12}$ is

8. A compound according to claim 1, wherein c, d and e are simultaneously zero;
$Z^{13}$ is —C(O)—O—; and
$R^{12}$ is H, aralkyl, alkanyl or alkenyl.

9. A compound according to claim 1, wherein e is 1;

$A^{15}$ is

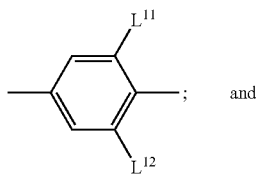
and $L^{11}$ and $L^{12}$ independently of one another, are H or F.

10. A compound according to claim 1, wherein
at least one of c and d is 1;
e is 1; and
$Z^{14}$ and $Z^{15}$ independently of one another, are a single bond or —$CF_2O$—.

11. A compound according to claim 1, wherein
e is 1;
$A^{15}$-$R^{12}$ is

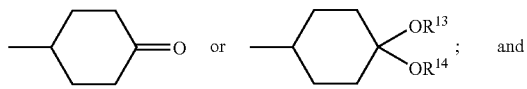

$R^{13}$ and $R^{14}$ are as defined in claim 1.

12. A process for the preparing a pyran compound of formula I according to claim 1, comprising converting in an enyne metathesis reaction in the presence of a metathesis catalyst an enyne compound of formula II to a pyran compound of formula I,

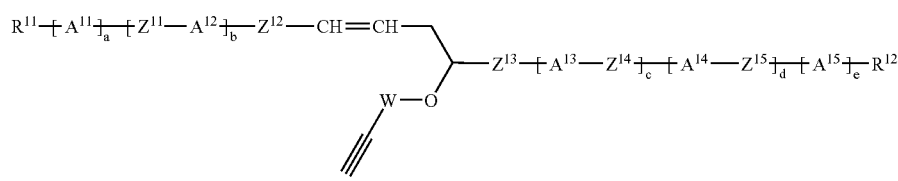

II wherein a, b, c, d, e, W, $R^{11}$, $R^{12}$, $Z^{11}$, $Z^{12}$, $Z^{13}$, $Z^{14}$, $Z^{15}$, $A^{11}$, $A^{12}$, $A^{13}$, $A^{14}$ and $A^{15}$ are as defined in claim 1,
with the following provisos:

1) when $Z^{13}$ is directly linked to $R^{12}$, $R^{12}$ is H, aralkyl or alkanyl when $Z^{13}$ is —C(=O)—, $R^{12}$ is aralkyl or alkanyl when $Z^{13}$ is —C(=O)—O—, and $Z^{13}$ is not —$CH_2O$— or —$CF_2O$—;

2) when $Z^{14}$ is directly linked to $R^{12}$, $R^{12}$ is H, aralkyl or alkanyl when $Z^{14}$ is —C(=O)—, $R^{12}$ is aralkyl or alkanyl when $Z^{14}$ is —C(=O)—O—, and $Z^{14}$ is not —$CH_2O$— or —$CF_2O$—; and 3) when $Z^{15}$ is directly linked to $R^{12}$, $R^{12}$ is H, aralkyl or alkanyl when $Z^{15}$ is —C(=O)—, $R^{12}$ is aralkyl or alkanyl when $Z^{15}$ is —C(=O)—O—, and $Z^{15}$ is not —$CH_2O$— or —$CF_2O$—.

13. A process according to claim 12, wherein the metathesis catalyst is a ruthenium-alkylidene complex.

14. A process for preparing a pyran compound of formula I according to claim 1, comprising obtaining a pyran compound of formula I in the presence of a metathesis catalyst from a cross metathesis reaction of a pyran compound of formula I-C and of an alkene compound of formula IIIa or formula IIIb

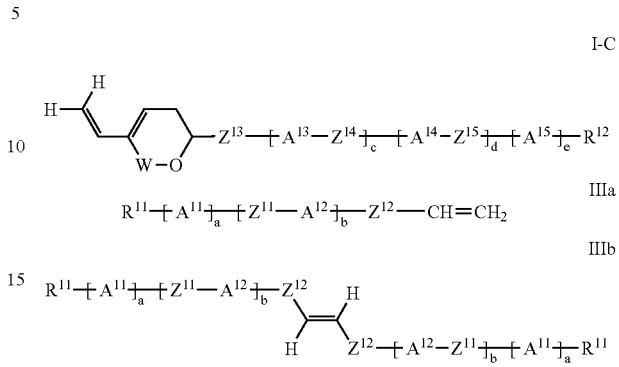

wherein a, b, c, d, e, W, $R^{11}$, $R^{12}$, $Z^{11}$, $Z^{12}$, $Z^{13}$, $Z^{14}$, $Z^{15}$, $A^{11}$, $A^{12}$, $A^{13}$, $A^{14}$ and $A^{15}$ are as defined in claim 1,
with the following provisos:

1) when $Z^{13}$ is directly linked to $R^{12}$, $R^{12}$ is H, aralkyl or alkanyl when $Z^{13}$ is —C(=O)—, $R^{12}$ is aralkyl or alkanyl when $Z^{13}$ is —C(=O)—O—, and $Z^{13}$ is not —$CH_2O$— or —$CF_2O$—;

2) when $Z^{14}$ is directly linked to $R^{12}$, $R^{12}$ is H, aralkyl or alkanyl when $Z^{14}$ is —C(=O)—, $R^{12}$ is aralkyl or alkanyl when $Z^{14}$ is —C(=O)—O—, and $Z^{14}$ is not —$CH_2O$— or —$CF_2O$—; and 3) when $Z^{15}$ is directly linked to $R^{12}$, $R^{12}$ is H, aralkyl or alkanyl when $Z^{15}$ is —C(=O)—, $R^{12}$ is aralkyl or alkanyl when $Z^{15}$ is —C(=O)—O—, and $Z^{15}$ is not —$CH_2O$— or —$CF_2O$—.

15. A process according to claim 14, wherein the metathesis catalyst is a ruthenium-alkylidene complex.

16. A process according to claim 13, wherein a compound of formula I-C is prepared, and said process further comprises obtaining a pyran compound of formula I in the presence of a metathesis catalyst from a cross metathesis reaction of a pyran compound of formula I-C and of an alkene compound of formula IIIa or formula IIIb

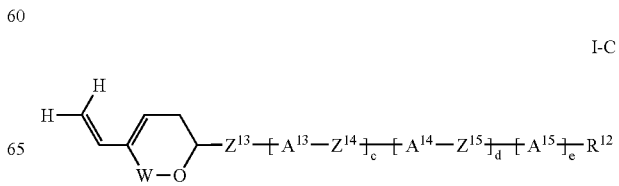

-continued

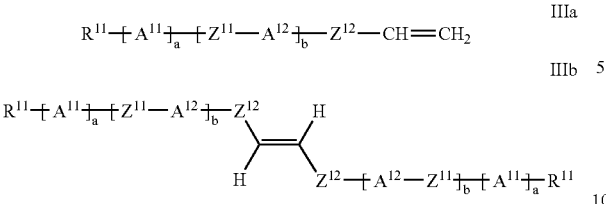

IIIa

IIIb wherein
a,b,c,d and e are each, independently of one another, 0 or 1;

W is —CH$_2$- or —C(=O)-;

$R^{11}$ is H, an alkyl radical having 1 to 15 carbon atoms which is unsubstituted or mono- or polysubstituted, identically or differently, by halogen or —CN, in which one or more CH$_2$ groups are optionally replaced by —C≡C—, —CH=CH—, —O—, —S—, —C(O)—O- and/or —O-C(O) in such a way that hetero atoms are not linked directly to one another;

$R^{12}$ is H, halogen, —CN, —NCS, aralkyl, —O-aralkyl or an alkyl radical having 1 to 15 carbon atoms which is unsubstituted or mono- or polysubstituted, identically or differently, by halogen or -CN, in which one or more CH$_2$ groups are optionally replaced by —C≡C—, —CH=CH—, —O—, —S—, —C(O)—O— and/or —O—C(O)— in such a way that hetero atoms are not linked directly to one another;

$Z^{11}$ is a single bond, —Ch$_2$—, —CH$_2$CH$_2$—, —CF$_2$CH$_2$—, —CH$_2$CF$_2$—, —CF$_2$CF$_2$—, —CH=CH— or —C≡C—;

$Z^{12}$ is a single bond, —Ch$_2$—, —CH$_2$CH$_2$—, —CF$_2$CH$_2$—, —CH$_2$CF$_2$—, or —CF$_2$CF$_2$—;

$Z^{13}$, $Z^{14}$ and $Z^{15}$ are each, independently of one another, a single bond, —CH$_2$CH$_2$—, —CF$_2$CH$_2$—, —CH$_2$CF$_2$—, —CF$_2$CF$_2$—, —CH=CH—, C≡C—, —CH$_2$O—, —CF$_2$O—, —C(O)— or —C(O)—O—;

$A^{11}$ and $A^{12}$, independently of one another, are

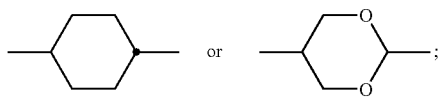

$A^{13}$ and $A^{14}$, independently of one another, are

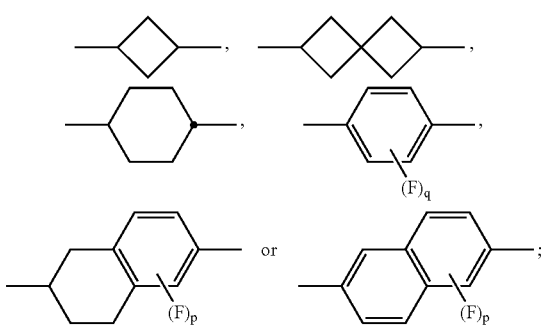

and $A^{15}$ is

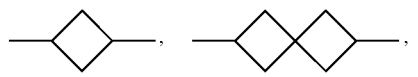

or
$A^{15}$-$R^{12}$ together are

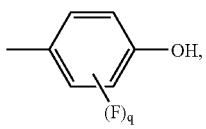

or
$Z^{13}$-[-$A^{13}$-$Z^{14}$-]$_c$-[-$A^{14}$-$Z^{15}$-]$_d$-[-$A^{15}$-]$_e$-$R^{12}$ is

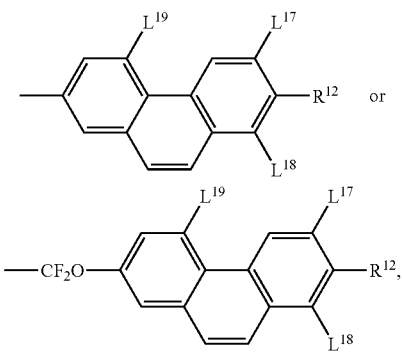

wherein $R^{12}$ is as defined above,
$L^{17}$, $L^{18}$ and $L^{19}$ independently of one another, are H or F;
q is 0,1,2,3 or 4;
is 0,1,2 or 3; and
$R^{13}$ and $R^{14}$ independently of one another, are an alkanyl radical having 1 to 7 carbon atoms or together are an alkylene bridge having 2 to 7 carbon atoms;
wherein in each case independently of each other, aralkyl and —O—aralkyl radicals are optionally substituted by one or more halogen, NO$_2$, alkanyl and/or alkoxy groups,
with the following provisos:
1) when $Z^{13}$ is directly linked to $R^{12}$, $R^{12}$ is H, aralkyl, alkanyl or alkenyl when $Z^{13}$ is —C(=O)—O— or —C(=O)—, and $Z^{13}$ is not —CH$_2$O— or —CF$_2$O—;
2) when $Z^{14}$ is directly linked to $R^{12}$, $R^{12}$ is H, aralkyl, alkanyl or alkenyl when $Z^{14}$ is —C(=O)—O— or —C(=O)—, and $Z^{14}$ is not —CH$_2$O— or —CF$_2$O—;

3) when $Z^{15}$ is directly linked to $R^{12}$, $R^{12}$ is H, aralkyl, alkanyl or alkenyl when $Z^{15}$ is —C(=O)—O— or —C(=O)—, and $Z^{15}$ is not —CH$_2$O— or —CF$_2$O—; and
4) when a and b are 0, and $Z^{12}$ and $Z^{13}$ are single bonds, $R^{12}$ is not H.

17. A process according to claim 12, further comprising after the metathesis reaction, when in the compound of formula I, W is —C(=O)— and $Z^{13}$, $Z^{14}$ and $Z^{15}$ are not —C(O)—, a reduction reaction for conversion of said compound of formula I into a pyran compound of formula I in which
W is —CH$_2$—;
$R^{11}$ is H, an alkyl radical having 1 to 15 carbon atoms which is unsubstituted or mono- or polysubstituted, identically or differently, by halogen or —CN, in which one or more CH$_2$ groups are optionally replaced by —C≡C—, —CH=CH—, —O— and/or —S— in such a way that hetero atoms are not linked directly to one another;
$R^{12}$ is H, halogen, —CN, —NCS, aralkyl, —O-aralkyl or an alkyl radical having 1 to 15 carbon atoms which is unsubstituted or mono- or polysubstituted, identically or differently, by halogen or —CN, in which one or more CH$_2$ groups are optionally replaced by —C≡C—, —CH=CH—, —O— and/or —S— in such a way that hetero atoms are not linked directly to one another; and
$Z^{13}$, $Z^{14}$ and $Z^{15}$ are each, independently of one another, a single bond, —CH$_2$CH$_2$—, —CF$_2$CH$_2$—, —CH$_2$CF$_2$—, —CF$_2$CF$_2$—, —CH=CH—, —C≡C—, —CH$_2$O— or —CF$_2$O—.

18. A process according to claim 17, further comprising after the reduction reaction, a catalytic hydrogenation of the compound of formula I to give a pyran compound of IV:

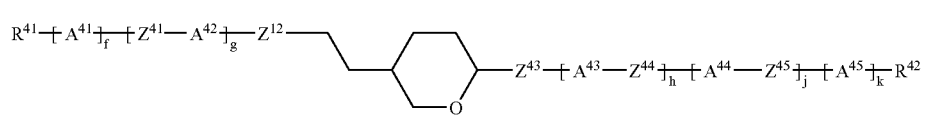

IV wherein
f, g, h, j and k are each, independently of one another, 0 or 1;
$R^{41}$ is H, or a saturated alkyl radical having 1 to 15 carbon atoms which is unsubstituted or mono- or polysubstituted, identically or differently, by halogen or —CN, in which one or more CH$_2$ groups are optionally replaced by —O—, —S—, —C(O)—O— and/or —O—C(O)— in such a way that hetero atoms are not linked directly to one another;
$R^{42}$ is H, halogen, —CN, —NCS, aralkyl, —O-aralkyl or a saturated alkyl radical having 1 to 15 carbon atoms which is unsubstituted or mono- or polysubstituted, identically or differently, by halogen or —CN, in which one or more CH$_2$ groups are optionally replaced by —O—, —S—, —C(O)—O— and/or —O—C(O)— in such a way that hetero atoms are not linked directly to one another;
$Z^{41}$ and $Z^{42}$ independently of one another, are a single bond, —CH$_2$—, —CH$_2$CH$_2$—, —CF$_2$CH$_2$—, —CH$_2$CF$_2$— or —CF$_2$CF$_2$—;
$Z^{43}$, $Z^{44}$ and $Z^{45}$ are each, independently of one another, a single bond, —CH$_2$CH$_2$—, —CF$_2$CH$_2$—, —CH$_2$CF$_2$—, —CF$_2$CF$_2$—, —CH$_2$O—, —CF$_2$O—, —C(O)— or —C(O)—O—;

$A^{41}$ and $A^{42}$ independently of one another, are

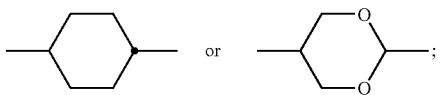

$A^{43}$ and $A^{44}$ independently of one another, are

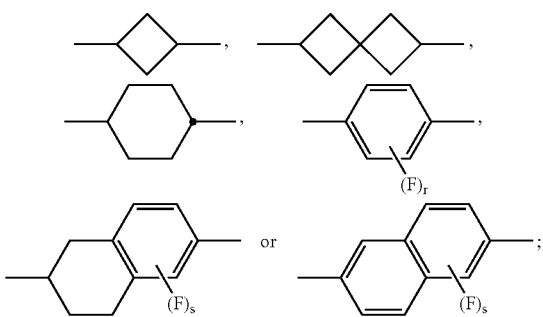

and
$A^{45}$ is

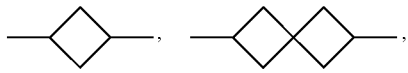

-continued

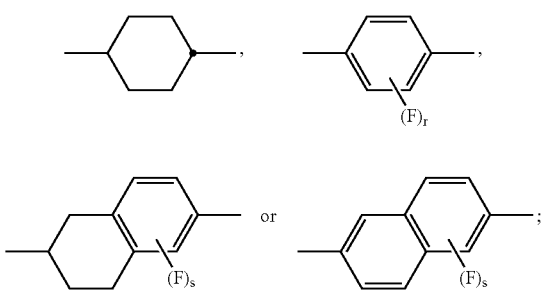

or
$A^{45}R^{42}$ together are

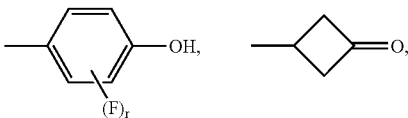

-continued

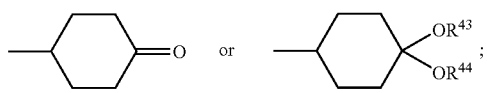

or
$Z^{43}\text{-}[\text{-}A^{43}\text{-}Z^{44}\text{-}]_r\text{-}[\text{-}A^{44}\text{-}Z^{45}\text{-}]_j\text{-}[\text{-}A^{45}\text{-}]_k\text{-}R^{42}$ is

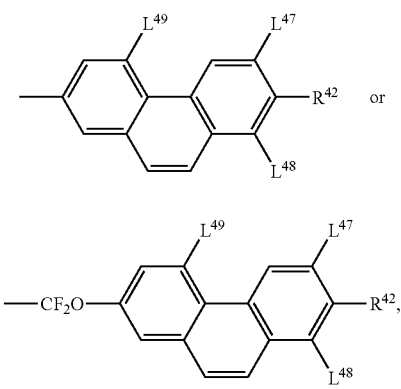

wherein $R^{42}$ is as defined above $L^{47}$, $L^{48}$ and $L^{49}$ independently of one another, are H or F;
r is 0, 1, 2, 3 or 4;
s is 0, 1, 2 or 3; and
$R^{43}$ and $R^{44}$ independently of one another, are an alkanyl radical having 1 to 7 carbon atoms or together are an alkylene bridge having 2 to 7 carbon atoms;
wherein in each case independently of each other, aralkyl and —O— aralkyl radicals are optionally substituted by one or more halogen, $NO_2$, alkanyl and/or alkoxy groups,
with the following provisos:
1) when $Z^{43}$ is directly linked to $R^{42}$, $R^{42}$ is H, aralkyl or alkanyl when $Z^{43}$ is —C(=O)—, $R^{42}$ is aralkyl or alkanyl when $Z^{43}$ is —C(=O)—O—, and $Z^{43}$ is not —CH$_2$O— or —CF$_2$O—;
2) when $Z^{44}$ is directly linked to $R^{42}$, $R^{42}$ is H, aralkyl or alkanyl when $Z^{44}$ is —C(=O)—, $R^{42}$ is aralkyl or alkanyl when $Z^{44}$ is —C(=O)—O—, and $Z^{44}$ is not —CH$_2$O— or —CF$_2$O—; and
3) when $Z^{45}$ is directly linked to $R^{42}$, $R^{42}$ is H, aralkyl or alkanyl when $Z^{45}$ is —C(=O)—, $R^{42}$ is aralkyl or alkanyl when $Z^{45}$ is —C(=O)—O—, and $Z^{45}$ is not —CH$_2$O— or —CF$_2$O—.

19. A process according to claim 14, further comprising after the metathesis reaction, when in the compound of formula I, W is —C(=O)— and $Z^{13}$, $Z^{14}$ and $Z^{15}$ are not —C(O)—, a reduction reaction for conversion of said compound of formula I into a pyran compound of formula I in which
W is —CH$_2$—;
$R^{11}$ is H, an alkyl radical having 1 to 15 carbon atoms which is unsubstituted or mono- or polysubstituted, identically or differently, by halogen or —CN, in which one or more CH$_2$ groups are optionally replaced by —C≡C—, —CH=CH—, —O— and/or —S— in such a way that hetero atoms are not linked directly to one another;
$R^{12}$ is H, halogen, —CN, —NCS, aralkyl, —O-aralkyl or an alkyl radical having 1 to 15 carbon atoms which is unsubstituted or mono- or polysubstituted, identically or differently, by halogen or —CN, in which one or more CH$_2$ groups are optionally replaced by —C≡C—, —CH=CH—, —O— and/or —S— in such a way that hetero atoms are not linked directly to one another; and
$Z^{13}$, $Z^{14}$ and $Z^{15}$ are each, independently of one another, a single bond, —CH$_2$CH$_2$—, —CF$_2$CH$_2$—, —CH$_2$CF$_2$—, —CF$_2$CF$_2$—, —CH=CH—, —C≡C—, —CH$_2$O— or —CF$_2$O—.

20. A process according to claim 19, further comprising after the reduction reaction, a catalytic hydrogenation of the compound of formula I to give a pyran compound of IV:

IV

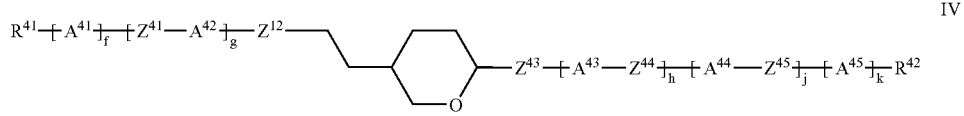

wherein
f, g, h, j and k are each, independently of one another, 0 or 1;
$R^{41}$ is H, or a saturated alkyl radical having 1 to 15 carbon atoms which is unsubstituted or mono- or polysubstituted, identically or differently, by halogen or —CN, in which one or more CH$_2$ groups are optionally replaced by —O—, —S—, —C(O)—O— and/or —O—C(O)— in such a way that hetero atoms are not linked directly to one another;
$R^{42}$ is H, halogen, —CN, —NCS, aralkyl, —O-aralkyl or a saturated alkyl radical having 1 to 15 carbon atoms which is unsubstituted or mono- or polysubstituted, identically or differently, by halogen or —CN, in which one or more CH$_2$ groups are optionally replaced by —O—, —S—, —C(O)—O— and/or —O—C(O)— in such a way that hetero atoms are not linked directly to one another;
$Z^{41}$ and $Z^{42}$ independently of one another, are a single bond, —CH$_2$—, —CH$_2$CH$_2$—, —CF$_2$CH$_2$—, —CH$_2$CF$_2$— or —CF$_2$CF$_2$—;
$Z^{43}$, $Z^{44}$ and $Z^{45}$ are each, independently of one another, a single bond, —CH$_2$CH$_2$—, —CF$_2$CH$_2$—, —CH$_2$CF$_2$—, —CF$_2$CF$_2$—, —CH$_2$O—, —CF$_2$O—, —C(O)— or —C(O)—O—;

$A^{41}$ and $A^{42}$ independently of one another, are

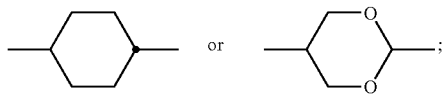

$A^{43}$ and $A^{44}$ independently of one another, are

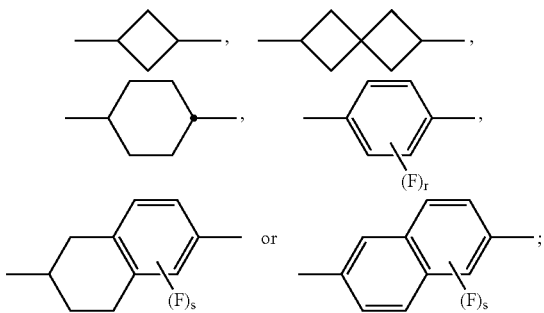

and
$A^{45}$ is

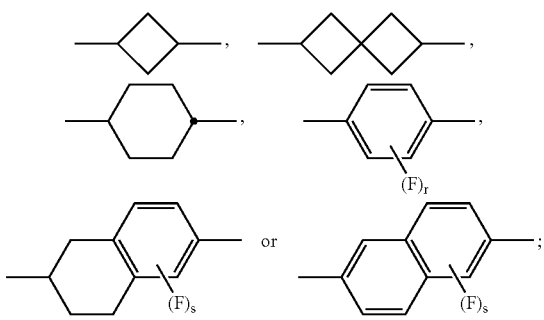

or
$A^{45}$-$R^{42}$ together are

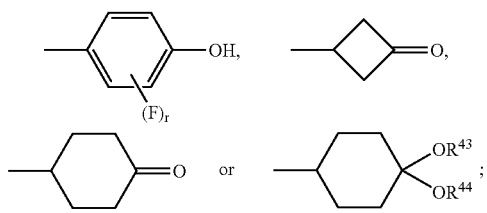

or
$Z^{43}$-[-$A^{43}$-$Z^{44}$-]$_h$-[-$A^{44}$-$Z^{45}$-]$_j$-[-$A^{45}$-]$_k$-$R^{42}$ is

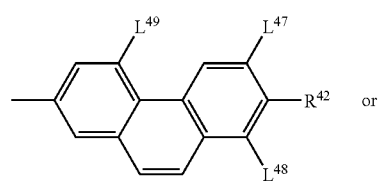

-continued

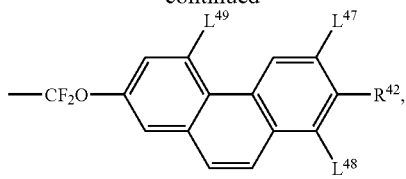

wherein $R^{42}$ is as defined above $L^{47}$, $L^{48}$ and $L^{49}$ independently of one another, are H or F;

r is 0, 1, 2, 3 or 4;

s is 0, 1, 2 or 3; and $R^{43}$ and $R^{44}$ independently of one another, are an alkanyl radical having 1 to 7 carbon atoms or together are an alkylene bridge having 2 to 7 carbon atoms;

wherein in each case independently of each other, aralkyl and —O— aralkyl radicals are optionally substituted by one or more halogen, $NO_2$, alkanyl and/or alkoxy groups, with the following provisos:

1) when $Z^{43}$ is directly linked to $R^{42}$, $R^{42}$ is H, aralkyl or alkanyl when $Z^{43}$ is —C(=O)—, $R^{42}$ is aralkyl or alkanyl when $Z^{43}$ is —C(=O)—O—, and $Z^{43}$ is not —$CH_2$O— or —$CF_2$O—;

2) when $Z^{44}$ is directly linked to $R^{42}$, $R^{42}$ is H, aralkyl or alkanyl when $Z^{44}$ is —C(=O)—, $R^{42}$ is aralkyl or alkanyl when $Z^{44}$ is —C(=O)—O—, and $Z^{44}$ is not —$CH_2$O— or —$CF_2$O—; and 3) when $Z^{45}$ is directly linked to $R^{42}$, $R^{42}$ is H, aralkyl or alkanyl when $Z^{45}$ is —C(=O)—, $R^{42}$ is aralkyl or alkanyl when $Z^{45}$ is —C(=O)—O—, and $Z^{45}$ is not —$CH_2$O— or —$CF_2$O—.

21. A process according to claim 16, further comprising after the metathesis reaction, when in the compound of formula I, W is —C(=O)— and $Z^{13}$, $Z^{14}$ and $Z^{15}$ are not —C(O)—, a reduction reaction for conversion of said compound of formula I into a pyran compound of formula I in which W is —$CH_2$—;

$R^{11}$ is H, an alkyl radical having 1 to 15 carbon atoms which is unsubstituted or mono- or polysubstituted, identically or differently, by halogen or —CN, in which one or more $CH_2$ groups are optionally replaced by —C≡C—, —CH=CH—, —O— and/or —S— in such a way that hetero atoms are not linked directly to one another;

$R^{12}$ is H, halogen, —CN, —NCS, aralkyl, —O-aralkyl or an alkyl radical having 1 to 15 carbon atoms which is unsubstituted or mono- or polysubstituted, identically or differently, by halogen or —CN, in which one or more $CH_2$ groups are optionally replaced by —C≡C—, —CH=CH—, —O— and/or —S— in such a way that hetero atoms are not linked directly to one another; and $Z^{13}$, $Z^{14}$ and $Z^{15}$ are each, independently of one another, a single bond, —$CH_2CH_2$—, —$CF_2CH_2$—, —$CH_2CF_2$—, —$CF_2CF_2$—, —CH=CH—, —C≡C—, —$CH_2$O— or —$CF_2$O—.

22. A process according to claim 21, further comprising after the reduction reaction, a catalytic hydrogenation of the compound of formula I to give a pyran compound of IV:

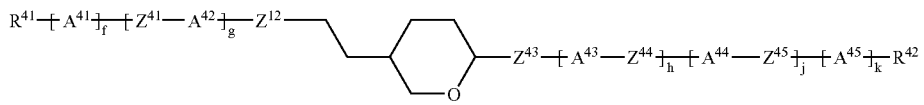

IV wherein
f, g, h, j and k are each, independently of one another, 0 or 1;
$R^{41}$ is H, or a saturated alkyl radical having 1 to 15 carbon atoms which is unsubstituted or mono- or polysubstituted, identically or differently, by halogen or —CN, in which one or more $CH_2$ groups are optionally replaced by —O—, —S—, —C(O)—O— and/or —O—C(O)— in such a way that hetero atoms are not linked directly to one another;
$R^{42}$ is H, halogen, —CN, —NCS, aralkyl, —O-aralkyl or a saturated alkyl radical having 1 to 15 carbon atoms which is unsubstituted or mono- or polysubstituted, identically or differently, by halogen or —CN, in which one or more $CH_2$ groups are optionally replaced by —O—, —S—, —C(O)—O— and/or —O—C(O)— in such a way that hetero atoms are not linked directly to one another;
$Z^{41}$ and $Z^{42}$ independently of one another, are a single bond, —$CH_2$—, —$CH_2CH_2$—, —$CF_2CH_2$—, —$CH_2CF_2$— or —$CF_2CF_2$—;
$Z^{43}$, $Z^{44}$ and $Z^{45}$ are each, independently of one another, a single bond, —$CH_2CH_2$—, —$CF_2CH_2$—, —$CH_2CF_2$—, —$CF_2CF_2$—, —$CH_2O$—, —$CF_2O$—, —C(O)— or —C(O)—O—;
$A^{41}$ and $A^{42}$ independently of one another, are

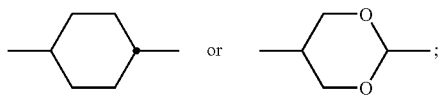

$A^{43}$ and $A^{44}$ independently of one another, are

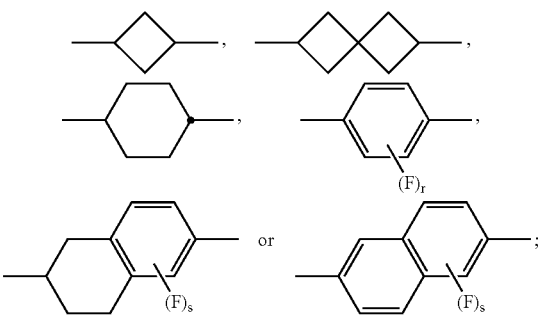

and
$A^{45}$ is

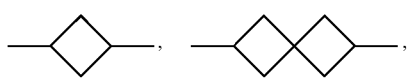

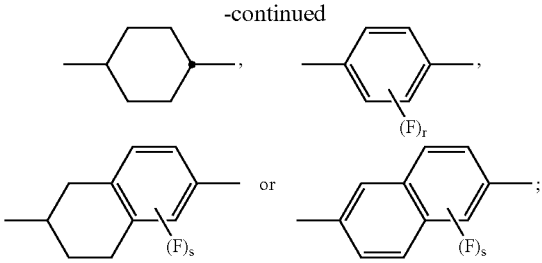

or
$A^{45}$-$R^{42}$ together are

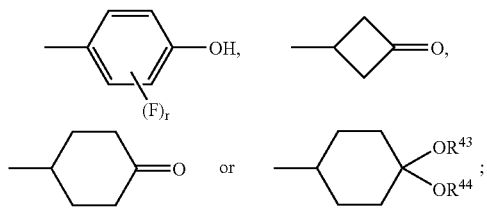

or
$Z^{43}$-[-$A^{43}$-$Z^{44}$-]$_h$-[-$A^{44}$-$Z^{45}$-]$_j$-[-$A^{45}$-]$_k$-$R^{42}$ is

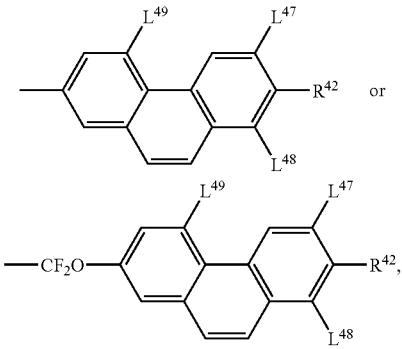

wherein $R^{42}$ is as defined above
$L^{47}$, $L^{48}$ and $L^{49}$ independently of one another, are H or F;
r is 0, 1, 2, 3 or 4;
s is 0, 1, 2 or 3; and
$R^{43}$ and $R^{44}$ independently of one another, are an alkanyl radical having 1 to 7 carbon atoms or together are an alkylene bridge having 2 to 7 carbon atoms;
wherein in each case independently of each other, aralkyl and —O— aralkyl radicals are optionally substituted by one or more halogen, $NO_2$, alkanyl and/or alkoxy groups, with the following provisos:

1) when $Z^{43}$ is directly linked to $R^{42}$, $R^{42}$ is H, aralkyl or alkanyl when $Z^{43}$ is —C(=O)—, $R^{42}$ is aralkyl or alkanyl when $Z^{43}$ is —C(=O)—O—, and $Z^{43}$ is not —CH$_2$O— or —CF$_2$O—;

2) when $Z^{44}$ is directly linked to $R^{42}$, $R^{42}$ is H, aralkyl or alkanyl when $Z^{44}$ is —C(=O)—, $R^{42}$ is aralkyl or alkanyl when $Z^{44}$ is —C(=O)—O—, and $Z^{44}$ is not —CH$_2$O— or —CF$_2$O—; and 3) when $Z^{45}$ is directly linked to $R^{42}$, $R^{42}$ is H, aralkyl or alkanyl when $Z^{45}$ is —C(=O)—, $R^{42}$ is aralkyl or alkanyl when $Z^{45}$ is —C(=O)—O—, and $Z^{45}$ is not —CH$_2$O— or —CF$_2$O—.

23. A compound according to claim 1, which is of one of the following formulae

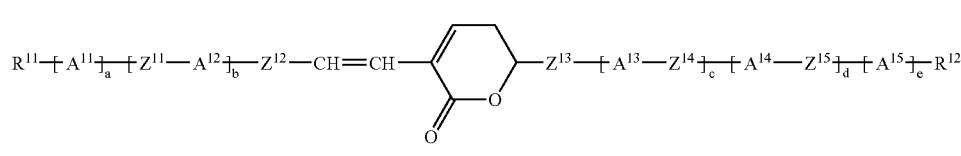

I-A

I-B

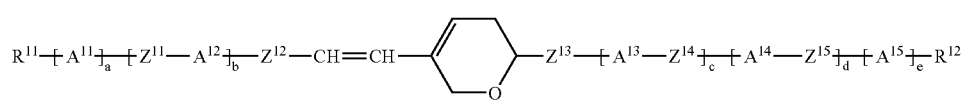

I-C

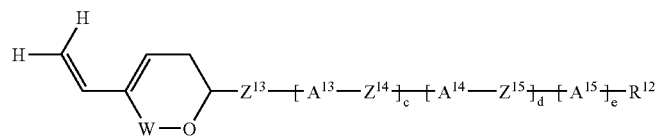

I-D

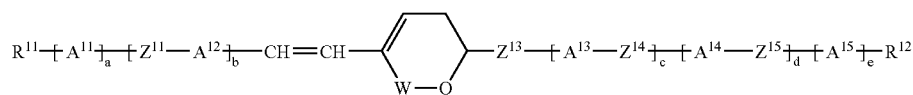

I-E

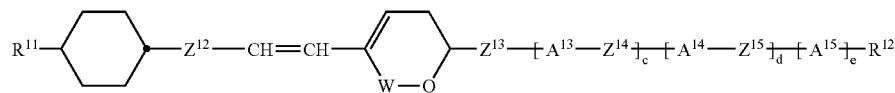

I-F

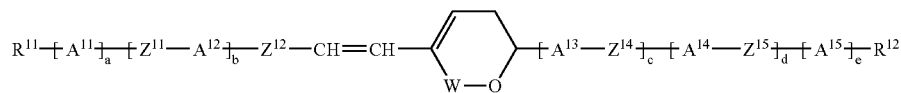

I-G

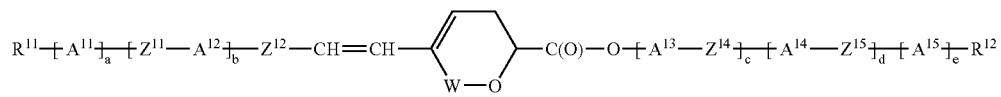

I-H

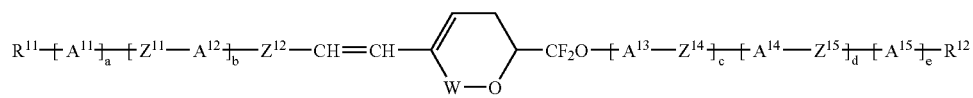

I-J

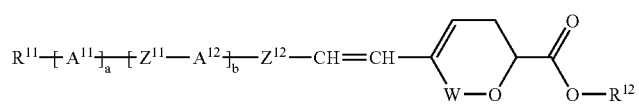

I-K

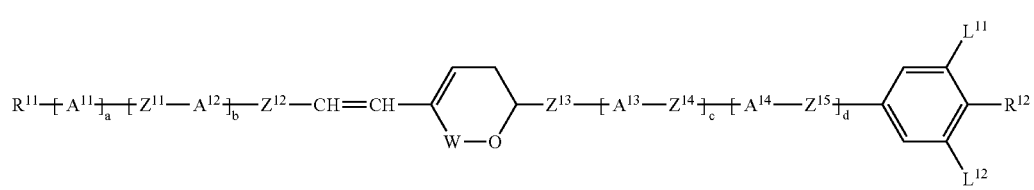

I-L

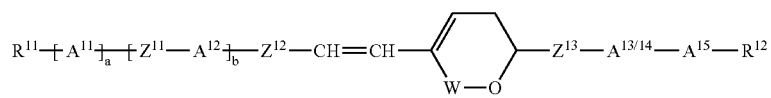

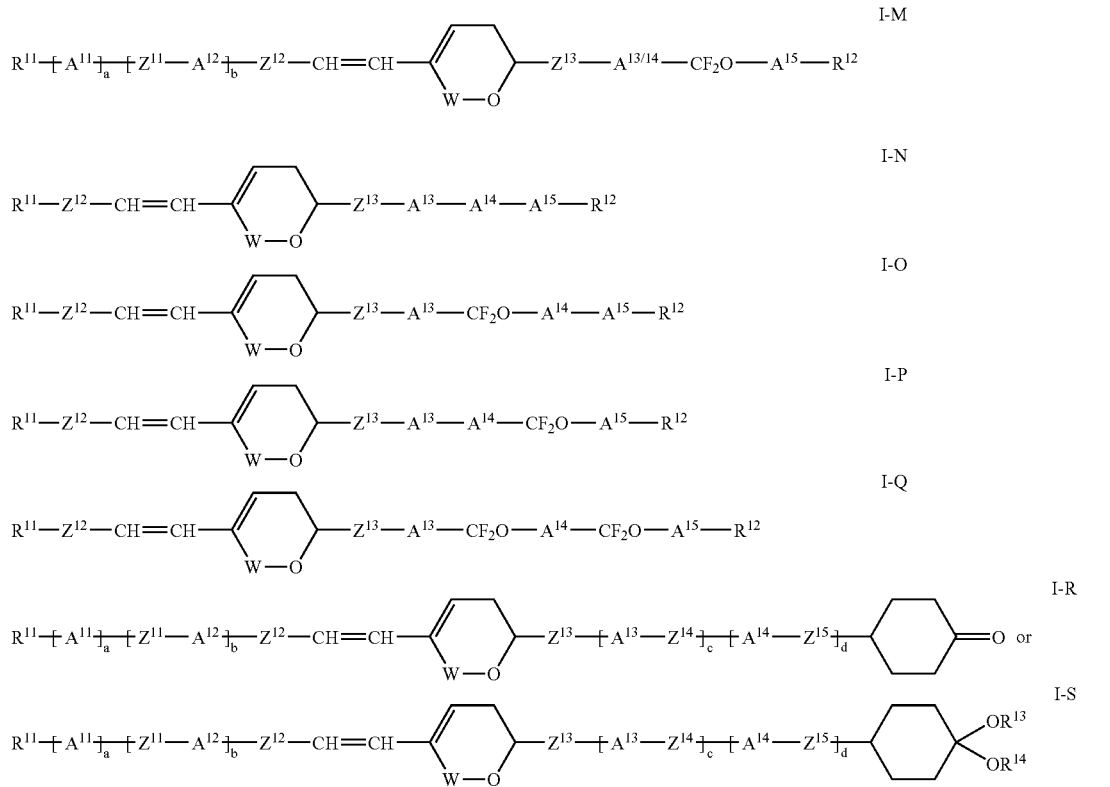

wherein a, b, c, d, e, W, $R^{11}$, $R^{12}$, $R^{13}$, $R^{14}$, $Z^{11}$, $Z^{12}$, $Z^{13}$, $Z^{14}$, $Z^{15}$, $A^{11}$, $A^{12}$, $A^{13}$, $A^{14}$ and $A^{15}$ are as defined in claim 1, and $L^{11}$ and $L^{12}$ are each, independently of one another, H or F.

24. A compound according to claim 1, wherein $R^{12}$ is —CN, halogen or a straight-chain alkanyl or alkoxy having from 1 to 5 carbon atoms which is optionally mono- or polysubstituted by halogen.

25. A compound according to claim 24, wherein $R^{12}$ is —CN, halogen or a straight-chain alkanyl or alkoxy having from 2 to 5 carbon atoms which is optionally mono- or polysubstituted by halogen.

26. A compound according to claim 1, wherein $R^{12}$ is halogen or an unbranched alkanyl or alkoxy radical having from 1 to 5 carbon atoms which is optionally mono- or polysubstituted by halogen.

27. A compound of formula I

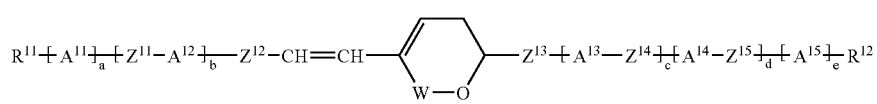

wherein
a, b, c, d and e are each, independently of one another, 0 or 1;
W is —$CH_2$— or —C(=O)—;
$R^{11}$ is H, or an alkyl radical having 1 to 15 carbon atoms which is unsubstituted or mono- or polysubstituted, identically or differently, by halogen or —CN, in which one or more $CH_2$ groups are optionally replaced by —C≡C—, —CH=CH—, —O—, —S—, —C(O)—O— and/or —O—C(O)— in such a way that hetero atoms are not linked directly to one another;
$R^{12}$ is halogen, —CN, —NCS, aralkyl, —O—aralkyl or an radical 1 to 15 carbon atoms which is unsubstituted or mono- or polysubstituted, identically or differently, by halogen or —CN, in which one or more $CH_2$ groups are optionally replaced by —C≡C—, —CH=CH—, —O—, —S—, —C(O)—O— and/or —O—C(O)— in such a way that hetero atoms are not linked directly to one another;
$Z^{11}$ is a single bond, —$CH_2$—, —$CH_2CH_2$—, —$CF_2CH_2$—, —$CH_2CF_2$—, —$CF_2CF_2$—, —CH=CH— or —C≡C—;
$Z^{12}$ is a single bond, —$CH_2$—, —$CH_2CH_2$—, —$CF_2CH_2$—, —$CH_2CF_2$— or —$CF_2CF_2$—;
$Z^{13}$, $Z^{14}$ and $Z^{15}$ each, independently of another, single bond, —$CH_2CH_2$—, —$CF_2CH_2$—, —$CH_2CF_2$—, —$CF_2CF_2$—, —CH=CH—, —C≡C—, —$CH_2O$—, —$CF_2O$—, —C(O)— or —C(O)—O—;

$A^{11}$ and $A^{12}$, independently of one another, are

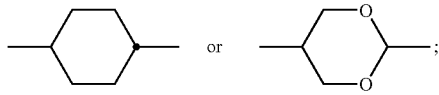

$A^{13}$ and $A^{14}$, independently of one another, are

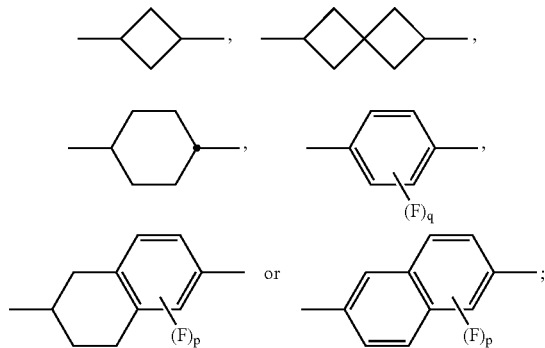

and
$A^{15}$ is

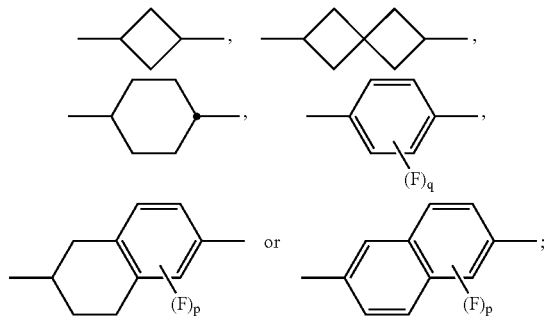

or
$A^{15}\text{-}R^{12}$ together are

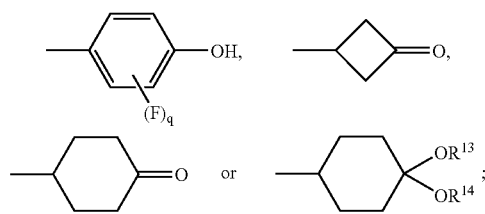

or
$Z^{13}\text{-}[\text{-}A^{13}\text{-}Z^{14}\text{-}]_c\text{-}[\text{-}A^{14}\text{-}Z^{15}\text{-}]_d\text{-}[\text{-}A^{15}\text{-}]_e\text{-}R^{12}$ is

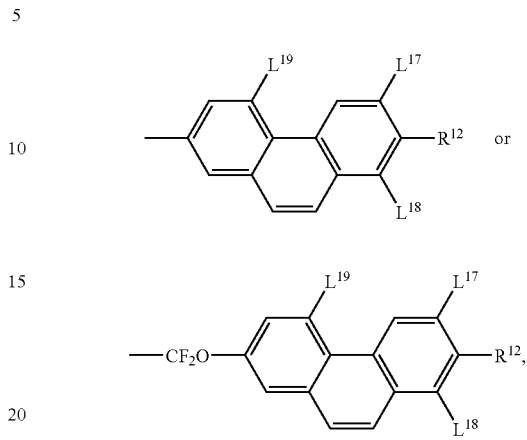

wherein $R^{12}$ is as defined above,
$L^{17}$, $L^{18}$ and $L^{19}$ independently of one another, are H or F;
q is 0, 1, 2, 3 or 4;
p is 0, 1, 2 or 3; and
$R^{13}$ and $R^{14}$ independently of one another, are an alkanyl radical having 1 to 7 carbon atoms or together are an alkylene bridge having 2 to 7 carbon atoms
wherein in each case independently of each other, aralkyl and —O—aralkyl radicals are optionally substituted by one or more halogen, $NO_2$, alkanyl and/or alkoxy groups,
with the following provisos:
1) when $Z^{13}$ is directly liked to $R^{12}$, $R^{12}$ is H, aralkyl, alkanyl or alkenyl when $Z^{13}$ is —C(=O)—O— or —C(=O)—, and $Z^{13}$ is not —CH$_2$O— or —CF$_2$O—;
2) when $Z^{14}$ is directly linked to $R^{12}$, $R^{12}$ is H, aralkyl, alkanyl or alkenyl when $Z^{14}$ is —C(=O)—O— or —C(=O)—, and $Z^{14}$ is not —CH$_2$O— or —CF$_2$O—; and
3) when $Z^{15}$ is directly linked to $R^{12}$, $R^{12}$ is H, aralkyl, alkanyl or alkenyl when $Z^{15}$ is —C(=O)—O— or —C(=O)—, and $Z^{15}$ is not —CH$_2$O— or —CF$_2$O—.

28. A compound according to claim 27, wherein $R^{12}$ is halogen, —CN, —NCS, aralkyl, —O—aralkyl or an alkyl radical having 2 to 15 carbon atoms which is unsubstituted or mono- or polysubstituted, identically or differently, by halogen or —CN, in which one or more $CH_2$ groups are optionally replaced by —C≡C—, —CH=CH—, —O—, —S—, —C(O)—O— and/or —O—C(O)— in such a way that hetero atoms are not linked directly to one another.

29. A compound of formula I

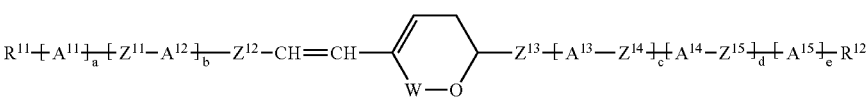

wherein a, b, c, d and e are each, independently of one another, 0 or 1;

W is —CH$_2$— or —C(=O)—;

R$^{11}$ is H, or an alkyl radical having 1 to 15 carbon atoms which is unsubstituted or mono- or polysubstituted, identically or differently, by halogen or —CN, in which one or more CH$_2$ groups are optionally replaced by —C≡C—, —CH=CH—, —O—, —S—, —C(O)—O— and/or —O—C(O)— in such a way that hetero atoms are not linked directly to one another;

R$^{12}$ is H, halogen, —CN, —NCS, aralkyl, —O-aralkyl or an alkyl radical having 1 to 15 carbon atoms which is unsubstituted or mono- or polysubstituted, identically or differently, by halogen or —CN, in which one or more CH$_2$ groups are optionally replaced by —C≡C—, —CH=CH—, —O—, —S—, —C(O)—O— and/or —O—C(O)— in such a way that hetero atoms are not linked directly to one another;

Z$^{11}$ is a single bond, —CH$_2$—, —CH$_2$CH$_2$—, —CF$_2$CH$_2$—, —CH$_2$CF$_2$—, —CF$_2$CF$_2$—, —CH=CH— or —C≡C—;

Z$^{12}$ is —CH$_2$—, —CH$_2$CH$_2$—, —CF$_2$CH$_2$—, —CH$_2$CF$_2$— or —CF$_2$CF$_2$—;

Z$^{13}$, Z$^{14}$ and Z$^{15}$ are each, independently of one another, a single bond, —CH$_2$CH$_2$—, —CF$_2$CH$_2$—, —CH$_2$CF$_2$—, —CF$_2$CF$_2$—, —CH=CH—, —C≡C—, —CH$_2$O—, —CF$_2$O—, —C(O)— or —C(O)—O—;

A$^{11}$ and A$^{12}$, independently of one another, are

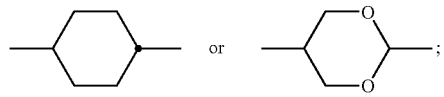

A$^{13}$ and A$^{14}$, independently of one another, are

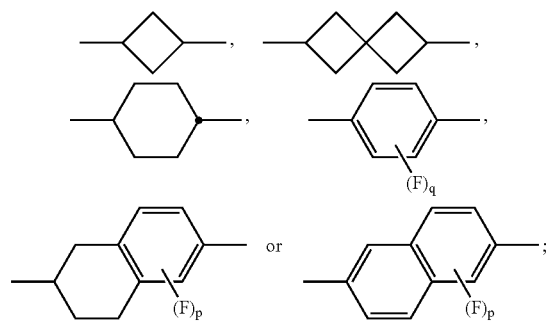

and
A$^{15}$ is

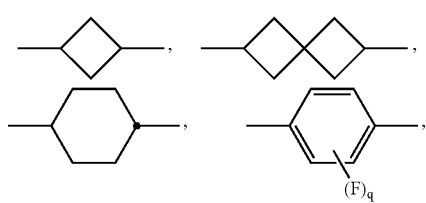

or
A$^{15}$-R$^{12}$ together are

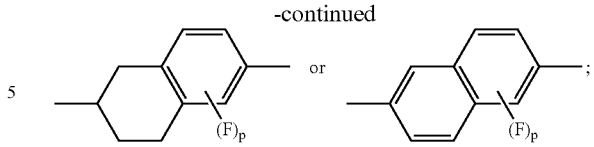

or
Z$^{13}$-[-A$^{13}$-Z$^{14}$-]$_c$-[-A$^{14}$-Z$^{15}$-]$_d$-[-A$^{15}$-]$_e$-R$^{12}$ is

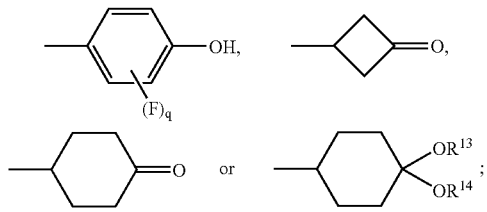

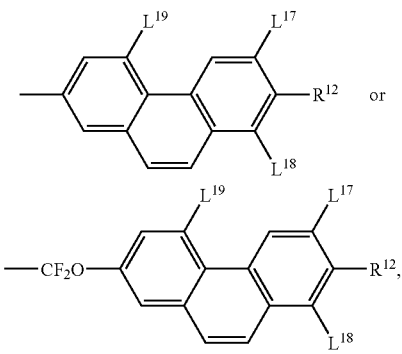

wherein R$^{12}$ is as defined above,

L$^{17}$, L$^{18}$ and L$^{19}$ independently of one another, are H or F;

q is 0, 1, 2, 3 or 4;

p is 0, 1, 2 or 3; and

R$^{13}$ and R$^{14}$ independently of one another, are an alkanyl radical having 1 to 7 carbon atoms or together are an alkylene bridge having 2 to 7 carbon atoms;

wherein in each case independently of each other, aralkyl and —O—aralkyl radicals are optionally substituted by one or more halogen, NO$_2$, alkanyl and/or alkoxy groups, with the following provisos:

1) when Z$^{13}$ is directly liked to R$^{12}$, R$^{12}$ is H, aralkyl, alkanyl or alkenyl when Z$^{13}$ is —C(=O)—O— or —C(=O)—, and Z$^{13}$ is not —CH$_2$O— or —CF$_2$O—;

2) when Z$^{14}$ is directly linked to R$^{12}$, R$^{12}$ is H, aralkyl, alkanyl or alkenyl when Z$^{14}$ is —C(=O)—O— or —C(=O)—, and Z$^{14}$ is not —CH$_2$O— or —CF$_2$O—; and 3) when Z$^{15}$ is directly linked to R$^{12}$, R$^{12}$ is H, aralkyl, alkanyl or alkenyl when Z$^{15}$ is —C(=O)—O— or —C(=O)—, and Z$^{15}$ is not —CH$_2$O— or —CF$_2$O—.

30. A compound according to claim 29, wherein Z$^{12}$ is —CH$_2$CH$_2$—, —CF$_2$CH$_2$—, —CF$_2$CF$_2$— or —CF$_2$CF$_2$—.

31. A compound of formula I

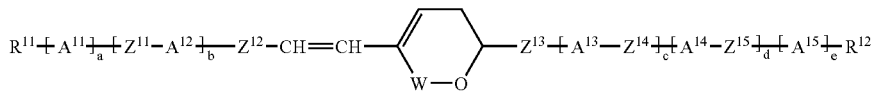

wherein a, b, c, d and e are each, independently of one another, 0 or 1;

W is —CH$_2$— or —C(=O)—;

R$^{11}$ is H, or an alkyl radical having 1 to 15 carbon atoms which is unsubstituted or mono- or polysubstituted, identically or differently, by halogen or —CN, in which one or more CH$_2$ groups are optionally replaced by —C≡C—, —CH=CH—, —O—, —S—, —C(O)—O— and/or —O—C(O)— in such a way that hetero atoms are not linked directly to one another R$^{12}$ is H, halogen, —CN, —NCS, aralkyl, —O—aralkyl or an alkyl radical having 1 to 15 carbon atoms which is unsubstituted or mono- or polysubstituted, identically or differently, by halogen or —CN, in which one or more CH$_2$ groups are optionally replaced by —C≡C—, —CH=CH—, —O—, —S—, —C(O)—O— and/or —O—C(O)— in such a way that hetero atoms are not linked directly to one another;

Z$^{11}$ is a single bond, —CH$_2$—, —CH$_2$CH$_2$—, —CF$_2$CH$_2$—, —CH$_2$CF$_2$—, —CF$_2$CF$_2$—, —CH=CH— or —C≡C—;

Z$^{12}$ is a single bond, —CH$_2$—, —CH$_2$CH$_2$—, —CF$_2$CH$_2$—, —CH$_2$CF$_2$— or —CF$_2$CF$_2$—;

Z$^{13}$ is —CH$_2$CH$_2$—, —CF$_2$CH$_2$—, —CH$_2$CF$_2$—, —CF$_2$CF$_2$—, —CH=CH—, —C≡C—, —CH$_2$O—, —CF$_2$O—, —C(O)— or —C(O)—O—;

Z$^{14}$ and Z$^{15}$ are each, independently of one another, a single bond, —CH$_2$CH$_2$—, —CF$_2$CH$_2$—, —CH$_2$CF$_2$—, —CF$_2$CF$_2$—, —CH=CH—, —C≡C—, —CH$_2$O—, —CF$_2$—, —C(O)— or —C(O)—O—;

A$^{11}$ and A$^{12}$, independently of one another, are

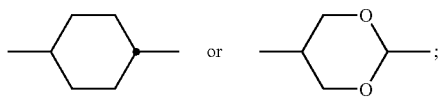

A$^{13}$ and A$^{14}$, independently of one another, are

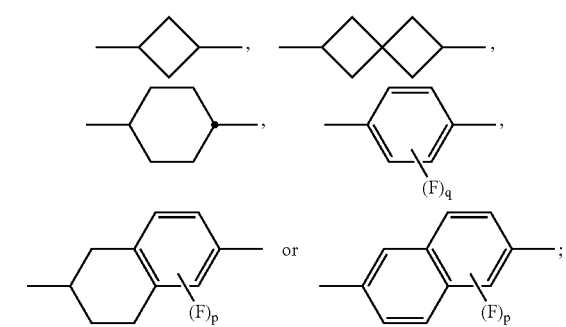

and

A$^{15}$ is

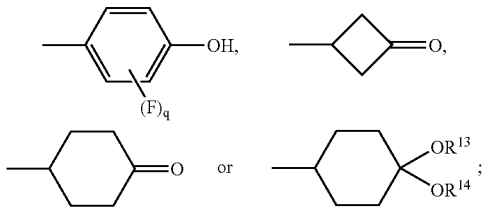

or

A$^{15}$-R$^{12}$ together are

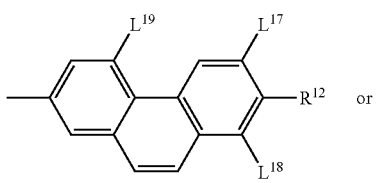

or

Z$^{13}$-[-A$^{13}$-Z$^{14}$-]$_c$-[-A$^{14}$-Z$^{15}$-]$_d$-[-A$^{15}$-]$_e$-R$^{12}$ is

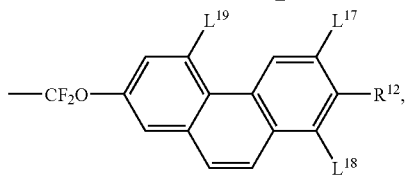

wherein R$^{12}$ is as defined above,

L$^{17}$, L$^{18}$ and L$^{19}$ independently of one another, are H or F;

q is 0, 1, 2, 3 or 4;

p is 0, 1, 2 or 3; and

R$^{13}$ and R$^{14}$ independently of one another, are an alkanyl radical having 1 to 7 carbon atoms or together are an alkylene bridge having 2 to 7 carbon atoms;

wherein in each case independently of each other, aralkyl and —O— aralkyl radicals are optionally substituted by one or more halogen, $NO_2$, alkanyl and/or alkoxy groups, with the following provisos:
1) when $Z^{13}$ is directly linked to $R^{12}$, $R^{12}$ is H, aralkyl, alkanyl or alkenyl when $Z^{13}$ is —C(=O)—O— or —C(=O)—, and $Z^{13}$ is not —$CH_2O$— or —$CF_2O$—;
2) when $Z^{14}$ is directly linked to $R^{12}$, $R^{12}$ is H, aralkyl, alkanyl or alkenyl when $Z^{14}$ is —C(=O)—O— or —C(=O)—, and $Z^{14}$ is not —$CH_2O$— or —$CF_2O$—; and
3) when $Z^{15}$ is directly linked to $R^{12}$, $R^{12}$ is H, aralkyl, alkanyl or alkenyl when $Z^{15}$ is —C(=O)—O— or —C(=O)—, and $Z^{15}$ is not —$CH_2O$— or —$CF_2O$—.

32. A liquid-crystalline medium comprising a compound of formula I according to claim 1.

33. An electro-optical display comprising a liquid-crystalline medium according to claim 32.

* * * * *

UNITED STATES PATENT AND TRADEMARK OFFICE
CERTIFICATE OF CORRECTION

PATENT NO. : 7,314,943 B2 Page 1 of 1
APPLICATION NO. : 10/852731
DATED : January 1, 2008
INVENTOR(S) : Eike Poetsch It is certified that error appears in the above-identified patent and that said Letters Patent is hereby corrected as shown below:

Column 117 Line 6 Claim 16 on graph reads "$Z^{12}$", should read -- $Z^{42}$ --
Column 119 Line 35 Claim 19 on graph reads "$Z^{12}$", should read -- $Z^{42}$ --
Column 123 Line 5 Claim 22 on graph reads "$Z^{12}$", should read -- $Z^{42}$ --

Signed and Sealed this

Twenty-second Day of December, 2009

David J. Kappos
*Director of the United States Patent and Trademark Office*